United States Patent
Czarnecki et al.

(10) Patent No.: US 9,835,737 B1
(45) Date of Patent: Dec. 5, 2017

(54) AUTONOMOUS GAMMA, X-RAY, AND PARTICLE DETECTOR

(71) Applicants: The Research Foundation for The State University of New York, Binghamton, NY (US); The Research Foundation for The State University of New York, Syracuse, NY (US); Memorial Sloan Kettering Cancer Center, New York, NY (US); Cornell University, Ithaca, NY (US); University of South Carolina, Columbia, SC (US)

(72) Inventors: Steve Czarnecki, Apalachin, NY (US); Andrzej Krol, Fayetteveille, NY (US); Krishna Mandal, Columbia, SC (US); Mark D. Poliks, Vestal, NY (US); C. Ross Schmidtlein, New York, NY (US); Michael Thompson, Ithaca, NY (US); James Turner, Vestal, NY (US)

(73) Assignees: The Research Foundation for the State University of New York, Binghamton, NY (US); The Research Foundation for the State University of New York, Syracuse, NY (US); Cornell University, Ithaca, NY (US); University of South Carolina, Columbia, SC (US); Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/468,968

(22) Filed: Mar. 24, 2017

Related U.S. Application Data

(63) Continuation of application No. 15/080,073, filed on Mar. 24, 2016, now Pat. No. 9,606,245.

(Continued)

(51) Int. Cl.
*G01T 1/20* (2006.01)
*A61B 6/03* (2006.01)
(Continued)

(52) U.S. Cl.
CPC .............. *G01T 1/208* (2013.01); *A61B 6/037* (2013.01); *A61B 6/501* (2013.01); *G01T 1/2018* (2013.01); *G01T 1/245* (2013.01)

(58) Field of Classification Search
CPC ........ A61B 6/037; A61B 6/501; G01T 1/2006; G01T 1/2018
See application file for complete search history.

(56) References Cited

U.S. PATENT DOCUMENTS 4,292,014 A     9/1981    Lupke et al.
4,395,635 A     7/1983    Friauf et al.
(Continued)

FOREIGN PATENT DOCUMENTS

CA      2279959 A1    8/1998
CA      2492587 A1    1/2004
(Continued)

*Primary Examiner* — Mark R Gaworecki
(74) *Attorney, Agent, or Firm* — Steven M. Hoffberg; Tully Rinckey PLLC

(57) ABSTRACT

A system and method for imaging gamma- and x-ray, and charged particles sources employing a three dimensional array of scintillation elements arranged surrounding an emission source. According to a preferred embodiment, each element of the array comprises a scintillator element, a solid-state photon detector, and processing electronics to output an electronic signal. The elements may be efficiently packed in both the X-Y plane and stacked in the Z-axis, to provide depth of interaction information. The elements of the array are preferably hierarchically arranged with control electronics provided together for subarray modules (e.g., an n×m×1 module), and synchronization electronics provided at a larger scale. The modules preferably communicate with (Continued)

a control system through a shared addressable packet switched digital communication network with a control and imaging system, and receive control information from that system through the network.

20 Claims, 9 Drawing Sheets

Related U.S. Application Data

(60) Provisional application No. 62/137,276, filed on Mar. 24, 2015.

(51) Int. Cl.
*G01T 1/208* (2006.01)
*G01T 1/24* (2006.01)
*A61B 6/00* (2006.01)

(56) References Cited

U.S. PATENT DOCUMENTS

| | | | |
|---|---|---|---|
| 4,415,807 A | 11/1983 | Friauf et al. |
| 4,475,192 A | 10/1984 | Fernow et al. |
| 4,559,597 A | 12/1985 | Mullani |
| 4,841,526 A | 6/1989 | Wilson et al. |
| 4,864,140 A | 9/1989 | Rogers et al. |
| 4,980,552 A | 12/1990 | Cho et al. |
| 5,103,098 A | 4/1992 | Fenyves |
| 5,241,181 A | 8/1993 | Mertens et al. |
| 5,245,616 A | 9/1993 | Olson |
| 5,252,830 A | 10/1993 | Weinberg |
| 5,272,343 A | 12/1993 | Stearns |
| 5,272,344 A | 12/1993 | Williams |
| 5,300,782 A | 4/1994 | Johnston et al. |
| 5,323,006 A | 6/1994 | Thompson et al. |
| 5,331,553 A | 7/1994 | Muehllehner et al. |
| 5,378,893 A | 1/1995 | Murray et al. |
| 5,424,946 A | 6/1995 | Stearns |
| 5,432,824 A | 7/1995 | Zheng et al. |
| 5,442,637 A | 8/1995 | Nguyen |
| 5,519,221 A | 5/1996 | Weinberg |
| 5,528,591 A | 6/1996 | Lauer |
| 5,543,622 A | 8/1996 | Stearns |
| 5,602,395 A | 2/1997 | Nellemann et al. |
| 5,608,221 A | 3/1997 | Bertelsen et al. |
| 5,625,190 A | 4/1997 | Crandall |
| 5,633,867 A | 5/1997 | Ben-Nun et al. |
| 5,751,000 A | 5/1998 | McCroskey et al. |
| 5,821,541 A | 10/1998 | Tumer |
| 5,825,748 A | 10/1998 | Barkey et al. |
| 5,834,779 A | 11/1998 | Shao et al. |
| 5,841,140 A | 11/1998 | Mc Croskey et al. |
| 5,852,602 A | 12/1998 | Sugawara |
| 5,900,636 A | 5/1999 | Nellemann et al. |
| 5,965,891 A | 10/1999 | Weinberg |
| 5,990,482 A | 11/1999 | Bertelsen et al. |
| 5,998,793 A | 12/1999 | Shao et al. |
| 5,999,588 A | 12/1999 | Shao et al. |
| 6,008,493 A | 12/1999 | Shao et al. |
| 6,038,606 A | 3/2000 | Brooks et al. |
| 6,072,177 A | 6/2000 | McCroskey et al. |
| 6,100,531 A | 8/2000 | Hines et al. |
| 6,114,703 A | 9/2000 | Levin et al. |
| 6,194,728 B1 | 2/2001 | Bosnjakovic |
| 6,205,120 B1 | 3/2001 | Packer et al. |
| 6,215,903 B1 | 4/2001 | Cook |
| 6,219,713 B1 | 4/2001 | Ruutu et al. |
| 6,229,145 B1 | 5/2001 | Weinberg |
| 6,232,604 B1 | 5/2001 | McDaniel et al. |
| 6,239,438 B1 | 5/2001 | Schubert |
| 6,243,358 B1 | 6/2001 | Monin |
| 6,255,655 B1 | 7/2001 | Mc Croskey et al. |
| 6,288,399 B1 | 9/2001 | Andreaco et al. |
| 6,297,506 B1 | 10/2001 | Young et al. |
| 6,310,349 B1 | 10/2001 | Wong et al. |
| 6,323,489 B1 | 11/2001 | McClellan |
| 6,337,865 B1 | 1/2002 | Seto et al. |
| 6,347,337 B1 | 2/2002 | Shah et al. |
| 6,362,478 B1 | 3/2002 | McDaniel et al. |
| 6,373,059 B1 | 4/2002 | Stearns et al. |
| 6,410,919 B1 | 6/2002 | Nickles |
| 6,410,920 B1 | 6/2002 | Shao et al. |
| 6,449,331 B1 | 9/2002 | Nutt et al. |
| 6,462,342 B1 | 10/2002 | Stearns |
| 6,509,565 B2 | 1/2003 | Nygard et al. |
| 6,521,893 B2 | 2/2003 | Stark |
| 6,525,322 B2 | 2/2003 | Wong et al. |
| 6,525,323 B1 | 2/2003 | Vesel et al. |
| 6,545,280 B2 | 4/2003 | Weinberg |
| 6,552,348 B2 | 4/2003 | Cherry et al. |
| 6,590,213 B2 | 7/2003 | Wollenweber |
| 6,590,215 B2 | 7/2003 | Nygard et al. |
| 6,593,575 B2 | 7/2003 | Fries |
| 6,594,701 B1 | 7/2003 | Forin |
| 6,603,125 B1 | 8/2003 | Cooke et al. |
| 6,624,420 B1 | 9/2003 | Chai et al. |
| 6,624,422 B2 | 9/2003 | Williams et al. |
| 6,628,984 B2 | 9/2003 | Weinberg |
| 6,654,787 B1 | 11/2003 | Aronson et al. |
| 6,670,614 B1 | 12/2003 | Plut et al. |
| 6,683,850 B1 | 1/2004 | Dunning et al. |
| 6,723,993 B2 | 4/2004 | Cooke et al. |
| 6,724,721 B1 | 4/2004 | Cheriton |
| 6,740,882 B2 | 5/2004 | Weinberg |
| 6,803,579 B2 | 10/2004 | Williams et al. |
| 6,852,978 B2 | 2/2005 | Williams et al. |
| 6,858,850 B2 | 2/2005 | Williams et al. |
| 6,921,901 B1 | 7/2005 | Chai et al. |
| 6,936,822 B2 | 8/2005 | Wong et al. |
| 7,016,458 B2 | 3/2006 | Francke |
| 7,026,621 B2 | 4/2006 | Stonger et al. |
| 7,030,382 B2 | 4/2006 | Williams et al. |
| 7,038,212 B2 | 5/2006 | Wollenweber et al. |
| 7,039,227 B2 | 5/2006 | Tanaka et al. |
| 7,084,403 B2 | 8/2006 | Srivastava et al. |
| 7,085,405 B1 | 8/2006 | Levkovitz et al. |
| 7,088,901 B2 | 8/2006 | Kim et al. |
| 7,091,489 B2 | 8/2006 | Schlyer et al. |
| 7,102,134 B2 | 9/2006 | Weinberg |
| 7,102,135 B2 | 9/2006 | Lecoq |
| 7,115,874 B2 | 10/2006 | Peter et al. |
| 7,115,875 B1 | 10/2006 | Worstell |
| 7,126,126 B2 | 10/2006 | Schyler et al. |
| 7,129,496 B2 | 10/2006 | Stearns et al. |
| 7,129,497 B2 | 10/2006 | Wollenweber et al. |
| 7,132,664 B1 | 11/2006 | Crosetto |
| 7,141,794 B2 | 11/2006 | Srivastava et al. |
| 7,145,149 B2 | 12/2006 | Cooke et al. |
| 7,180,074 B1 | 2/2007 | Crosetto |
| 7,193,208 B1 | 3/2007 | Burr et al. |
| 7,202,477 B2 | 4/2007 | Srivastava et al. |
| 7,211,799 B2 | 5/2007 | Heukensfeldt |
| 7,217,928 B2 | 5/2007 | Crosetto |
| 7,227,149 B2 | 6/2007 | Stearns et al. |
| 7,238,946 B2 | 7/2007 | Joung et al. |
| 7,286,867 B2 | 10/2007 | Schlyer et al. |
| 7,301,144 B2 | 11/2007 | Williams et al. |
| 7,301,153 B2 | 11/2007 | Eriksson et al. |
| 7,304,309 B2 | 12/2007 | Suhami |
| 7,305,486 B2 | 12/2007 | Ghose et al. |
| 7,324,624 B2 | 1/2008 | Sibomana et al. |
| 7,329,874 B2 | 2/2008 | Shah |
| 7,332,721 B2 | 2/2008 | Worstell |
| 7,342,232 B2 | 3/2008 | Xie et al. |
| 7,345,281 B2 | 3/2008 | Jansen et al. |
| 7,352,840 B1 | 4/2008 | Nagarkar et al. |
| 7,359,535 B2 | 4/2008 | Salla et al. |
| 7,365,333 B1 | 4/2008 | Shah et al. |
| 7,381,958 B2 | 6/2008 | Karp et al. |
| 7,381,959 B2 | 6/2008 | Manjeshwar et al. |
| 7,385,201 B1 | 6/2008 | Joung et al. |
| 7,394,053 B2 | 7/2008 | Frangioni et al. |
| 7,397,038 B2 | 7/2008 | Persyk et al. |

(56) References Cited

U.S. PATENT DOCUMENTS

| | | | |
|---|---|---|---|
| 7,405,405 B2 | 7/2008 | Stearns et al. |
| 7,412,280 B2 | 8/2008 | Hertel et al. |
| 7,447,345 B2 | 11/2008 | Shanmugam et al. |
| 7,465,927 B2 | 12/2008 | Panin et al. |
| 7,482,593 B2 | 1/2009 | Shao |
| 7,489,799 B2 | 2/2009 | Nilsen et al. |
| 7,504,634 B2 | 3/2009 | Shah |
| 7,507,968 B2 | 3/2009 | Wollenweber et al. |
| 7,519,412 B2 | 4/2009 | Mistretta |
| 7,526,565 B2 | 4/2009 | Amini et al. |
| 7,535,011 B2 | 5/2009 | Chowdhury et al. |
| 7,554,089 B2 | 6/2009 | Burr et al. |
| 7,557,351 B2 | 7/2009 | Worstell |
| 7,576,329 B2 | 8/2009 | Srivastava et al. |
| 7,579,599 B2 | 8/2009 | Zhang et al. |
| 7,593,323 B2 | 9/2009 | Hiddle |
| 7,605,373 B2 | 10/2009 | Srivastava |
| 7,626,389 B2 | 12/2009 | Fiedler et al. |
| 7,638,771 B2 | 12/2009 | Breeding et al. |
| 7,649,909 B1 | 1/2010 | Archard et al. |
| 7,667,199 B2 | 2/2010 | Fries |
| 7,667,457 B2 | 2/2010 | Linz et al. |
| 7,671,339 B2 | 3/2010 | Shibuya et al. |
| 7,680,151 B2 | 3/2010 | Dougall et al. |
| 7,680,993 B2 | 3/2010 | Dougall |
| 7,684,589 B2 | 3/2010 | Nilsen et al. |
| 7,693,998 B2 | 4/2010 | Patiejunas |
| 7,700,003 B2 | 4/2010 | Martins Loureiro et al. |
| 7,705,314 B2 | 4/2010 | Cook et al. |
| 7,720,973 B2 | 5/2010 | Patiejunas |
| 7,723,694 B2 | 5/2010 | Frach et al. |
| 7,724,775 B2 | 5/2010 | Saito |
| 7,737,404 B2 | 6/2010 | Musrock |
| 7,737,408 B2 | 6/2010 | Doshi |
| 7,749,637 B2 | 7/2010 | Owejan et al. |
| 7,755,054 B1 | 7/2010 | Shah et al. |
| 7,756,310 B2 | 7/2010 | Manjeshwar et al. |
| 7,759,625 B2 | 7/2010 | Frangioni et al. |
| 7,759,650 B2 | 7/2010 | Heringa et al. |
| 7,778,787 B2 | 8/2010 | Fiedler et al. |
| 7,791,029 B2 | 9/2010 | Michaud et al. |
| 7,800,070 B2 | 9/2010 | Weinberg et al. |
| 7,807,974 B2 | 10/2010 | Ishitsu et al. |
| 7,818,047 B2 | 10/2010 | Tumer et al. |
| 7,825,384 B1 | 11/2010 | Saveliev |
| 7,844,681 B2 | 11/2010 | Depelteau |
| 7,847,552 B2 | 12/2010 | Haworth et al. |
| 7,884,331 B2 | 2/2011 | Majewski et al. |
| 7,899,925 B2 | 3/2011 | Ghose et al. |
| 7,911,994 B2 | 3/2011 | Clarke et al. |
| 7,945,079 B2 | 5/2011 | Rosen |
| 7,953,265 B2 | 5/2011 | Sirohey et al. |
| 7,956,331 B2 | 6/2011 | Lewellen et al. |
| 7,961,613 B2 | 6/2011 | Yeung et al. |
| 7,968,852 B1 | 6/2011 | Malmin et al. |
| 7,974,247 B2 | 7/2011 | Takatori et al. |
| 7,983,735 B2 | 7/2011 | Manjeshwar |
| 8,000,513 B2 | 8/2011 | Defrise et al. |
| 8,003,948 B2 | 8/2011 | Haselman et al. |
| 8,014,614 B2 | 9/2011 | Cook |
| 8,017,902 B2 | 9/2011 | Gratz et al. |
| 8,017,914 B2 | 9/2011 | Wollenweber et al. |
| 8,062,419 B1 | 11/2011 | Andreaco et al. |
| 8,068,457 B2 | 11/2011 | Pi et al. |
| 8,068,896 B2 | 11/2011 | Daghighian et al. |
| 8,069,251 B2 | 11/2011 | Thornburgh et al. |
| 8,071,949 B2 | 12/2011 | Majewski et al. |
| 8,084,742 B1 | 12/2011 | Nagarkar |
| 8,086,692 B2 | 12/2011 | Sridhar et al. |
| 8,094,908 B2 | 1/2012 | Stearns |
| 8,098,916 B2 | 1/2012 | Thielemans et al. |
| 8,110,805 B2 | 2/2012 | Panin |
| 8,110,806 B2 | 2/2012 | Burr et al. |
| 8,144,962 B2 | 3/2012 | Busch et al. |
| 8,145,698 B1 | 3/2012 | Kaufman et al. |
| 8,153,983 B1 | 4/2012 | Shah et al. |
| 8,155,415 B2 | 4/2012 | Faul et al. |
| 8,164,063 B2 | 4/2012 | Frach et al. |
| 8,171,147 B1 | 5/2012 | Kaufman et al. |
| 8,193,815 B2 | 6/2012 | Prescher et al. |
| 8,194,690 B1 | 6/2012 | Steele et al. |
| 8,194,937 B2 | 6/2012 | Chen |
| 8,204,172 B1 | 6/2012 | Hsieh et al. |
| 8,223,628 B2 | 7/2012 | Thyagarajan |
| 8,229,199 B2 | 7/2012 | Chen et al. |
| 8,239,548 B2 | 8/2012 | Thornburgh et al. |
| 8,258,480 B2 | 9/2012 | Olcott et al. |
| 8,269,177 B2 | 9/2012 | Kim et al. |
| 8,274,054 B2 | 9/2012 | Pratx et al. |
| 8,299,440 B2 | 10/2012 | Wainer |
| 8,304,736 B2 | 11/2012 | Gagnon |
| 8,309,932 B2 | 11/2012 | Haselman et al. |
| 8,312,147 B2 | 11/2012 | Kaufman et al. |
| 8,315,353 B1 | 11/2012 | Hsieh et al. |
| 8,334,697 B2 | 12/2012 | Overweg et al. |
| 8,340,377 B2 | 12/2012 | McFarland et al. |
| 8,341,401 B1 | 12/2012 | Kaufman et al. |
| 8,343,509 B2 | 1/2013 | Stritzker et al. |
| 8,350,220 B2 | 1/2013 | Moor |
| 8,355,551 B2 | 1/2013 | Thielemans et al. |
| 8,357,486 B2 | 1/2013 | Stritzker et al. |
| 8,369,928 B2 | 2/2013 | Arseneau et al. |
| 8,373,132 B2 | 2/2013 | Baeumer et al. |
| 8,384,037 B2 | 2/2013 | Aykac et al. |
| 8,388,931 B2 | 3/2013 | Lopez et al. |
| 8,395,127 B1 | 3/2013 | Frach et al. |
| 8,399,848 B2 | 3/2013 | Frach et al. |
| 8,405,035 B1 | 3/2013 | Nagarkar |
| 8,410,449 B2 | 4/2013 | Thon et al. |
| 8,410,776 B2 | 4/2013 | Schmand et al. |
| 8,431,904 B2 | 4/2013 | Lewellen et al. |
| 8,443,057 B1 | 5/2013 | Kaufman et al. |
| 8,450,692 B2 | 5/2013 | Siegel et al. |
| 8,450,693 B2 | 5/2013 | Stearns |
| 8,466,419 B2 | 6/2013 | Gagnon |
| 8,467,848 B2 | 6/2013 | Solf et al. |
| 8,472,683 B2 | 6/2013 | Manjeshwar et al. |
| 8,472,688 B2 | 6/2013 | Samsonov et al. |
| 8,476,593 B2 | 7/2013 | Degenhardt et al. |
| 8,476,594 B2 | 7/2013 | Frach et al. |
| 8,478,015 B2 | 7/2013 | Faul et al. |
| 8,481,947 B2 | 7/2013 | Woldemichael |
| 8,488,857 B2 | 7/2013 | Young et al. |
| 8,497,484 B2 | 7/2013 | Chmeissani Raad et al. |
| 8,511,894 B2 | 8/2013 | Gagnon et al. |
| 8,525,116 B2 | 9/2013 | Schulz et al. |
| 8,527,034 B2 | 9/2013 | Schroder et al. |
| 8,530,846 B2 | 9/2013 | Cook et al. |
| 8,532,357 B2 | 9/2013 | Wollenweber et al. |
| 8,536,517 B2 | 9/2013 | Berheide et al. |
| 8,542,582 B2 | 9/2013 | Clarke et al. |
| 8,547,100 B2 | 10/2013 | Solf et al. |
| 8,577,114 B2 | 11/2013 | Faul et al. |
| 8,577,994 B2 | 11/2013 | Shuster |
| 8,598,534 B2 | 12/2013 | Solf |
| 8,598,536 B2 | 12/2013 | Jarron et al. |
| 8,604,440 B2 | 12/2013 | Frisch et al. |
| 8,604,795 B2 | 12/2013 | Overweg et al. |
| 8,605,988 B2 | 12/2013 | Tao et al. |
| 8,617,422 B2 | 12/2013 | Koschan et al. |
| 8,624,193 B2 | 1/2014 | Aykac et al. |
| 8,650,313 B2 | 2/2014 | Thornburgh et al. |
| 8,674,312 B2 | 3/2014 | Szupryczynski et al. |
| 8,698,087 B2 | 4/2014 | Surti et al. |
| 8,699,771 B2 | 4/2014 | Wollenweber et al. |
| 8,713,189 B2 | 4/2014 | Frazer |
| 8,716,647 B2 | 5/2014 | O'Mathuna et al. |
| 8,716,664 B2 | 5/2014 | Caruba et al. |
| 8,716,669 B2 | 5/2014 | Miyaoka et al. |
| 8,723,521 B2 | 5/2014 | Schulz et al. |
| 8,735,834 B2 | 5/2014 | Millett et al. |
| 8,735,835 B2 | 5/2014 | Caruba |
| 8,745,263 B2 | 6/2014 | Kreuzenstein et al. |
| 8,755,586 B2 | 6/2014 | King et al. |

(56) References Cited

U.S. PATENT DOCUMENTS

| | | |
|---|---|---|
| 8,761,478 B2 | 6/2014 | Hsieh et al. |
| 8,767,908 B2 | 7/2014 | Leahy et al. |
| 8,779,366 B2 | 7/2014 | Wieczorek |
| 8,787,620 B2 | 7/2014 | Laurence et al. |
| 8,796,637 B1 | 8/2014 | Burr et al. |
| 8,809,790 B2 | 8/2014 | Woldemichael |
| 8,809,793 B2 | 8/2014 | Wagadarikar et al. |
| 8,816,286 B2 | 8/2014 | Cho |
| 8,818,488 B2 | 8/2014 | Caruba et al. |
| 8,822,931 B2 | 9/2014 | Laurence et al. |
| 8,822,933 B2 | 9/2014 | Fries et al. |
| 8,822,935 B2 | 9/2014 | Frach et al. |
| 8,828,355 B2 | 9/2014 | Keller et al. |
| 8,837,799 B2 | 9/2014 | Wollenweber |
| 8,866,086 B2 | 10/2014 | Michel et al. |
| 8,884,240 B1 | 11/2014 | Shah et al. |
| 8,897,518 B2 | 11/2014 | Solf et al. |
| 8,903,152 B2 | 12/2014 | Asma et al. |
| 8,907,290 B2 | 12/2014 | Kim et al. |
| 8,913,810 B2 | 12/2014 | Panin et al. |
| 8,921,754 B2 | 12/2014 | Frach |
| 8,921,796 B1 | 12/2014 | Arseneau et al. |
| 8,933,409 B2 | 1/2015 | Siegel et al. |
| 8,933,411 B2 | 1/2015 | Solf |
| 8,934,959 B2 | 1/2015 | Peligrad |
| 8,937,285 B2 | 1/2015 | Kim et al. |
| 8,941,071 B1 | 1/2015 | Stearns |
| 8,942,445 B2 | 1/2015 | Foo et al. |
| 8,969,815 B2 | 3/2015 | Caruba et al. |
| 8,969,816 B2 | 3/2015 | Caruba et al. |
| 8,969,829 B2 | 3/2015 | Wollenweber et al. |
| 8,975,907 B2 | 3/2015 | Prescher et al. |
| 8,987,659 B2 | 3/2015 | Laurence et al. |
| 8,992,918 B2 | 3/2015 | Strittmatter |
| 9,031,300 B1 | 5/2015 | Manjeshwar et al. |
| 9,044,153 B2 | 6/2015 | Panin |
| 9,063,520 B2 | 6/2015 | Mann |
| 9,076,707 B2 | 7/2015 | Harmon |
| 9,078,622 B2 | 7/2015 | Wollenweber et al. |
| 9,091,771 B2 | 7/2015 | Henseler et al. |
| 9,140,804 B2 | 9/2015 | Kim |
| 9,151,851 B2 | 10/2015 | Fries et al. |
| 9,155,514 B2 | 10/2015 | Panin et al. |
| 9,176,240 B2 | 11/2015 | Gagnon et al. |
| 9,176,241 B2 | 11/2015 | Frach |
| 9,182,506 B2 | 11/2015 | Kim et al. |
| 9,207,334 B1 | 12/2015 | Ito et al. |
| 9,217,795 B2 | 12/2015 | Hansen et al. |
| 9,229,115 B2 | 1/2016 | Griesmer et al. |
| 9,244,180 B2 | 1/2016 | Frisch et al. |
| 9,268,033 B2 | 2/2016 | Frach et al. |
| 9,279,892 B2 | 3/2016 | Kim et al. |
| 2001/0001107 A1 | 5/2001 | Weinberg |
| 2001/0040219 A1 | 11/2001 | Cherry et al. |
| 2001/0056234 A1 | 12/2001 | Weinberg |
| 2002/0113211 A1 | 8/2002 | Nygard et al. |
| 2002/0145115 A1 | 10/2002 | Nygard et al. |
| 2002/0195565 A1 | 12/2002 | Lecoq |
| 2003/0038240 A1 | 2/2003 | Weinberg |
| 2003/0047686 A1 | 3/2003 | Fries |
| 2003/0047687 A1 | 3/2003 | Wollenweber |
| 2003/0057375 A1 | 3/2003 | Williams et al. |
| 2003/0062482 A1 | 4/2003 | Williams et al. |
| 2003/0105397 A1 | 6/2003 | Tumer et al. |
| 2003/0116713 A1 | 6/2003 | Cooke et al. |
| 2004/0016884 A1 | 1/2004 | Williams et al. |
| 2004/0026620 A1 | 2/2004 | Peter et al. |
| 2004/0084625 A1 | 5/2004 | Williams et al. |
| 2004/0129886 A1 | 7/2004 | Lecoq |
| 2004/0164249 A1 | 8/2004 | Crosetto |
| 2004/0183022 A1 | 9/2004 | Weinberg |
| 2004/0195512 A1 | 10/2004 | Crosetto |
| 2004/0200966 A1 | 10/2004 | Ramsden |
| 2004/0210132 A1 | 10/2004 | Manjeshwar |
| 2004/0258286 A1 | 12/2004 | Salla et al. |
| 2004/0260176 A1 | 12/2004 | Wollenweber et al. |
| 2005/0004452 A1 | 1/2005 | Hertel et al. |
| 2005/0015004 A1 | 1/2005 | Hertel et al. |
| 2005/0023473 A1 | 2/2005 | Burr et al. |
| 2005/0031293 A1 | 2/2005 | Kim et al. |
| 2005/0035297 A1 | 2/2005 | Crosetto |
| 2005/0061983 A1 | 3/2005 | Stonger et al. |
| 2005/0082484 A1 | 4/2005 | Srivastava et al. |
| 2005/0082486 A1 | 4/2005 | Schlyer et al. |
| 2005/0113667 A1 | 5/2005 | Schlyer et al. |
| 2005/0117694 A1 | 6/2005 | Francke |
| 2005/0129295 A1 | 6/2005 | Shanmugam et al. |
| 2005/0151084 A1 | 7/2005 | Zibulevsky et al. |
| 2005/0156112 A1 | 7/2005 | Williams et al. |
| 2005/0167599 A1 | 8/2005 | Schlyer et al. |
| 2005/0230626 A1 | 10/2005 | Crosetto |
| 2005/0242288 A1 | 11/2005 | Wollenweber et al. |
| 2005/0253073 A1 | 11/2005 | Joram et al. |
| 2005/0253076 A1 | 11/2005 | Wollenweber et al. |
| 2005/0285041 A1 | 12/2005 | Srivastava et al. |
| 2006/0029544 A1 | 2/2006 | Sutcliffe-Goulden et al. |
| 2006/0108509 A1 | 5/2006 | Frangioni et al. |
| 2006/0116567 A1 | 6/2006 | Nilsen et al. |
| 2006/0138315 A1 | 6/2006 | Williams et al. |
| 2006/0145082 A1 | 7/2006 | Stearns et al. |
| 2006/0163485 A1 | 7/2006 | Stearns et al. |
| 2006/0197023 A1 | 9/2006 | Srivastava et al. |
| 2006/0202125 A1 | 9/2006 | Suhami |
| 2006/0231765 A1 | 10/2006 | Worstell |
| 2006/0237654 A1 | 10/2006 | Srivastava et al. |
| 2006/0261275 A1 | 11/2006 | Stearns et al. |
| 2007/0010731 A1 | 1/2007 | Mistretta |
| 2007/0040122 A1 | 2/2007 | Manjeshwar et al. |
| 2007/0057189 A1 | 3/2007 | Jansen et al. |
| 2007/0090300 A1 | 4/2007 | Sibomana et al. |
| 2007/0116168 A1 | 5/2007 | Fries |
| 2007/0131866 A1 | 6/2007 | Srivastava et al. |
| 2007/0181814 A1 | 8/2007 | Crosetto |
| 2007/0205368 A1 | 9/2007 | Heukensfeldt Jansen et al. |
| 2007/0221850 A1 | 9/2007 | Panin et al. |
| 2007/0263764 A1 | 11/2007 | Mccallum et al. |
| 2007/0267576 A1 | 11/2007 | Loureiro et al. |
| 2007/0269093 A1 | 11/2007 | Jones et al. |
| 2007/0270693 A1 | 11/2007 | Fiedler et al. |
| 2007/0278409 A1 | 12/2007 | Cook et al. |
| 2007/0290140 A1 | 12/2007 | Lenox et al. |
| 2008/0011953 A1 | 1/2008 | Srivastava et al. |
| 2008/0069414 A1 | 3/2008 | Manjeshwar et al. |
| 2008/0118134 A1 | 5/2008 | Sirohey et al. |
| 2008/0128623 A1 | 6/2008 | Srivastava |
| 2008/0135769 A1 | 6/2008 | Rosen |
| 2008/0137930 A1 | 6/2008 | Rosen |
| 2008/0156993 A1 | 7/2008 | Weinberg et al. |
| 2008/0164875 A1 | 7/2008 | Haworth et al. |
| 2008/0197288 A1 | 8/2008 | Worstell |
| 2008/0203309 A1 | 8/2008 | Frach et al. |
| 2008/0210876 A1 | 9/2008 | Ishitsu et al. |
| 2008/0219534 A1 | 9/2008 | Faul et al. |
| 2008/0230707 A1 | 9/2008 | Idoine |
| 2008/0237475 A1 | 10/2008 | Michaud et al. |
| 2008/0240535 A1 | 10/2008 | Frangioni et al. |
| 2008/0253525 A1 | 10/2008 | Boyden et al. |
| 2008/0253526 A1 | 10/2008 | Boyden et al. |
| 2008/0253527 A1 | 10/2008 | Boyden et al. |
| 2008/0253528 A1 | 10/2008 | Boyden et al. |
| 2008/0253529 A1 | 10/2008 | Boyden et al. |
| 2008/0253530 A1 | 10/2008 | Boyden et al. |
| 2008/0253531 A1 | 10/2008 | Boyden et al. |
| 2008/0253627 A1 | 10/2008 | Boyden et al. |
| 2008/0260646 A1 | 10/2008 | Keller et al. |
| 2008/0284428 A1 | 11/2008 | Fiedler et al. |
| 2009/0018438 A1 | 1/2009 | Schroder et al. |
| 2009/0072151 A1 | 3/2009 | Zhang et al. |
| 2009/0072153 A1 | 3/2009 | Musrock |
| 2009/0074281 A1 | 3/2009 | McFarland et al. |
| 2009/0110256 A1 | 4/2009 | Thielemans et al. |
| 2009/0146065 A1 | 6/2009 | Srivastava et al. |
| 2009/0159804 A1 | 6/2009 | Shibuya et al. |
| 2009/0161931 A1 | 6/2009 | Tao et al. |

(56) References Cited

U.S. PATENT DOCUMENTS

| | | |
|---|---|---|
| 2009/0161933 A1 | 6/2009 | Chen |
| 2009/0169085 A1 | 7/2009 | Nilsen et al. |
| 2009/0175523 A1 | 7/2009 | Chen et al. |
| 2009/0220419 A1 | 9/2009 | Lopez et al. |
| 2009/0224158 A1 | 9/2009 | Haselman et al. |
| 2009/0236532 A1 | 9/2009 | Frach et al. |
| 2009/0257633 A1 | 10/2009 | Cook |
| 2009/0262996 A1 | 10/2009 | Samsonov et al. |
| 2009/0264753 A1 | 10/2009 | von Schulthess et al. |
| 2009/0302228 A1 | 12/2009 | Hadjioannou et al. |
| 2010/0010343 A1 | 1/2010 | Daghighian et al. |
| 2010/0012846 A1 | 1/2010 | Wang |
| 2010/0014728 A1 | 1/2010 | Stearns |
| 2010/0033186 A1 | 2/2010 | Overweg et al. |
| 2010/0046821 A1 | 2/2010 | Manjeshwar et al. |
| 2010/0072375 A1 | 3/2010 | Panin |
| 2010/0074500 A1 | 3/2010 | Defrise et al. |
| 2010/0076300 A1 | 3/2010 | Arseneau et al. |
| 2010/0078566 A1 | 4/2010 | Moor |
| 2010/0078569 A1 | 4/2010 | Jarron et al. |
| 2010/0084559 A1 | 4/2010 | Aykac et al. |
| 2010/0098312 A1 | 4/2010 | Leahy et al. |
| 2010/0104505 A1 | 4/2010 | O'Connor |
| 2010/0108894 A1 | 5/2010 | Pratx et al. |
| 2010/0108896 A1 | 5/2010 | Surti et al. |
| 2010/0108900 A1 | 5/2010 | Burr et al. |
| 2010/0116994 A1 | 5/2010 | Wollenweber et al. |
| 2010/0135559 A1 | 6/2010 | Morich et al. |
| 2010/0140486 A1 | 6/2010 | Idoine |
| 2010/0148039 A1 | 6/2010 | Gratz et al. |
| 2010/0152577 A1 | 6/2010 | Young et al. |
| 2010/0166274 A1 | 7/2010 | Busch et al. |
| 2010/0182011 A1 | 7/2010 | Prescher et al. |
| 2010/0189324 A1 | 7/2010 | Wollenweber et al. |
| 2010/0198061 A9 | 8/2010 | Daghighian et al. |
| 2010/0200763 A1 | 8/2010 | Thon et al. |
| 2010/0219345 A1 | 9/2010 | Franch et al. |
| 2010/0219347 A1 | 9/2010 | Schulz et al. |
| 2010/0220909 A1 | 9/2010 | Thielemans et al. |
| 2010/0230601 A1 | 9/2010 | Martins Loureiro et al. |
| 2010/0246919 A1 | 9/2010 | Wainer |
| 2010/0252723 A1 | 10/2010 | Frach et al. |
| 2010/0268074 A1 | 10/2010 | Van Loef et al. |
| 2010/0294940 A1 | 11/2010 | Wieczorek |
| 2010/0314546 A1 | 12/2010 | Ronda |
| 2010/0327227 A1 | 12/2010 | Kurata et al. |
| 2011/0001053 A1 | 1/2011 | Solf |
| 2011/0018541 A1 | 1/2011 | Solf et al. |
| 2011/0073764 A1 | 3/2011 | Woldemichael |
| 2011/0079722 A1 | 4/2011 | Gagnon |
| 2011/0105892 A1 | 5/2011 | Peligrad |
| 2011/0116695 A1 | 5/2011 | Wollenweber et al. |
| 2011/0117094 A1 | 5/2011 | Strittmatter et al. |
| 2011/0133091 A1 | 6/2011 | Frach et al. |
| 2011/0142304 A1 | 6/2011 | Stearns |
| 2011/0142315 A1 | 6/2011 | Hsieh et al. |
| 2011/0142367 A1 | 6/2011 | Stearns et al. |
| 2011/0150181 A1 | 6/2011 | Cook et al. |
| 2011/0174980 A1 | 7/2011 | Gagnon |
| 2011/0192982 A1 | 8/2011 | Henseler et al. |
| 2011/0210255 A1 | 9/2011 | Kim et al. |
| 2011/0212090 A1 | 9/2011 | Pedersen et al. |
| 2011/0215248 A1 | 9/2011 | Lewellen et al. |
| 2011/0218432 A1 | 9/2011 | Tumer |
| 2011/0220802 A1 | 9/2011 | Frisch et al. |
| 2011/0228999 A1 | 9/2011 | Hsieh |
| 2011/0240864 A1 | 10/2011 | Degenhardt et al. |
| 2011/0248175 A1 | 10/2011 | Frach et al. |
| 2011/0248765 A1 | 10/2011 | Tumer et al. |
| 2011/0253901 A1 | 10/2011 | Chmeissani Raad et al. |
| 2011/0263965 A1 | 10/2011 | Kang et al. |
| 2011/0272587 A1 | 11/2011 | Siegel et al. |
| 2011/0278466 A1 | 11/2011 | Frach et al. |
| 2011/0291017 A1 | 12/2011 | Frach |
| 2011/0299747 A1 | 12/2011 | Solf et al. |
| 2011/0301918 A1 | 12/2011 | Haselman et al. |
| 2012/0018644 A1 | 1/2012 | Caruba |
| 2012/0019064 A1 | 1/2012 | Caruba et al. |
| 2012/0022361 A1 | 1/2012 | Caruba et al. |
| 2012/0022362 A1 | 1/2012 | Caruba et al. |
| 2012/0022364 A1 | 1/2012 | Caruba et al. |
| 2012/0061576 A1 | 3/2012 | Degenhardt et al. |
| 2012/0068076 A1 | 3/2012 | Daghighian |
| 2012/0068077 A1 | 3/2012 | Frach et al. |
| 2012/0085911 A1 | 4/2012 | McCroskey et al. |
| 2012/0093380 A1 | 4/2012 | Gagnon et al. |
| 2012/0112078 A1 | 5/2012 | Millett et al. |
| 2012/0114212 A1 | 5/2012 | King et al. |
| 2012/0129274 A1 | 5/2012 | Prescher et al. |
| 2012/0138804 A1 | 6/2012 | Miyaoka et al. |
| 2012/0148138 A1 | 6/2012 | Faul et al. |
| 2012/0155736 A1 | 6/2012 | Faul et al. |
| 2012/0157829 A1 | 6/2012 | Boyden et al. |
| 2012/0157830 A1 | 6/2012 | Boyden et al. |
| 2012/0193545 A1 | 8/2012 | Tkaczyk et al. |
| 2012/0223236 A1 | 9/2012 | Shah et al. |
| 2012/0235047 A1 | 9/2012 | Lewellen et al. |
| 2012/0241631 A1 | 9/2012 | Overweg et al. |
| 2012/0265050 A1 | 10/2012 | Wang |
| 2012/0271840 A1 | 10/2012 | Vosniak et al. |
| 2012/0290519 A1 | 11/2012 | Fontaine et al. |
| 2013/0009063 A1 | 1/2013 | Henseler et al. |
| 2013/0009066 A1 | 1/2013 | Grazioso et al. |
| 2013/0009267 A1 | 1/2013 | Henseler et al. |
| 2013/0020487 A1 | 1/2013 | Siegel et al. |
| 2013/0028496 A1 | 1/2013 | Panin et al. |
| 2013/0032706 A1 | 2/2013 | Cho |
| 2013/0032721 A1 | 2/2013 | Michel et al. |
| 2013/0032722 A1 | 2/2013 | Szupryczynski et al. |
| 2013/0056640 A1 | 3/2013 | Yvon et al. |
| 2013/0092842 A1 | 4/2013 | Zhang et al. |
| 2013/0131422 A1 | 5/2013 | Vosniak et al. |
| 2013/0131493 A1 | 5/2013 | Wollenweber et al. |
| 2013/0136328 A1 | 5/2013 | Jansen et al. |
| 2013/0149240 A1 | 6/2013 | Lopez et al. |
| 2013/0153774 A1 | 6/2013 | Hughes et al. |
| 2013/0193330 A1 | 8/2013 | Wagadarikar et al. |
| 2013/0240721 A1 | 9/2013 | Laurence et al. |
| 2013/0256536 A1 | 10/2013 | Kim |
| 2013/0256559 A1 | 10/2013 | Wollenweber et al. |
| 2013/0284936 A1 | 10/2013 | McBroom et al. |
| 2013/0310681 A1 | 11/2013 | Schulz et al. |
| 2013/0315454 A1 | 11/2013 | Laurence et al. |
| 2013/0320218 A1 | 12/2013 | Woldemichael |
| 2013/0327932 A1 | 12/2013 | Kim et al. |
| 2013/0334428 A1 | 12/2013 | Kim et al. |
| 2013/0341518 A1 | 12/2013 | Fries et al. |
| 2014/0003689 A1 | 1/2014 | Asma et al. |
| 2014/0008542 A1 | 1/2014 | Olcott et al. |
| 2014/0021354 A1 | 1/2014 | Gagnon et al. |
| 2014/0021356 A1 | 1/2014 | Zwaans et al. |
| 2014/0029715 A1 | 1/2014 | Hansen et al. |
| 2014/0048716 A1 | 2/2014 | Solf |
| 2014/0062486 A1 | 3/2014 | Overweg et al. |
| 2014/0064585 A1 | 3/2014 | Wollenweber |
| 2014/0079304 A1 | 3/2014 | Foo et al. |
| 2014/0110592 A1 | 4/2014 | Nelson et al. |
| 2014/0175294 A1 | 6/2014 | Frach |
| 2014/0175296 A1 | 6/2014 | Benlloch Baviera et al. |
| 2014/0183369 A1 | 7/2014 | Frisch et al. |
| 2014/0194735 A1 | 7/2014 | Panin |
| 2014/0200848 A1 | 7/2014 | Panin et al. |
| 2014/0203180 A1 | 7/2014 | Goertzen |
| 2014/0206983 A1 | 7/2014 | Schulz et al. |
| 2014/0224963 A1 | 8/2014 | Guo et al. |
| 2014/0246594 A1 | 9/2014 | Pichler et al. |
| 2014/0257096 A1 | 9/2014 | Prevrhal et al. |
| 2014/0271436 A1 | 9/2014 | Quinton et al. |
| 2014/0275965 A1 | 9/2014 | Majewski et al. |
| 2014/0276018 A1 | 9/2014 | Mukdadi et al. |
| 2014/0276019 A1 | 9/2014 | Majewski et al. |
| 2014/0276029 A1 | 9/2014 | Wollenweber et al. |
| 2014/0316258 A1 | 10/2014 | Hahn et al. |
| 2014/0330117 A1 | 11/2014 | Mann |

(56) References Cited

U.S. PATENT DOCUMENTS

| | | |
|---|---|---|
| 2014/0334702 A1 | 11/2014 | El Fakhri et al. |
| 2014/0336987 A1 | 11/2014 | Frach et al. |
| 2014/0367577 A1 | 12/2014 | Badawi et al. |
| 2015/0001399 A1 | 1/2015 | Fries et al. |
| 2015/0001402 A1 | 1/2015 | Michel et al. |
| 2015/0001403 A1 | 1/2015 | Kim et al. |
| 2015/0021488 A1 | 1/2015 | Stearns |
| 2015/0036789 A1 | 2/2015 | Panin et al. |
| 2015/0057535 A1 | 2/2015 | Sitek |
| 2015/0065854 A1 | 3/2015 | Ahn et al. |
| 2015/0076357 A1 | 3/2015 | Frach |
| 2015/0090890 A1 | 4/2015 | Deller et al. |
| 2015/0117733 A1 | 4/2015 | Manjeshwar et al. |
| 2015/0119704 A1 | 4/2015 | Roth et al. |
| 2015/0160353 A1 | 6/2015 | Wang et al. |
| 2015/0177386 A1 | 6/2015 | Griesmer et al. |
| 2015/0192685 A1 | 7/2015 | Griesmer et al. |
| 2015/0199302 A1 | 7/2015 | Qi et al. |
| 2015/0212216 A1 | 7/2015 | Van Zuiden et al. |
| 2015/0219771 A1 | 8/2015 | Kim et al. |
| 2015/0262389 A1 | 9/2015 | Li et al. |
| 2015/0285921 A1 | 10/2015 | Shah et al. |
| 2015/0285922 A1 | 10/2015 | Mintzer et al. |
| 2015/0289825 A1 | 10/2015 | Lage et al. |
| 2015/0307583 A1 | 10/2015 | Strittmatter |
| 2015/0323685 A1 | 11/2015 | Nelson et al. |
| 2015/0331115 A1 | 11/2015 | Nelson et al. |
| 2015/0355347 A1 | 12/2015 | Pratx |
| 2015/0370223 A1 | 12/2015 | Mann |
| 2015/0374318 A1 | 12/2015 | Koch et al. |
| 2015/0378035 A1 | 12/2015 | Choi et al. |
| 2015/0380121 A1 | 12/2015 | Beekman |

FOREIGN PATENT DOCUMENTS

| | | |
|---|---|---|
| EP | 0610422 A1 | 8/1994 |
| EP | 1875273 A2 | 1/2008 |
| EP | 2360493 A1 | 8/2011 |
| EP | 2643709 A2 | 10/2013 |
| EP | 2707751 A2 | 3/2014 |
| EP | 2707752 A1 | 3/2014 |
| EP | 2733189 A1 | 5/2014 |
| WO | WO9309447 | 5/1993 |
| WO | WO9706451 | 2/1997 |
| WO | WO0214904 | 2/2002 |
| WO | WO2009018321 A2 | 2/2009 |
| WO | WO2009154340 A1 | 12/2009 |
| WO | WO2011008119 A2 | 1/2011 |
| WO | WO2011117316 A2 | 9/2011 |
| WO | WO2012034178 A1 | 3/2012 |
| WO | WO2012135725 A2 | 10/2012 |
| WO | WO2012152587 A2 | 11/2012 |
| WO | WO2012153223 A1 | 11/2012 |
| WO | WO2013152434 A2 | 10/2013 |
| WO | WO2014001926 A1 | 1/2014 |
| WO | WO2014012182 A1 | 1/2014 |
| WO | WO2014020471 A2 | 2/2014 |
| WO | WO2014135465 A1 | 9/2014 |

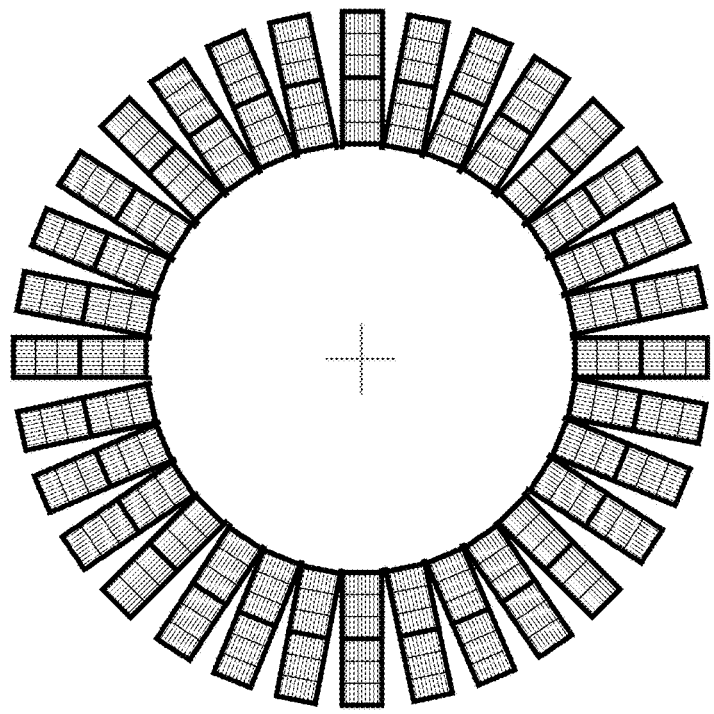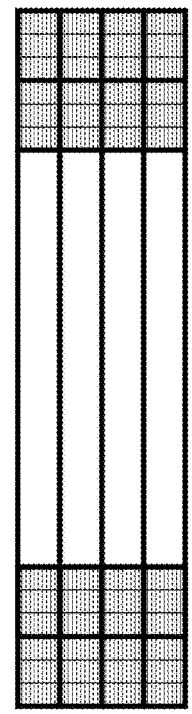
Fig. 4A    Fig. 4B
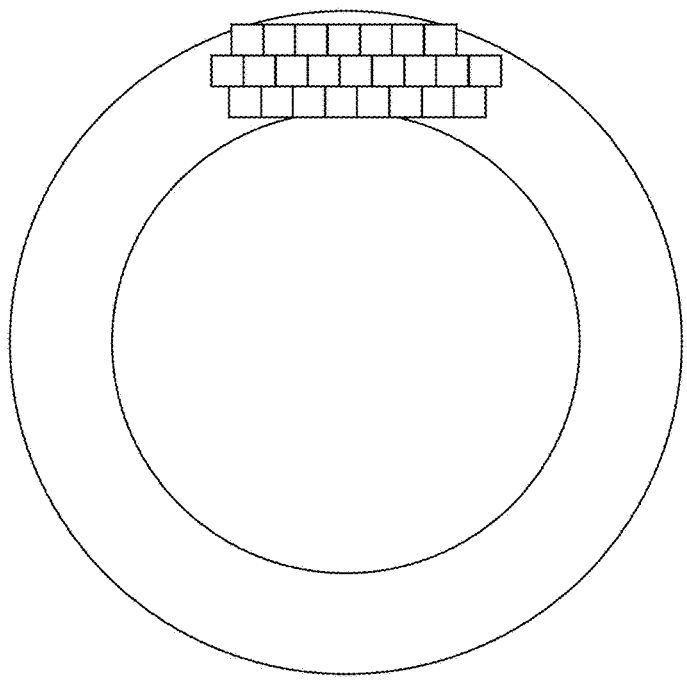
Fig. 5

AUTONOMOUS GAMMA, X-RAY, AND PARTICLE DETECTOR

CROSS REFERENCE TO RELATED APPLICATIONS

The present application is a Continuation under 35 U.S.C. §120 of U.S. patent application Ser. No. 15/080,073, filed Mar. 24, 2016, now U.S. Pat. No. 9,606,245, issued Mar. 28, 2017, which is a non-provisional of, and claims benefit of priority under 35 U.S.C. §119(e) from, U.S. Provisional Patent Application No. 62/137,276, filed Mar. 24, 2015, the entirety of which are expressly incorporated herein by reference.

FIELD OF THE INVENTION

The present invention relate to the field of scintillation detector arrays.

BACKGROUND OF THE INVENTION

Positron Emission Tomography (PET) is a proven and powerful research and clinical tool that uses molecular biomarkers for imaging the function and metabolism of the human body and brain. These biomarkers can be tailored to a high degree of specificity to highlight abnormal metabolism and uptake and are often used to diagnose diseases such as brain tumor, strokes, neuron-damaging disease (dementia), and other neurological disorders (addiction, schizophrenia, etc.). However, it suffers a number of critical limitations that restrict its full research and clinical potential.

The inability to rapidly diagnosis non-penetrating Traumatic Brain Injury (TBI) especially in its mild form (mTBI) has very significant implications for military operations, and for the health and health care costs of TBI victims. Detection of TBI is difficult as symptoms can be slow to develop and are difficult to recognize. Premature return to duty of an effected individual could seriously impact on his/her performance, and delayed medical treatment exacerbates an individual's acute and chronic medical condition.

Present human brain PET scanners are large, heavy, and fragile with ring geometries and hence are of low sensitivity. They have low and non-uniform spatial resolution and very poor temporal resolution. None of them allows imaging of a freely moving subject‡ [31, 32], only one of them allows imaging in a sitting position (PET-Hat)[33]. Other all require subjects to be lying on a scanner bed. This restriction limits the use of PET brain mapping in studies of, for example, bipolar disorder [34-46], psychosis, schizophrenia, autism, dementia, glutamate levels, obesity [47-50], gambling [51], video game addiction [52], and chronic fatigue syndrome [53-55]. Additionally, all conventional PET devices are sensitive to environmental factors (temperature gradients, vibrations, etc.).

U.S. Pat. No. 7,884,331, expressly incorporated herein by reference, provides a brain imager which includes a compact ring-like static PET imager mounted in a helmet-like structure, as shown in FIG. 8. When attached to a patient's head, the helmet-like brain imager maintains the relative head-to-imager geometry fixed through the whole imaging procedure. The brain imaging helmet contains radiation sensors and minimal front-end electronics. A flexible mechanical suspension/harness system supports the weight of the helmet thereby allowing for patient to have limited movements of the head during imaging scans. The compact ring-like PET imager enables very high resolution imaging of neurological brain functions, cancer, and effects of trauma using a rather simple mobile scanner with limited space needs for use and storage. This system provides a ring of detectors, in a single layer, in a non-wearable helmet (suspended by a cable), and is not conformable or adapted to form arbitrary 3D shaped arrays, and does not provide depth of interaction information.

The Stanford University Molecular Imaging Instrumentation Laboratory developed a scintillation light detection system for PET. The system is constructed with basic block detector modules, for clinical or pre-clinical (small animal) PET systems and breast-dedicated PET system. The module is in the form of many detector layers. Each layer comprises two adjacently situated planar arrays of $1 \times 1 \times 1$ mm$^3$ lutetium-yttrium-oxyorthosilicate (LYSO) scintillation crystals coupled to two specially designed, planar and extremely thin (200 micron) position-sensitive avalanche photodiodes (PSAPD), each with a $8 \times 8$ mm$^2$ sensitive area. Alternating layers of planar crystal arrays and flat PSAPD detectors, coupled together, are configured "edge-on" with respect to incoming photons. The PSAPD has both high light sensitivity and an intrinsic resolution that is finer than 1 mm, the selected width of the LYSO crystals. The PSAPD generates large electronic signals and allows the precise positioning of the light flashes resulting from the absorption of a 511 keV in any crystal; the resolution of each LSO-PSAPD compound layer in any direction is determined primarily by the 1-mm individual crystal dimension. The PSAPDs replace the photomultiplier tubes (PMT) used in standard PET designs. The PSAPD reads the crystals from their relatively large side faces, rather than from their tiny end faces for better scintillation light collection efficiency and directly-measured photon interaction depth. This approach allows high efficiency light extraction from the long and thin scintillation crystals; with light collection efficiency >95%. Light collection per event is largely independent of crystal length or surface treatment, and of location within a crystal of the point of light creation. Coincidence detection efficiency (i.e., fraction of emitted coincident 511 keV photon counts collected from a given probe concentration) is increased by bringing the detectors closer to the subject and by using thicker scintillation crystal material (2 cm effective thickness proposed vs. 1 cm standard for small animal imaging). Spatial resolution is enhanced by using finer scintillation crystals (1 mm vs. 1.5-6.0 mm standard). Uniformity of spatial resolution improves by direct measurement of the photon interaction depth within the crystals using the side-coupled PSAPDs; this depth measurement reduces position-dependent parallax positioning errors (hence loss of resolution) due to photon penetration into crystals. Standard PET system detectors are incapable of this photon interaction depth resolution. See, miil.stanford.edu/research/scintillationlightdetection.html; miil.stanford.edu/publications/files/39_PUB.pdf; 29_PUB.pdf; 24_PUB.pdf; 14_PUB.pdf; 142_PUB.pdf; 183_PUB.pdf; 147_PUB.pdf; 52_PUB.pdf; 181_PUB.pdf; each of which is expressly incorporated herein by reference. U.S. Pat. No. 8,373,132, expressly incorporated herein by reference, relates to a radiation detector with a stack of scintillator elements and photodiode arrays. The detector comprises a stack of the scintillator elements and photodiode arrays (PDA). The PDAs extend with electrical leads into a rigid body filling a border volume lateral of the scintillator elements, wherein said leads end in a contact surface of the border volume. Moreover, a redistribution layer is disposed on the contact surface, wherein electrical lines of the redistribution layer contact the leads of the PDAs.

US 20110240864, expressly incorporated herein by reference, discloses an autonomous detector module as a building block for scalable PET and SPECT systems. When detecting scintillation events in a nuclear imaging system, time-stamping and energy-gating processing is incorporated into autonomous detection modules (ADM) to reduce downstream processing. Each ADM is removably coupled to a detector fixture, and comprises a scintillation crystal array and associated light detect or (s), such as a silicon photomultiplier or the like. The light detector(s) is coupled to a processing module in or on the ADM, which performs the energy gating and time-stamping.

SynchroPET (Long Island, N.Y.) is seeking to commercialize a portable, small-scale brain-imaging device invented at the U.S. Department of Energy's Brookhaven National Laboratory. (Justin Eure, Groundbreaking Portable PET Scanner Moves Closer to Market, Medical Applications, PHYS.ORG, Jan. 27, 2012 phys.org/news/2012-01-groundbreaking-portable-pet-scanner-closer.html.). The mini PET scanner is intended to be integrated with an MRI. It also has been worn like a collar by fully conscious, active rats. (Miniature "Wearable" PET Scanner Ready for Use, BROOKHAVEN NATIONAL LABORATORY, Mar. 13, 2011 www.bnl.gov/newsroom/news.php?a=11235.) This miniature PET scanner seeks to integrate all the electronics for each detector in the ring on a single, specialized chip, using an avalanche photodiode. (24 Katherine Bourzac, Wearable Scanner Opens New Frontier in Neuroscience, MIT TECHNOLOGY REVIEW, Mar. 17, 2011, m.technologyreview.com/biomedicine/35127/.)

U.S. Pat. No. 7,286,867, expressly incorporated herein by reference, directed to the SynchroPET device provides a combined PET/MRI scanner generally includes a magnet for producing a magnetic field suitable for magnetic resonance imaging, a radiofrequency (RF) coil disposed within the magnetic field produced by the magnet and a ring tomograph disposed within the magnetic field produced by the magnet. The ring tomograph includes a scintillator layer for outputting at least one photon in response to an annihilation event, a detection array coupled to the scintillator layer for detecting the at least one photon outputted by the scintillator layer and for outputting a detection signal in response to the detected photon and a front-end electronic array coupled to the detection array for receiving the detection signal, wherein the front-end array has a preamplifier and a shaper network for conditioning the detection signal. One embodiment of this technology comprises a 4×8 array of LSO crystals of about 2 mm×2 mm square area and 10 mm depth. Another embodiment includes a 5 mm thick LSO scintillator array for better spatial resolution. However, the spatial resolution is still only 2.5 mm to 1.9 mm, respectively. Although this patent describes that freedom of movement is available to the animal, its appears to require a suspension system.

Another company working in the portable PET scanner space is the Brain Biosciences. (Wayne Forrest, Start-up Brain Biosciences Advances Compact PET Scanner, AUNTMINNIE.COM, Jan. 23, 2014 www.auntminnie.com/index.aspx?sec=ser&sub=def&pag=dis&ItemID=106270.) which developed the CerePET, a portable PET scanner for neuroimaging. The prototype is approximately 50 lbs. and can be carried from room to room. The device features crystals made from lutetium yttrium orthosilicate (LYSO) technology, a bore diameter of 25 cm, and 20-cm axial field-of-view. However, the device is not wearable. The scanner has a head support system that fits on a standard examination bed. Preclinical work with phantoms showed that the system is capable of spatial resolution of 2 mm to 3 mm across the field-of-view, energy resolution of less than 13% for all detector blocks, and more than 15% image uniformity. Quantitative accuracy was also better than 10% after calculating attenuation correction.

WO 2012/034178, expressly incorporated herein by reference, provides a radiation detector is disclosed that comprises a scintillator that emits electromagnetic radiation in response to excitation by radiation of interest, and a photodetector with a semiconductor active layer adapted to interact with the electromagnetic radiation and a substrate. Either the scintillator constitutes the substrate or the substrate is located such that the substrate is between said active layer and the scintillator, and the substrate is at least partially transparent to the electromagnetic radiation.

U.S. Pat. No. 8,071,949, expressly incorporated herein by reference, provides a compact, mobile, dedicated SPECT brain imager that can be easily moved to the patient to provide in-situ imaging, especially when the patient cannot be moved to the Nuclear Medicine imaging center. As a result of the widespread availability of single photon labeled biomarkers, the SPECT brain imager can be used in many locations, including remote locations away from medical centers. The SPECT imager improves the detection of gamma emission from the patient's head and neck area with a large field of view. Two identical lightweight gamma imaging detector heads are mounted to a rotating gantry and precisely mechanically co-registered to each other at 180 degrees. A unique imaging algorithm combines the co-registered images from the detector heads and provides several SPECT tomographic reconstructions of the imaged object thereby improving the diagnostic quality especially in the case of imaging requiring higher spatial resolution and sensitivity at the same time.

U.S. Pat. No. 7,554,089, expressly incorporated herein by reference, provides a method for localizing optical emission is disclosed. The method involves identifying a first readout channel of a first pixellated photodetector array based on an impact of a first photon on the first pixellated photodetector array. The first photon is emitted by a scintillator unit of a scintillator array and the first readout channel corresponds to a column of one or more pixels of the first pixellated photodetector array. The method also involves identifying a second readout channel of a second pixellated photodetector array based on an impact of a second photon on the second pixellated photodetector array. The second photon is emitted by the scintillator unit and the second readout channel corresponds to a row of one or more pixels of the second pixellated photodetector array. The method further involves identifying the scintillator unit based on the first readout channel and the second readout channel.

US 2013/0153774, expressly incorporated herein by reference, provides apixellated scintillator readout arrangement is presented, the arrangement comprising a plurality of scintillator pixels arranged in a scintillator array, and a plurality of photodetectors arranged to receive light from, or address, the scintillator pixels. The photodetectors may be arranged on both a first side and a second side of the scintillator array. Each photodetector may be arranged to leave a gap adjacent to the scintillator pixel which is addressed by that photodetector. Non-photosensitive elements such as tracking and bondpads may be arranged in at least some of the gaps. Electronic components such as electronic amplifiers may be arranged in at least some of the gaps. The photodetectors may be arranged in linear arrays addressing alternate lines of scintillator pixels on either side of the scintillator array. Each photodetector may be arranged to address a single pixel (as illustrated) or more than one pixel.

U.S. Pat. No. 7,956,331, expressly incorporated herein by reference, provides scintillation detectors capable of detecting the position or depth of gamma photon interactions occurring within a scintillator, thereby improving the resolution of ring based positron emission tomography (PET) imaging systems. In one embodiment, the technology is directed to a scintillation detector that comprises at least one pair of side-by-side conjunct scintillation crystal bars having a shared interface between, and a solid-state semiconductor photodetector optically coupled to each output window of each individual scintillation crystal bar. The solid-state semiconductor photodetector includes an array of discrete sensitive areas disposed across a top surface of a common substrate, wherein each sensitive area contains an array of discrete micro-pixelated avalanche photodiodes, and wherein the output window of each scintillation crystal bar is optically coupled to each respective sensitive area in a one-on-one relationship. This patent describes scintillation detectors capable of detecting the position or depth of gamma photon interactions occurring within a scintillator. At least one pair of conjunct scintillation crystal bars may be provided, wherein each pair of conjunct scintillation crystal bars is composed of two individual optically coupled scintillation crystal bars positioned in a side-by-side relationship. The scintillation detector also includes a solid-state semiconductor photodetector.

WO 2012152587, expressly incorporated herein by reference, provides a Gamma Detector which comprises a scintillation crystal block and a set of Geiger-mode Avalanche Photodiode (G-APD) sensor elements optically coupled to at least a first surface of the scintillation crystal block. The G-APD sensor elements are arranged in at least one elongate strip of G-APD sensor elements, said G-APD strip coupled to a readout circuit.

The emission of the scintillator must be detected with an energy resolution sufficient to distinguish the 511 keV primary events from scattering events and with timing resolution to enable coincidence windowing. For a PET scanner, the requirements also include size and scalability, operation in high magnetic fields for multimodality imaging, and cost; these pose substantial challenges to the system design[63]. Photomultiplier have traditionally been used as they provide high gain (106) with fast response and low noise, can be fabricated as arrays for segmented detection, and are relatively low cost. However, the physical size limits use of PMT based detectors in applications where detector volume and mass must be minimized, and they cannot operate in high magnetic fields for MRI.

Solid state detectors address many of the limitations of PMTs and numerous configurations have been reported. One approach is direct conversion and detection, as recently demonstrated in CdTe Schottky barrier detectors in 4×4×2 mm crystals [64]. However, all direct conversion techniques require high voltage and are difficult to scale to large arrays. Consequently, the majority of solid-state detectors utilize a scintillator crystal coupled to the thin film photon detection sensors (TFPDS), primarily Si PIN diodes, avalanche photodiodes (APD), and Geiger-mode avalanche photodiodes (G-APD). State of the art Si-based solid state photon detectors were reviewed in 2009 by Renker and Lorentz [65]. For PET applications, G-APD detectors show the greatest promise as they provide the energy resolution, speed, and integration level required for normal and time-of-flight detection. Arrays of G-APDs can be fabricated over relatively large areas (1×1 cm), as demonstrated by Radiation Monitoring Devices [rmdinc.com/solid-state-photo-multipliers-for-pet/]. Further, coupled with a LaBr$_3$:Ce scintillator, timing resolution to 100 ps has been demonstrated providing potential for time-of-flight enhancements to image reconstruction [66].

Table 2 provides incomplete list of scintillators suitable for PET scanners [58-62]. NaI(T1) has been used in PET designs in the past in view of its brighter response, low cost and good energy resolution. However, its slow response and low-gamma ray stopping efficiency limit its performance in PET. Europium doped strontium iodide (SrI2:Eu) has very high light output and excellent energy resolution for gamma detection, but rather slow response due to high decay time constant. LSO and LYSO are used in PET instrumentation due to their high gamma ray stopping power. Still, energy resolution of LSO is variable and is limited by its non-proportionality (self-absorption). Furthermore, LSO is optically anisotropic, and it cannot be made fully transparent. Lutetium-yttrium orthosilicate (LYSO) is a variant of LSO in which some of the lutetium is replaced by yttrium atoms and is currently the scintillator of choice for PET application. The yttrium component makes LYSO easier and cheaper to grow (low temperature crystal growth), and the light loss from self-absorption is lower in LYSO. Due to the presence of Lu-176 isotope, LSO/LYSO crystals are themselves radioactive and produce scintillation light. Lu-176 is a β-emitter primarily decaying to an excited state of Hf-176, which then emits gamma photons with energies of 307 keV, 202 keV, and 88 keV [61]. Lanthanum bromide LaBr$_3$:Ce crystals have the advantages of very high light output (~3× of LYSO), fast decay time affording excellent time resolution, excellent energy resolution (<3% at 662 keV), thus providing improved ability for rejection of scattered events and random coincidences, and low melting point (783° C., compared to 2047° C. for LYSO) offering easier crystal growth at lower cost.

In a PET system the ultimate goal is to produce a high fidelity image of the radionuclide distribution within the imaged object. There are three fundamental mechanisms that contribute to the quality of PET images: system sensitivity, noise, and spatio-temporal localization. [59]. The first two quantities are well accounted for in the data via the noise equivalent counts (NEC) [170]. All other things being equal the system with the better NEC will produce better images. Spatio-temporal localization is the system's basic ability to identify the spatio-temporal coordinates of the detected gamma photons (counts) and the necessary sampling to project them into the spatial domain (i.e. image reconstruction). It should be emphasized that this act of projecting the detected gamma photons into the spatial domain, the image reconstruction, is critical to achieving a high quality images even if it is not necessarily a part of the main system design process. We also note that improved localization (e.g. time-of-flight information) improves the effective NEC [171].

Image quality is directly related to the effective NEC collected during an acquisition, which includes improved noise rejection from time-of-flight (TOF) information [171]. It is defined by the relation, $$NEC_{\mathit{eff}} = \left(\frac{D}{\min(c\Delta t/2, D)}\right)\left(\frac{T+S+(D/D_{FOV})R}{T+S+(D/D_{FOV})^2 R}\right)NEC$$

$$= \left(\frac{D}{\min(c\Delta t/2, D)}\right)\left(\frac{T+S+(D/D_{FOV})R}{T+S+(D/D_{FOV})^2 R}\right)\frac{T^2}{T+S+R}$$

where T, R, and S are true, random, and scatter counts respectively, and cΔt/2 represents the TOF photon localization, D is the mean head diameter, and D$_{FOV}$ is the diameter of the field-of-view (FOV). Clearly improved TOF for a given source geometry always improves the NEC.

To maximize the NEC for a particular activity distribution within the FOV a number of issues must be considered. They include geometric and attenuation sensitivity, detector dead time, source attenuation, sensitivity, and additive noise from random and scatter counts (and cascade with some isotopes). The geometric and attenuation sensitivity are defined by the device geometry, and the scintillator attenuation and thickness. On the other hand, dead time is dependent on the incident photon flux and the detector electronics. In general, the source's attenuation loss is patient dependent and cannot easily be included in the design consideration, however in the case of brain imaging, patient head size variability is smaller than variability of body habitus. Thus, its effects on sensitivity can be considered in the system's design.

The geometric sensitivity is defined by the effective solid angle of a point in the FOV and the detector scintillator. Because PET is based on coincidence detection, the geometric sensitivity is defined as $4\pi$ srd minus the solid angle subtended by the point to the non-detector area or opening and its back projection [172]. For systems with more than one opening care must be taken to avoid double counting any overlap between various solid angles and back projections. It follows that for spherical caps and cylindrical geometries the poorest geometric sensitivity in any particular slice is on the system's central axis. Detector attenuation sensitivity is defined by the system geometry and for a system with identical detectors it is can be well approximated by a constant.

The intrinsic resolution is largely a function of detection localization, and source uncertainty. The one aspect of detection localization is the system geometry, which is essentially determined by the solid angle coverage of the FOV and provides the available oversampling. It provides the overall detector framework and the subdivision of the detector elements into groups or blocks. Within this framework the light sharing and inter-detector Compton scatter define the ability of the detector to localize a particular detection event. These phenomena provide the detector's contribution to the overall system PSF [60]. In addition, depth of interaction (DOI) for off-center events can result in resolution loss for the system. The intrinsic source uncertainty is isotope dependent and arises from positron transport (decay location uncertainty, positron range) and residual momentum in the annihilation process (annihilation location uncertainty, non-collinearity). These sources of resolution uncertainty are independent and can be added in quadrature giving $$\sigma_{total} = \sqrt{s_{det}^2 + \sigma_{pos,A^Z X}^2 + \sigma_\theta^2 + s_\parallel^2},$$

where $s_{det}$ $s_{det}$, $\sigma_{pos,A^Z X}$, $\sigma_\theta$, and $s_\parallel$ and $s_\parallel$ are FWHM detector, positron range, non-collinearity and DOI uncertainties respectively [59]. We note that the positron range uncertainty is tissue and isotope dependent (density dependence provides a good approximation). The source location uncertainty can be found in the literature or estimated via Monte Carlo.

The detector's position uncertainty can be broken down further into detections via photoelectric and Compton interactions. The number of detected events for each type of interaction depends on their respective cross-section ratios for the particular interaction. In the case of the ADA system described here, where there is no light sharing; the uncertainty of detection via photoelectric effect (and correctly identified points of first interaction for Compton interactions) can be well approximated by the detector sampling distance because the range of the photoelectrons is very small, as compared to the size of scintillator crystals. The position uncertainty is limited by sampling and is $s_{det}^2 = s_{PE}^2 = (d/2)^2$, where d is the scintillator crystal width.

The effect of Compton scatter on resolution is more difficult to estimate and it cannot simply be added in quadrature to the sampling uncertainty. Nonetheless, it does contribute to the system point spread function. The uncertainty induced by Compton scatter is given by $s_c = \sqrt{\bar{x}_c^2 + d^2/2}$, where the ½ term results from sampling and $\bar{x}_c$, is the mean-free-path of a 511 keV photon in the scintillator. The mean Compton path length can be derived and calculated via the integral $$\bar{x}_c = \int_0^\pi p_{511}(\theta) \frac{\sin\theta}{\rho\left(\frac{\mu}{\rho}\right)_E} d\theta,$$

where $p_{511}(\theta)$ is the probability of a particular scattering angle for incident 511 keV photons using Klein-Nishina cross sections, the sine term is a forward scattering correction, and $\bar{x}_{mfp} = 1/\rho(\mu/\rho)_E$ is the mean free path for a photon at a particular energy, which in this case is given by the Compton energy loss, $E = -0.511/(2-\cos\theta)$.

In a multi-layered detector design, where individual detector elements cannot localize events, some DOI resolution loss will exist. The uncompensated loss for scintillators within blocks can be described by $s_\parallel = (\bar{x}_{mfp}/2) \times (r\sqrt{R^2 - r^2}/R^2)$, where r and R are the radial offset and system radius respectively. The factor of ½ is due to detector penetration likelihood at both ends of the line of response.

Depth of interaction correction can be accomplished by a number of means including position sensitive detectors and stacked detectors. In either case the resolution loss is mitigated by reducing the penetration depth effect. In the case of the stacked detector block the achievable FWHM resolution as a function of thickness results in the following relationship, $$\sigma_{total}(t) = \sqrt{s_{det}^2 + \sigma_{pos,A^Z X}^2 + \sigma_\theta^2 + \left(\frac{\min(t, \bar{x}_{mfp})r\sqrt{R^2 - r^2}}{2R^2}\right)^2}$$

Note that the thickness must be less than the mean-free-path length of the photon in the scintillator.

See, U.S. Patent and U.S. Pat. Nos. 4,395,635; 4,415,807; 4,559,597; 4,864,140; 4,980,552; 5,241,181; 5,252,830; 5,272,343; 5,272,344; 5,300,782; 5,323,006; 5,331,553; 5,378,893; 5,424,946; 5,519,221; 5,543,622; 5,602,395; 5,608,221; 5,625,190; 5,751,000; 5,834,779; 5,841,140; 5,900,636; 5,965,891; 5,990,482; 5,998,793; 5,999,588; 6,008,493; 6,072,177; 6,100,531; 6,194,728; 6,215,903; 6,229,145; 6,232,604; 6,239,438; 6,255,655; 6,297,506;

6,310,349; 6,362,478; 6,373,059; 6,410,919; 6,410,920; 6,462,342; 6,509,565; 6,521,893; 6,525,322; 6,525,323; 6,545,280; 6,552,348; 6,590,213; 6,590,215; 6,593,575; 6,603,125; 6,624,422; 6,628,984; 6,670,614; 6,723,993; 6,740,882; 6,803,579; 6,852,978; 6,858,850; 6,936,822; 7,016,458; 7,026,621; 7,030,382; 7,038,212; 7,084,403; 7,085,405; 7,088,901; 7,091,489; 7,102,134; 7,102,135; 7,115,874; 7,115,875; 7,126,126; 7,129,496; 7,129,497; 7,132,664; 7,141,794; 7,180,074; 7,202,477; 7,211,799; 7,217,928; 7,227,149; 7,286,867; 7,301,144; 7,304,309; 7,324,624; 7,332,721; 7,345,281; 7,352,840; 7,359,535; 7,365,333; 7,381,958; 7,381,959; 7,394,053; 7,405,405; 7,412,280; 7,447,345; 7,465,927; 7,489,799; 7,507,968; 7,519,412; 7,557,351; 7,576,329; 7,579,599; 7,605,373; 7,626,389; 7,638,771; 7,667,199; 7,667,457; 7,671,339; 7,684,589; 7,700,003; 7,705,314; 7,723,694; 7,737,404; 7,755,054; 7,756,310; 7,759,625; 7,778,787; 7,791,029; 7,800,070; 7,807,974; 7,818,047; 7,825,384; 7,847,552; 7,945,079; 7,953,265; 7,968,852; 7,983,735; 8,000,513; 8,003,948; 8,014,614; 8,017,902; 8,017,914; 8,068,896; 8,084,742; 8,094,908; 8,098,916; 8,110,805; 8,110,806; 8,144,962; 8,153,983; 8,155,415; 8,164,063; 8,193,815; 8,194,937; 8,204,172; 8,229,199; 8,258,480; 8,269,177; 8,274,054; 8,299,440; 8,304,736; 8,309,932; 8,315,353; 8,334,697; 8,340,377; 8,343,509; 8,350,220; 8,355,551; 8,357,486; 8,369,928; 8,384,037; 8,388,931; 8,395,127; 8,399,848; 8,405,035; 8,410,449; 8,431,904; 8,450,692; 8,450,693; 8,466,419; 8,467,848; 8,472,683; 8,472,688; 8,476,593; 8,476,594; 8,478,015; 8,481,947; 8,488,857; 8,497,484; 8,511,894; 8,525,116; 8,527,034; 8,530,846; 8,532,357; 8,547,100; 8,577,114; 8,598,534; 8,598,536; 8,604,440; 8,604,795; 8,605,988; 8,674,312; 8,698,087; 8,699,771; 8,716,664; 8,716,669; 8,723,521; 8,735,834; 8,735,835; 8,755,586; 8,761,478; 8,767,908; 8,779,366; 8,787,620; 8,796,637; 8,809,790; 8,809,793; 8,816,286; 8,818,488; 8,822,933; 8,822,935; 8,828,355; 8,837,799; 8,866,086; 8,884,240; 8,897,518; 8,903,152; 8,907,290; 8,913,810; 8,921,754; 8,921,796; 8,933,409; 8,933,411; 8,934,959; 8,937,285; 8,941,071; 8,942,445; 8,969,815; 8,969,816; 8,969,829; 8,975,907; 8,987,659; 8,992,918; 9,031,300; 9,044,153; 9,063,520; 9,078,622; 9,091,771; 9,140,804; 9,151,851; 9,155,514; 9,176,240; 9,176,241; 9,182,506; 9,207,334; 9,217,795; 9,229,115; 9,244,180; 9,268,033; 9,279,892; 20010001107; 20010040219; 20010056234; 20020113211; 20020145115; 20020195565; 20030038240; 20030047686; 20030047687; 20030057375; 20030062482; 20030105397; 20030116713; 20040016884; 20040026620; 20040084625; 20040129886; 20040164249; 20040183022; 20040195512; 20040200966; 20040210132; 20040258286; 20040260176; 20050004452; 20050015004; 20050023473; 20050031293; 20050035297; 20050061983; 20050082484; 20050082486; 20050113667; 20050117694; 20050129295; 20050151084; 20050156112; 20050167529; 20050230626; 20050242288; 20050253073; 20050253076; 20050285041; 20060029544; 20060108509; 20060116567; 20060138315; 20060145082; 20060163485; 20060197023; 20060202125; 20060231765; 20060237654; 20060261275; 20070010731; 20070040122; 20070057189; 20070090300; 20070116168; 20070131866; 20070181814; 20070205368; 20070221850; 20070263764; 20070267576; 20070269093; 20070270693; 20070278409; 20080011953; 20080069414; 20080118134; 20080128623; 20080135769; 20080137930; 20080156993; 20080164875; 20080197288; 20080203309; 20080210876; 20080219534; 20080230707; 20080237475; 20080240535; 20080253525; 20080253526; 20080253527; 20080253528; 20080253529; 20080253530; 20080253531; 20080253627; 20080260646; 20080284428; 20090018438; 20090072151; 20090072153; 20090074281; 20090110256; 20090146065; 20090159804; 20090161931; 20090161933; 20090169085; 20090175523; 20090220419; 20090224158; 20090236532; 20090257633; 20090262996; 20090264753; 20090302228; 20100010343; 20100012846; 20100014728; 20100033186; 20100046821; 20100072375; 20100074500; 20100076300; 20100078566; 20100078569; 20100084559; 20100098312; 20100104505; 20100108894; 20100108896; 20100108900; 20100116994; 20100135559; 20100140486; 20100148039; 20100152577; 20100166274; 20100182011; 20100189324; 20100198061; 20100200763; 20100219345; 20100219347; 20100220909; 20100230601; 20100246919; 20100252723; 20100268074; 20100294940; 20110001053; 20110018541; 20110073764; 20110079722; 20110105892; 20110116695; 20110117094; 20110133091; 20110142304; 20110142315; 20110142367; 20110150181; 20110174980; 20110210255; 20110212090; 20110215248; 20110218432; 20110220802; 20110228999; 20110248175; 20110248765; 20110253901; 20110272587; 20110278466; 20110291017; 20110299747; 20110301918; 20120018644; 20120019064; 20120022361; 20120022362; 20120022364; 20120061576; 20120068076; 20120068077; 20120093380; 20120112078; 20120114212; 20120129274; 20120138804; 20120148138; 20120155736; 20120157829; 20120157830; 20120193545; 20120223236; 20120241631; 20120265050; 20120271840; 20120290519; 20130009063; 20130009066; 20130020487; 20130028496; 20130032706; 20130032721; 20130032722; 20130131422; 20130131493; 20130136328; 20130149240; 20130193330; 20130240721; 20130256536; 20130256559; 20130284936; 20130310681; 20130315454; 20130320218; 20130327932; 20130334428; 20130341518; 20140003689; 20140021354; 20140021356; 20140029715; 20140048716; 20140062486; 20140064585; 20140079304; 20140110592; 20140175294; 20140183369; 20140194735; 20140200848; 20140206983; 20140224963; 20140257096; 20140275965; 20140276018; 20140276019; 20140276029; 20140316258; 20140330117; 20140334702; 20140336987; 20140367577; 20150001399; 20150001402; 20150001403; 20150021488; 20150036789; 20150057535; 20150065854; 20150076357; 20150090890; 20150117733; 20150119704; 20150160353; 20150177386; 20150192685; 20150199302; 20150212216; 20150219771; 20150262389; 20150285921; 20150285922; 20150289825; 20150307583; 20150323685; 20150331115; 20150355347; 20150370223; 20150374318; 20150378035; 20150380121; each of which is expressly incorporated herein by reference in its entirety.

TABLE 1

An incomplete list of devices that represents the current state of technology of human brain PET imaging.

| Device name/year | Size/mass/geometry/FOV transaxial/axial | Detector/photo-transducers | Sensitivity kcps/kBq/mL | Spatial resolution Transaxial/axial | Scatter fraction | NEC [kcps] | Energy resolution |
|---|---|---|---|---|---|---|---|
| Hitachi | 2 m × 2 m × 0.5 m/~500 kg/ring 310/250 mm Stationary | CdTe/PMT | 17.6 | 2.3/5.1 mm @ 1 cm 4.8/5.9 mm @ 10 cm | 23% | 41 @ 7.9 kBq/mL | 4.1% |

TABLE 1-continued

An incomplete list of devices that represents the current state of technology of human brain PET imaging.

| Device name/year | Size/mass/geometry/FOV transaxial/axial | Detector/photo-transducers | Sensitivity kcps/kBq/mL | Spatial resolution Transaxial/axial | Scatter fraction | NEC [kcps] | Energy resolution |
|---|---|---|---|---|---|---|---|
| CerePET | 1 m × 1 m × 0.5 m/~23 kg/ring 25/200 mm Portable | LYSO/PMT | N/A | 2.0/2.3 mm @ 1 cm 3.0/? @ 8 cm | N/A | N/A | 13% |
| PET-HAT [33] | Diameter 1 m × 0.25 m/thick/50 kg/280/44 "Wearable" | GSO/PMT | 0.72 | 4/4.3 @ 1 mm | 60%0 | 0.82 | 15% |
| HRRT [56, 57] | dedicated high-resolution 3-dimensional (3D) human brain PET 312/250 | double layer LSO/LYSO/PMT | 39.8 | 2.3/3.2 mm 2.5/3.4 mm | 45% | 45 | |

TABLE 2

Properties of selected scintillators suitable for PET.

| Material | NaI (T1) [58] | SrI$_2$:Eu [59] | LSO:Ce [60, 61] | LYSO:Ce [60, 61] | LaBr$_3$:Ce [62] |
|---|---|---|---|---|---|
| Light Output (photons/MeV) | 38000 | 30000-120000 | 24000 | 25000 | 70000 |
| Principal Decay Time (ns) | 230 | 450-1700 | 40 | 41 | 25 |
| Wavelength of Max. Emission (nm) | 415 | 435 | 420 | 428 | 360 |
| Attenuation Length (511 keV, cm) | 3.3 | 1.95 | 1.2 | 1.16 | 2.4 |
| Density (gm/cc) | 3.67 | 4.55 | 7.4 | 7.3 | 5.0 |
| Energy resolution | 5.6% (662 keV) | 2.8% (662 keV) | 3% (662 keV) | 10% (511 keV) | 3% (511 keV) |
| Scintillators | Ce:Gd$_3$Al$_2$Ga$_3$O$_{12}$ (Ce:GAGG) | Ce:Lu$_{1.8}$Y$_{0.2}$SiO$_5$ (Ce:LYSO) | Bi$_4$Ge$_3$O$_{12}$ (BGO) | Ce:LaBr$_3$ | Lu$_3$Al$_5$O$_{12}$ LuAG |
| Density (g/cm$^3$) | 6.63 | 7.1 | 7.13 | 5.08 | 6.73 |
| Light Yield (photon/MeV) | 57,000 | 34,000 | 8,000 | 75,000 | 22,000 |
| Decay time (ns) | 88 (91%); 258 (9%) | 40 | 300 | 30 | 20 |
| Peak emission (nm) | 520 | 420 | 480 | 375 | 310 |
| Energy Resolution (% @ 662 keV) | 5.2 | 10 | 12 | 2.6 | 4.2 |
| Hygroscopicity | No | No | No | Yes | No |
| Cleavage | No | No | No | No | No |
| Melting point (° C.) | 1,850 | 2,150 | 1,050 | 783 | 2,043 |

SUMMARY OF THE INVENTION

A positron emission tomography (PET) imager is provided for example to acquire Brain PET (BET) to rapidly and reliably screen for TBI at the theater or field levels. BET is based on hardware utilizing solid-state thin film electronics and improved scintillators, and software algorithms that improve image reconstruction. BET provides brain-imaging capabilities not possible with conventional technologies, and are lightweight, small, and less expensive to build, operate, and maintain. BET's γ-detector may be composed of massively parallel thin-film photodetectors (TFPD) and electronics integrated with voxel based scintillators into multiple layers resulting in improved solid angle of collection and depth of interaction resolution. The detector may be helmet shaped, resulting in significantly improved sensitivity and image resolution. BET preferably has one of two configurations: 1) a wearable helmet shaped imager supported by a backpack frame allowing subject mobility, and 2) a fixed but portable version with adjustable tilt (upright to horizontal) and higher sensitivity and image resolution. Both configurations may be low mass, rugged, low-power, low-voltage, ultra-high spatial resolution (~1 mm) and high sensitivity. BET's improved sensitivity translates into smaller amounts of label and less radiation being administered to the subject, reducing operational costs and radiation burden. These systems are easily operated in theater or field level hospitals, emergency departments, and intensive care units (ICU).

A preliminary investigation of the effects of geometry and scintillator material on the performance of a dedicated spherically shaped brain PET (BET) imaging camera shows that a spherical cap provides improved NEC while preserving spatial resolution when compared to an equivalent dedicated cylindrical PET brain camera, and greatly improved PET performance relative to a conventional whole body PET/CT. In addition, the simulations show that LSO will generally outperform LaBr$_3$ for NEC unless the timing resolution is considerably smaller than 300 ps. Furthermore, LaBr$_3$ has a larger Compton scatter fraction that can degrade the system point spread function relative to LSO and contribute to count loss. [173]. The three basic detector geometries investigated were spherical cap, dedicated brain cylinder, and whole body cylinder. The spherical cap BET device extended 120 degrees from the vertical axis and had a radius of 12.5 cm. The cylindrical brain PET (CYL) device had a 25 cm diameter and the same total volume of scintillator for a 10 mm thick scintillator resulting in a height of 22 cm. The whole body (WB) PET system had ring geometry with a 41 cm radius, a 15.8 cm axial field-of-view (FOV), and, because this configuration represented a real PET/CT scanner (GE D690/710), a fixed scintillator thickness of 25 mm. Assuming a 10 and 25 mm thick scintillator for BET and CYL geometry, and 25 mm for WB system the scintillator volumes were ~1,800 ml and ~10,500 ml, respectively.

In a preferred embodiment according to the present technology, a BET system is assembled from distributed Autonomous Detector Arrays (ADAs) integrated into Autonomous Detector Blocks (ADBs). The ADA comprised of an array of small scintillator volumes (voxels with base axa $0.5 \leq a \leq 3.0$ mm, length c: $1.0 \leq c \leq 10$ mm) with 5-65 µm thick reflective layers on its five sides and sixth side optically coupled to the matching array of GAPDs and processing electronics with total thickness of 50 µm. The total thickness of the detector is in the 5-25 mm range. Analytical and Monte Carlo models showed similar results for lower energy window values (458 keV versus 445 keV for LSO, and 492 keV versus 485 keV for $LaBr_3$), and for the relative performance of system sensitivity. Monte Carlo results further showed that the BET geometry had >50% better noise equivalent count (NEC) performance relative to the CYL geometry, and >1100% better performance than a WB geometry for 25 mm thick LSO and $LaBr_3$. For 10 mm thick $LaBr_3$ equivalent mass systems LSO (7 mm thick) performed ~40% higher NEC than $LaBr_3$. Analytic and Monte Carlo simulations also showed that 1×1×3 mm scintillator crystals can achieve ~1.2 mm FWHM spatial resolution.

The BET scanner may have a significant impact on the field of molecular brain imaging. It allows: (1) Rapid determination in emergency department (ED) or en route if patients with wake-up strokes (25% of all strokes) are within the approved time-window for thrombolytic (tPA) treatment. This is a critical issue because presently only 6% of them receives TPA [1]; (2) Patients with severe traumatic brain injury (TBI) who are intensive care unit (ICU) bound are very difficult to evaluate [2] due to the issues associated with moving life-support services to an imaging suite. Typically, MRI is all but impossible [3]. PET has been successfully used to evaluate these patients [4-6] but is logistically complex and resource intensive. A low cost portable BET brain scanner can be used within the ICU to evaluate these patients response stimuli/therapy leading to significant advances in their care; (3) Rapid and accurate determination in ED the damaged brain regions in patients with traumatic brain injury (TBI). Presently, the extent of damage for mild to moderate TBI is difficult to ascertain using CT; (4) Brain PET scans while people move and/or interact naturally with their environment (rather than lying prone) in studies of obesity, gambling, chronic fatigue syndrome, etc.; (5) Brain PET scans of people for whom traditional PET scans may not be feasible (e.g. mania, dementia); (6) Rapid confirmation of brain death—presently very difficult in some cases; (6) 1-mm in vivo spatial resolution vs. 2.5-3.5 mm in conventional brain PET; (7) Feasibility of simultaneous brain PET/MRI without the need for a dedicated very expensive PET/MRI; (8) Lower cost and small mass and size of BET allowing wider implementation of brain PET including ED, ICU and ambulances.

The present technology provides pathways for fabrication of novel autonomous detector voxels, (ADV) and associated systems and methods. A hierarchical integrated autonomous detector array (ADA) and autonomous detector block (ADB) including the ADV is designed to more accurately determine both the spatial location and timing of interaction events sufficient to work in coincidence mode, and energy of photons (e.g. gamma, x-rays) interacting with scintillators.

The present technology provides, for example, an integrated detector and signal/data processing. The photodetectors (APDs), sense amplifiers, energy discriminator, event logging, and communication functions are preferably integrated tightly into the autonomous detector array. The technology may employ silicon APDs, which are compatible with high performance CMOS processing. A small die area devoted to the signal management allows for close integration of the analog detector functions, especially signal integration and event localization. Each block can be segmented to integrated a large number of individual scintillator voxels to the limit of the die area, which today could be as much as 24×36 mm, e.g., a 24×36 array of 1 mm square scintillation crystals, which may be e.g., up to 5 cm tall, and preferably an optimized length which may be, e.g., 2-3 cm long. Integration reduces the signal requirements for an ADA from one analog line per detector to perhaps a simple 3-wire serial communication bus. This dramatically reduces the complexity of integrating the ADAs into higher level functional blocks. With on-chip memory, the speed requirement for the digital serial bus is not critical, since the data from the entire number of events of the entire array over time is typically smaller than the available bandwidth of available serial buses. Under peak conditions, buffering is likely required. The bus is multiplexed, that is, many ADAs communicate over the same bus. At the individual ADA level, the functionality is relatively simple. Segmented detectors on an individual ADA can address event splitting across multiple voxels by summing and reporting a weighted average signal.

The system preferably provides a hierarchical architecture for the signal acquisition and management. The integration of ADAs into the system ADB permits functions of the full detection to be distributed across numerous lower level "elements" with limited local communication between elements. This distributed approach allows for higher functionality of the low level blocks, for example sharing event data across neighboring ADAs to merge events. Only high level "verified" events need to be stored and managed at the higher functional levels.

Photons with energy of 511 keV are of particular interest because they are produced by positron annihilation events used in Positron Emission Tomography (PET) imaging widely used in medical imaging. The technology also has potential application for detection of particles (e.g. alphas, protons, betas, and neutrons). In contrast to existing detectors, the present technology entails a hierarchical detection system based on autonomous detector voxels (ADVs) providing higher spatial resolution than presently achievable. As a hierarchical system, the detectors can be configured flexibly to accommodate system level requirements while minimizing interconnection requirements, power, and environmental constraints.

The detector may be applied to PET where the volumetric detector resolution (in-plane and depth-of-interaction), sensitivity and resilience to environmental factors are key factors establishing the system functionality. We further envision that the autonomous nature of the detector voxels, arrays and blocks allow compact, lightweight, unconventional system geometries, as well as very large thick detector systems using inexpensive plastic scintillators.

The preferred embodiment comprises a dedicated wearable brain PET scanner also imposes requirements of low mass, compact size, and low energy consumption (battery operation or remote RF power is possible).

Scintillation crystals for gamma detectors are disclosed in, for example, U.S. Pat. And U.S. Pat. Nos. 8,062,419; 6,288,399; 20140175296; U.S. Pat. Nos. 8,536,517; 6,624,420; 6,921,901; 7,145,149; 7,749,637; 20130153774;

20050253073; 20110263965; 20140203180; U.S. Pat. No. 8,617,422; 20100327227; U.S. Pat. No. 6,114,703; 20120235047; U.S. Pat. Nos. 6,323,489; 6,449,331; 20140246594; 20140271436; 20040200966; U.S. Pat. Nos. 7,504,634; 8,153,983; 20100012846; as well as EP2733189; EP2707752; WO2012/153223; WO2011/117316; WO2012/152587A2; WO1997006451; WO2013152434, each of which is expressly incorporated herein by reference in its entirety.

Electronic modules including flexible circuits for PET imaging are disclosed in, for example, U.S. Pat. Nos. 8,624,193; 7,193,208; 20120061576; 20070270693; 20110278466; 20130009063; U.S. Pat. Nos. 7,759,650; 7,238,946; 8,269,177; 20070290140; U.S. Pat. No. 8,431,904; 20090072153; U.S. Pat. Nos. 8,716,647; 7,039,227; 8,410,449; 5,821,541; 7,818,047; 20130193330; U.S. Pat. No. 7,342,232; 20130092842; 20140021356, EP0610422; EP1875273; and WO2014135465; each of which is expressly incorporated herein by reference in its entirety.

Photon detectors are disclosed in, for example, 20100084559; 20140175296; U.S. Pat. Nos. 7,193,208; 8,816,286; 7,535,011; 20120061576; 20110240864; U.S. Pat. Nos. 7,737,408; 7,301,153; 5,103,098; 7,385,201; 20110263965; 20150001403; U.S. Pat. No. 8,907,290; 20130009066; 20130009267; 20110192982; U.S. Pat. Nos. 7,759,650; 5,300,782; 20110278466; U.S. Pat. Nos. 7,956,331; 7,884,331; 20140275965; 20120085911; U.S. Pat. No. 8,716,669; 20140008542; U.S. Pat. No. 7,397,038, 20100314546; U.S. Pat. Nos. 8,410,776; 7,329,874; 7,482,593; 8,410,449; 20130056640, WO2014020471; WO1993009447; EP0610422; EP2360493; WO2002014904; EP1875273; CA2492587; WO2009154340; EP2643709; U.S. Pat. No. 8,822,931; WO2012135725; CA2279959; WO2011008119; EP2707751; WO2014012182; WO2014135465; WO2014001926; and WO2009018321, each of which is expressly incorporated herein by reference in its entirety.

It is therefore an object to provide an autonomous scintillation detector comprising: a plurality of scintillator elements arranged in an array; a plurality of detectors, each respective detector being coupled to a respective scintillator element and being configured to selectively detect scintillation of the respective coupled scintillator element; a clock, configured to generate a clock signal having a resolution of less than or equal to 10 nS; circuitry coupled to each of the plurality of detectors and receiving the clock signal, configured to produce a detection event in response to excitation of a respective scintillator element, the detection event comprising a quantitative scintillation parameter and a time of detection; a memory; an interface to the shared addressable digital packet communication network; an automated processor configured to: store a plurality of records representing a plurality of detection events in the memory, each record comprising a respective detection event and an identification of a respective scintillation element associated with the respective detection event; process the stored plurality of records according to at least one filter criteria; transmit the stored records through the shared addressable digital packet communication network; and receive control information through the shared addressable digital packet communication network; and a housing configured to surround at least the plurality of scintillator elements, the plurality of detectors, the clock, the circuitry, the memory, and the automated processor.

The scintillator elements may be scintillation crystals, or other forms of scintillation material. Noncrystalline scintillators have limited transmission of photons, and therefore need the detector to be physically close to all portions of the scintillation medium. However, with highly integrated electronics in thin layers, it is possible to stack a large number of thin scintillation sensor sheets. Such a system might employ technologies used to fabricate flat panel displays/touchscreens, flat panel radiographic sensors, and organic light emitting diode displays. For example, scintillation layers having a thickness of 50-250 micrometers may be layered on a photodiode array, and arranged in a stack of tens or hundreds of layers.

The clock resolution is less than or equal to (better than) 10 nS, and practically, resolution of 1 nS, 100 pS, 10 pS or lower may be provided. A universal time clock is not required, though either internal or external synchronization is required to perform non-real time matching of coincident scintillation event detections.

The filtering is provided as a preferred capability, and is used, for example, to limit the retention and/or transmission of records for detection events outside a reasonable window about 511 kV, the expected positron annihilation energy.

A frame may be provided, configured to support a plurality of autonomous scintillation detectors in a three dimensional array surrounding an object-under-test region.

The plurality of autonomous scintillation detectors may be provided in a sheet array surrounding the object-under-test region, wherein the sheet is deformable and configured to assume a plurality of different non-planar configurations.

The plurality of autonomous scintillation detectors may be provided as plurality of stacked sheet arrays, each sheet array comprising a plurality of the scintillation detectors.

The automated processor may be further configured to compensate the quantitative scintillation parameter for perturbations caused by at least one of temperature and dark current of each detector. The automated processor may receive control instructions from the control system through the network to perform a calibration cycle, for example when a known emission source or phantom is present in the sensing space (positive control), or when no emitter is present (negative control).

The filter criteria may comprise a detected scintillation energy range, the automated processor being further configured to exclude from transmission records associated with detection events having a detected scintillation energy outside a respective detected scintillation energy range. The filter criteria may also comprise a dead time after a detection event, the automated processor being further configured to exclude detection of a subsequent detection event during the dead time.

The automated processor may be further configured to manage a power consumption of the autonomous scintillation detector.

Each scintillation element may comprise a scintillation crystal, and each detector may comprise a thin film photonic detector directly patterned on a surface of each respective scintillation crystal.

The detector may comprise a silicon photonic sensor, and the circuitry may comprise an analog-to-digital converter, a buffer, and clock synchronization and time skew management logic integrated together with the silicon photonic detector.

The automated processor may be further configured to determine positional reference information, to establish spatial coordinates of the autonomous scintillation detector with respect to at least one other autonomous scintillation detector.

The interface to the shared addressable digital packet communication network may comprise an interface to a wireless digital radio frequency communication local area network, such as IEEE-802.11n or ac or ad (WiFi) or IEEE-802.15 (e.g., Bluetooth).

Each scintillator element may be optically and electrically isolated from each other scintillator element of the array.

A further object provides a scintillation detector array comprising a plurality of autonomous scintillation detectors according to claim 1 arranged in a three dimensional distribution about a sensing region, each respective autonomous scintillation detector having the respective automated processor configured to transmit the respective records through a common shared addressable digital packet communication network to a remote server. The three dimensional distribution is configured to surround an upper portion of a human skull, and to be physically supportable by an unconstrained adult human subject.

A still further object provides scintillation detector module, comprising: a clock, configured to produce a clock signal representing a time; a plurality of scintillation crystals, each scintillation crystal being responsive to emissions to produce scintillation events associated with a quantity of photons; a respective detector associated with each of the plurality of scintillation crystals, configured to produce an electrical signal corresponding to the quantity of photons; at least one electronic circuit, configured to receive the electrical signal produced by each respective detector, and to produce a digitized output which preserves at least information comprising the quantity of photons; a digital memory, configured to store a plurality of records, each record comprising at least an identifier of a respective scintillation crystal, a time of a respective a respective emission and the information comprising the quantity of photons association with the respective emission; a digital communication interface, configured to communicate digital information packets through a shared addressable digital packet communication network; and an automated processor, configured to selectively process the information comprising the quantity of photons selectively in dependence on the quantity of photons for each respective scintillation event, transmit the stored plurality of records and receive control information through the digital communication interface.

The system may further comprise a housing which contains the plurality of scintillation elements, the respective detector associated with each of the plurality of scintillation elements, the at least one electronic circuit, the digital memory, the digital communication interface, and the automated processor. The scintillation detector module may be provided in a system along with other such modules and a control system, the control system being configured to: receive the communicated digital information packets through the shared addressable digital packet communication network from each of the scintillation detector module and the at least one additional scintillation detector module; send control information through the shared addressable digital packet communication network to each of the scintillation detector module and the at least one additional scintillation detector module; determine records corresponding to temporally coincident scintillation events from each of the scintillation detector module and the at least one additional scintillation detector module; and generate image information dependent on the determined records.

A scintillation detection method is also provided, comprising: providing a plurality of autonomous scintillation detectors surrounding a space, each autonomous scintillation detector comprising: a plurality of scintillator elements arranged in an array; a plurality of detectors, each respective detector being coupled to a respective scintillator element and being configured to selectively detect scintillation of the respective coupled scintillator element; a clock, configured to generate a clock signal having a resolution of less than or equal to 10 nS; circuitry coupled to each of the plurality of detectors and receiving the clock signal, configured to produce a detection event in response to excitation of a respective scintillator element, the detection event comprising a quantitative scintillation parameter and a time of detection; a memory; an interface to the shared addressable digital packet communication network; an automated processor configured to: store a plurality of records representing a plurality of detection events in the memory, each record comprising a respective detection event and an identification of a respective scintillation element associated with the respective detection event; process the stored plurality of records according to at least one filter criteria; transmit the stored records through the shared addressable digital packet communication network; and receive control information through the shared addressable digital packet communication network; and a housing configured to surround at least the plurality of scintillator elements, the plurality of detectors, the clock, the circuitry, the memory, and the automated processor; receiving the communicated digital information packets through the shared addressable digital packet communication network from plurality of autonomous scintillation detectors; transmitting control information through the shared addressable digital packet communication network to the plurality of autonomous scintillation detectors; determining, records corresponding to temporally coincident scintillation events from each of the scintillation detector module and the at least one additional scintillation detector module; and generating image information dependent on the determined records.

The filter criteria may comprise a detected scintillation energy range, further comprising excluding from transmission by a respective autonomous scintillation detector, records associated with detection events having a detected scintillation energy outside a respective detected scintillation energy range.

BRIEF DESCRIPTION OF THE DRAWINGS

FIGS. 4A and 4B show an end view and side view, respectively, of thirty-two of modules arranged into a 32-fold symmetrical ring of detectors for 10 cm bore small animal PET system composed of the autonomous detector blocks (ADBs) depicted in FIG. 3.

FIG. 5 shows a ring consisting of staggered autonomous detector blocks arranged to maximize sensitivity, spatial resolution, depth of intreraction (DOI), and uniformity. Twenty such rings can be stacked to create a long cylindrical PET system.

DETAILED DESCRIPTION OF THE PREFERRED EMBODIMENTS

The system level technology includes both fabrication of autonomous detector voxels (ADVs) containing thin-film scintillation photon detector (e.g. Geiger mode avalanche photodiode, G-APD) with suitable electronics integrated with appropriate scintillator volume and the integration of these ADVs into autonomous detector arrays (ADAs) or autonomous detector blocks (ADBs) and assembling them into top-system level PET scanner with desired shape and providing the full functionality with desired spatial, temporal and energy resolution and uniformity.

Autonomous Detector Voxel (ADV):

The ADV is comprised of a scintillator, one or more coupled electronics module(s), optically reflecting and isolating surface layers, and electrically isolating coatings. The detection and processing electronics are coupled to or fabricated onto one or more of the scintillator surfaces. The detection electronics contain everything necessary to detect and transmit the data of a scintillation event, including the absorbed energy, timing and scintillator's spatial coordinates. This includes the photodetector, preamplifier, thresholding, pulse shaping, integration, timing, data buffering, communication, and power management. It makes any ADV independent from other surrounding ADVs. The transfer of the basic system electronics from external boards to a substrate that is coupled to or directly on the scintillator volume allows a number of novel configurations that are not possible otherwise. These configurations are discussed further below.

One example of an ADV is as follows: using LYSO as the scintillator, a 10 by 10 by 10 mm LYSO crystal is optically coupled to a thinned silicon chip holding a Geiger-Avalanche Photodiode (G-APD), and the associated electronics encapsulated in a reflective aluminum coating on the sides of the scintillator (see FIG. 1). The G-APD and its associated electronics are embedded in the chip(s). These include the preamplifier, the A/D conversion, energy discrimination, timing, storage cache, communication links, and power system. Each ADV transmits the interaction events and are synchronized via a timing signal. It provides local static positional reference information, to establish the spatial coordinates of each ADV. The data associated with each event is accumulated into local flash or dynamic memory for later transfer and analysis. One embodiment provides integrated control, data collection and preprocessing electronics in the detector, with off-board coincidence circuitry.

Figure 1A:
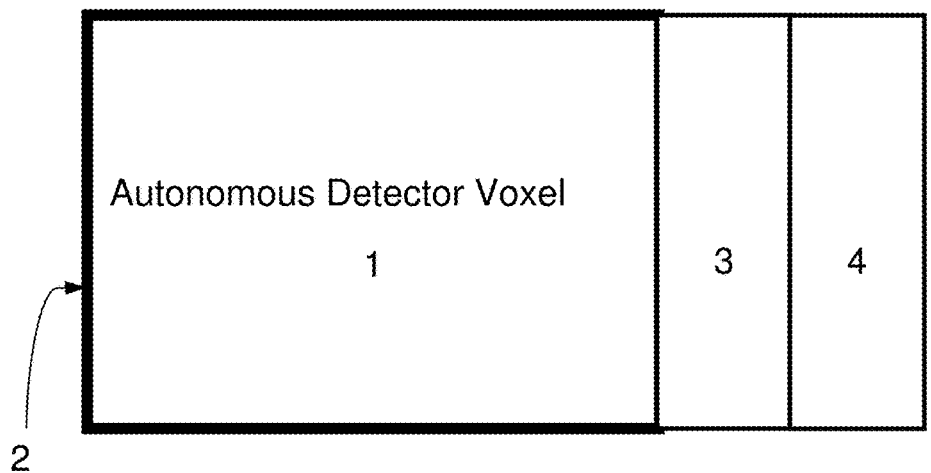
FIGS. 1A and 1B show an individual self-contained autonomous detector voxel (ADV) (FIG. 1A) and a schematic diagram of an integrated photodetection processing system formed on the reverse side of a thin film photon detector (TFPDS) (FIG. 1B).
Figure 1B:
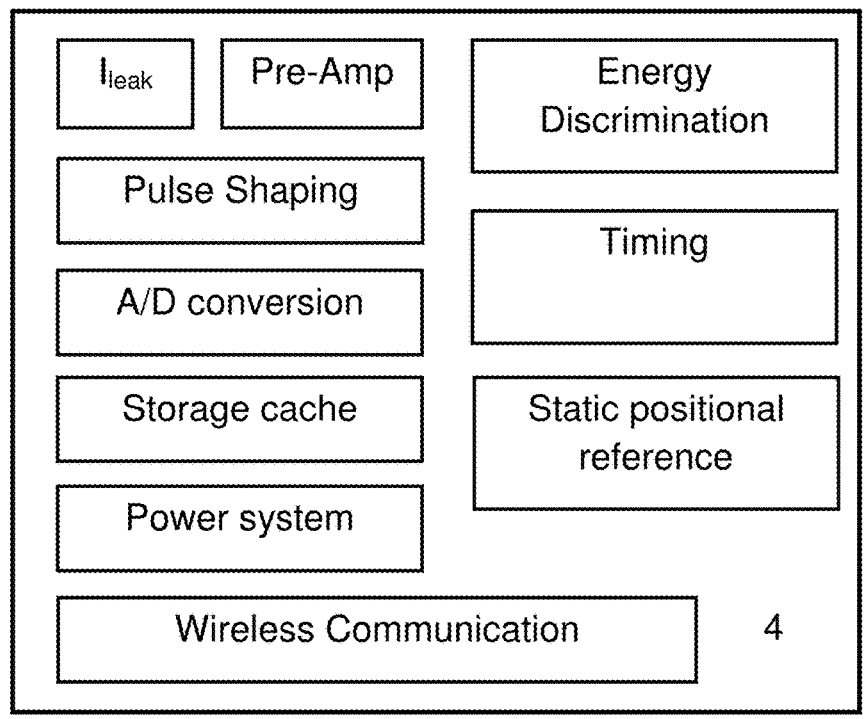

FIG. 1 shows an example of an individual self-contained autonomous detector voxel (ADV): A scintillator volume 1 is provided having optical insulation/reflective and electrical insulation layers 2 surrounding on all sides, except one surface, and on the exposed surface, a thin film scintillation photon detector (e.g. Si G-APD photodiode) module integrated and fitted to the scintillation surface(s). On the reverse side of the thin film scintillation photon detector, integrated electronics 4 are fabricated and connected to the photodetector by a through hole or via(s). It pre-processes event data and transfers them to remote computer node for further processing.

Autonomous Detector Array (ADA):

The ADA represents a plurality of ADVs organized into an array where some of its features are now shared by more than one scintillator element. These may include preamplifier, threshold, pulse shaping, integration, timing, buffer, communication, and power management, thus making the array autonomous rather than the individual voxels. Similar to the case of individual ADVs, the direct coupling of the scintillator to the electronics allows a number of two- and three-dimensional configurations that are not possible otherwise. These configurations are discussed further below.

One example of an ADA as a 2D square lattice is as follows: The autonomous detector blocks (ADB) includes about 300 ADVs, each with a 1 by 1 by 5 mm LYSO scintillator optically coupled to a matching silicon chip holding G-APDs and their associated electronics and encapsulated in a reflective aluminum coating. This detector block consists of three stacked 10 by 10 arrays of individual detector voxels (see FIG. 2). Each autonomous detector block is able to broadcast the interactions events and be synchronized via a broadcast timing signal. It provides local static positional reference information, to establish the spatial coordinates of each voxel. The events are accumulated into local flash or dynamic memory for later transfer and analysis.

Figure 2:
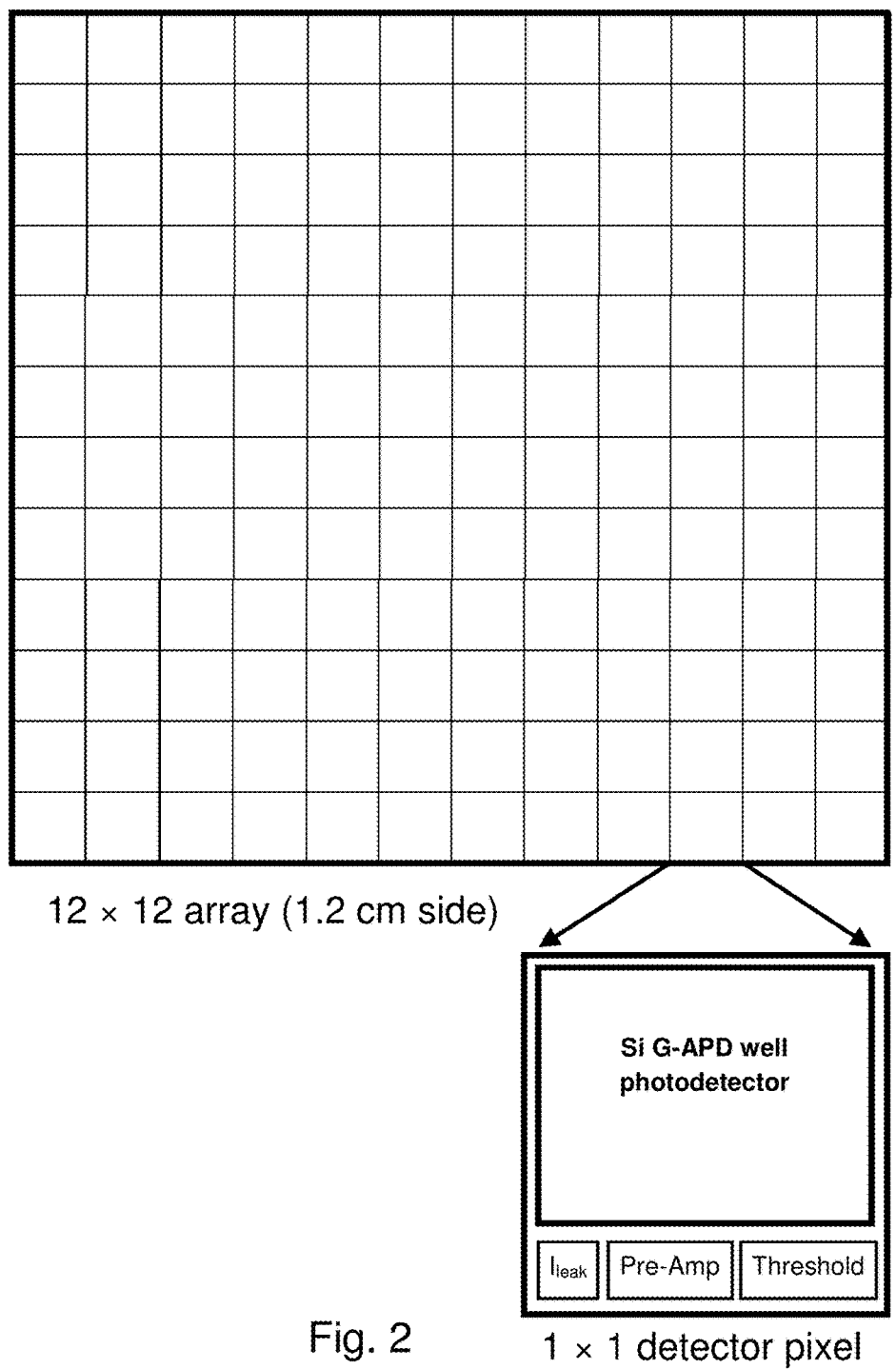
FIG. 2 shows a 12×12 self-contained Autonomous Detector Array (ADA) of plurality of self-contained ADVs, with a detail view showing a schematic for the analog processing electronics.

FIG. 2 shows an example of self-contained Autonomous Detector Array (ADA) of plurality of self-contained ADVs assembled into a detector array.

Figure 3:
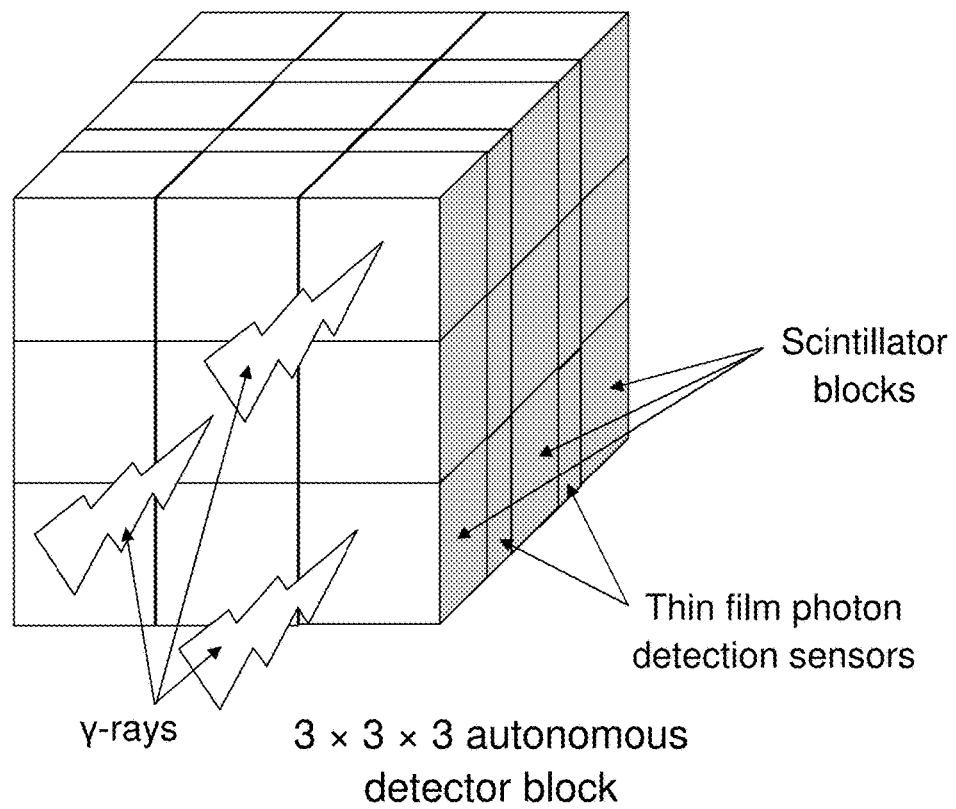
FIG. 3 shows an assembly of the three (3×3) autonomous detector arrays (ADAs) stacked into a (3×3×3) volumetric autonomous detector block (ADB). The ADB can be composed of an arbitrary number of ADVs in each of the three dimensions, and the thickness and size of the individual scintillator volumes in each sheet can be selected to optimize detection of the photons or particles of interest.

The ADAs can also be stacked to provide a three-dimensional configuration defined as an autonomous detector block (ADB). This stacking is especially important to improve depth-of-interaction information when coincidence detection is required as in positron emission tomography (PET). The number of ADAs in an ADB is arbitrary and is determined by the specific application for which a specific detector is used. The thickness of the scintillator blocks can be varied completely independently of all the ADVs or all the blocks in each individual layer can have the same thickness, but the thickness can be different for different layers. Thickness is defined as the radial dimension (FIG. 3). For example, the thickness of the scintillator can be adjusted for each layer to maximize the efficiency of event detection and to maximize the accuracy of the depth-of-interaction information.

FIG. 3 shows an example of an assembly of the three (3×3) autonomous detector arrays (ADAs) stacked into a (3×3×3) volumetric autonomous detector block (ADB). The ADB can be composed of an arbitrary number of ADVs in each of the three dimensions, and the thickness and size of the individual scintillator volumes in each sheet can be selected to optimize detection of the photons or particles of interest.

The modules may be organized as a 10 cm bore small animal PET system using the autonomous detector blocks (ADBs), as described above.

The autonomous detector blocks (ADBs) described above are stacked into modules of two ADBs creating a unit measuring approximately 10 by 10 by 30 mm (see FIG. 3). These modules aggregate the pulses from the layers along with their energy, timing, and position information and communicate this information to a remote storage location. Thirty-two of such modules are arranged radially with 32-fold symmetry into a ring of detectors providing much higher depth-of-interaction (DOI) resolution than presently possible (see FIG. 4). A ring can also consist of staggered autonomous detector voxels (ADVs, dark blue) arranged to maximize sensitivity, spatial resolution, DOI and uniformity, as shown in FIG. 5.

FIG. 4 shows thirty-two of modules arranged into a 32-fold symmetrical ring of detectors for 10 cm bore small animal PET system composed of the autonomous detector blocks (ADBs) depicted in FIG. 3.

The ADVs may be organized as a 70 cm bore whole body PET system using the autonomous detector blocks (ADBs), as described above:

The autonomous detector blocks (ADBs) described above are stacked into modules of two ADBs creating a unit measuring approximately 10 by 10 by 30 mm (see FIG. 3). These modules aggregate the pulses from the layers along with their energy, timing, and position information and communicate this information to a remote storage location. A detector ring consists of staggered autonomous detector voxels (ADVs, dark blue) arranged to maximize sensitivity, spatial resolution, DOI and uniformity, as shown in FIG. 5.

FIG. 5 shows a 70 cm diameter ring consisting of staggered autonomous detector blocks (dark blue, 10×10×10 mm$^3$) arranged to maximize sensitivity, spatial resolution, DOI, and uniformity. Twenty such rings are stacked to create a long cylindrical PET system.

Figure 6:
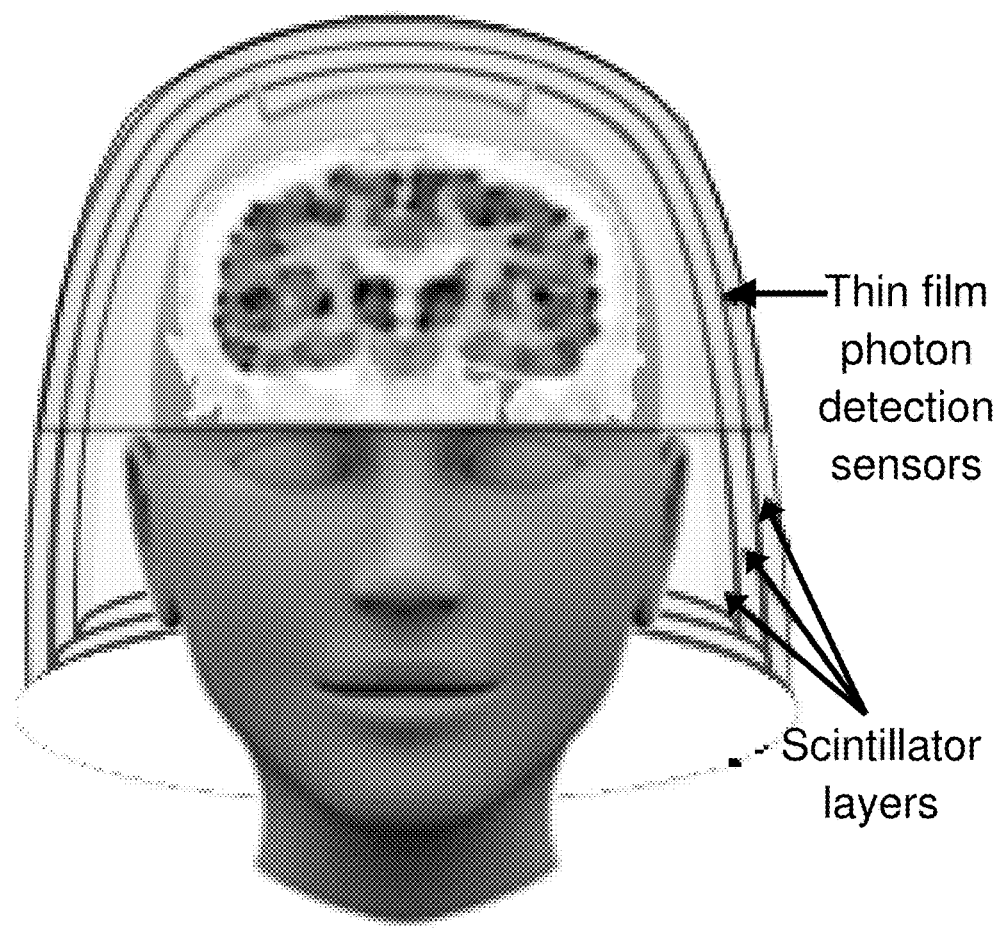
FIG. 6 shows the autonomous detector blocks assembled into a helmet shaped detector system for a dedicated wearable brain PET system.

The ADVs may be organized as a brain PET system using the autonomous detector blocks, as described above. Assembly of the autonomous detector blocks forms arbitrary shaped detector systems, e.g. a helmet shape for imaging the head and specifically the brain (FIG. 6). The arbitrary shape can be achieved by tiling of ADBs or ADBs modules oriented relative to each other and held by a frame much in the way a geodesic dome is assembled or by assembling flexible detector sheets that are made to be conformable to the desired shape much in the way a Mercator projection can be assembled into a sphere. If the radius of curvature of the desired shape is much larger than the size of the detectors and if the 2D sheets are fabricated on flexible substrates, then a single ADA or a 3D stack of ADAs or plurality of ADBs could be used much like a blanket to wrap around any complex-shaped object.

FIG. 6 shows an example of the autonomous detector blocks assembled into a helmet shaped detector system for a dedicated wearable brain PET system. The helmet may be supported by the head of the human subject, or may be further supported by the shoulders or other body parts. Preferably, the subject remains mobile while the helmet is in place, and significant normal activities may be conducted while it is in place. This permits functional testing of a patient, and extended tests.

The BET addresses, for example: 1) Current inability of PET to map brain activity of freely moving and acting subjects; 2) Low sensitivity, poor non-uniform spatial resolution of PET; 3) Large size and mass of PET scanners; 4) Very high cost and low spatial resolution of combined brain PET with MRI; 5) High cost of brain PET; and 6) PET scanner fragility, strong influence of environmental factors, need for high voltage, and significant power consumption.

The BET provides: TBI screening at the theater and field levels; improved molecular brain mapping and a screening procedure for TBI administered to fully mobile subjects; allows BET to reach 1-mm in vivo spatial resolution vs. 2.3-3.5 mm in conventional instruments; double the sensitivity, enabling a comparable number of photons to be collected in half the time required by conventional systems while reducing the amount of label required and the amount of radiation dose delivered; simultaneous PET/MRI (1-mm vs. 4-6.5 mm in conventional PET/MRI) brain studies with conventional MRIs; and lower cost due to inexpensive TFPDs with integrated onboard electronics [51, 52 ref from R21], allowing wider implementation of PET brain studies.

Helmet-shaped BET scanners are provided in two inexpensive portable configurations: one wearable and other portable but with higher sensitivity and adjustable tilt (from upright to horizontal).

BET may employ high resolution layered gamma detectors and a generalized PAPA penalized-likelihood image reconstruction algorithm [27] resulting in high-resolution/low-noise images. Consequently, it allows scans with lower radiation burden and/or better temporal resolution in dynamic studies than are currently possible. In addition, the improved sensitivity of BET allows better imaging of short radiotracer half-life isotopes (e.g. O-15, C-11) thereby allowing longer study durations.

BET employs a novel gamma-ray detector technology coupled with unique low-noise and high-resolution reconstruction approaches. BET that is based on thin-film photodetectors and flexible electronics methods is low mass (~10 kg and ~20 kg, respectively), rugged, low power, low-voltage, ultra-high spatial resolution (~1 mm) and high (or ultra-high) sensitivity helmet-shaped device. In the wearable configuration, the mass is reduced by using thinner scintillators in order to allow PET brain imaging of a free-moving subject performing active tasks and/or responding to various stimuli in any settings (e.g. outside lab) [1, 2]. Such neurological studies and brain mapping are currently not possible [3-24]. The second, portable, configuration increases the scintillator mass to provide improved resolution and sensitivity. Combination with other imaging modalities including fMRI and fcMRI is possible due to the small size of BET and its compatibility with MRI [25]. As a result, BET enables low-cost ultra-high resolution/sensitivity brain PET/MRI [26]. This is in contrast to extant brain PET scanners that are large, heavy, fragile, expensive, and have poor sensitivity and resolution [27-29]. BET's novel detector modules consist of many thin scintillator layers (optimized for brightness and short decay times) integrated with thin-film photodetectors and onboard electronics to achieve a fully solid-state low-voltage and low-power detector. Using flexible electronics methods, the multilayered detectors may be arranged into a helmet-like device to increase the collection solid angle by 250% and fully recover depth-of-interaction information resulting in uniform resolution across the field-of-view. BET employs a low-noise penalized-likelihood image reconstruction algorithm with a total variation penalty of the higher order gradients coupled with an efficient sub-gradient decent optimization algorithm.

The PSL/TFPD bilayers are stacked to provide the total scintillator thickness resulting in high (up to 95%) quantum efficiency for 511 keV photons. The number of bilayers is selected to deliver the desired depth-of-interaction (DOI) resolution hence uniform spatial resolution in vivo of preferably 1 mm across the field-of-view. These detectors are arranged into a helmet-like device that increases the gamma photon collection solid angle by 250% over typical designs.

Consequently, BET allows scans with lower radiation burden or better temporal resolution in dynamic studies.

Affordability of BET addresses the critical barrier of high cost of brain PET and PET/MRI mapping. It significantly increases access to brain PET and PET/MRI by researchers and clinicians. Thus, BET enables breakthroughs in brain molecular imaging that can only be imagined today [30].

Solid State Integrated Gamma, X-Ray and Particle Detector

The detector is designed to detect gamma rays, X-rays and energetic particles with high sensitivity and spatial resolution. The detector has particular application to medical imaging especially position emission tomography (PET), single photon emission computed tomography (SPECT), and gamma ray imaging allowing fabrication of better performing yet smaller, lighter and more rugged devices. The detector is miniaturized (by comparison to current systems), may be geometrically conformable, high resolution, large solid angle of collection, light-weight, low-voltage, low-power, and inexpensive. The detector could also be formed into complex geometric shapes by tiling planar or curved arrays of detectors to form the overall shape. Tiling has distinct advantages for detector maintenance and decreased cost of fabrication. Current systems are limited by their small solid angles of detection. The individual detectors can be fabricated into any desired size with subsequent improvement in the spatial resolution of detection leading to improved image resolution.

The form factors possible with the present architecture permit wearable devices, e.g., for human adults, to permit imaging of freely-moving subjects performing active tasks and/or responding to various stimuli in any settings (e.g. outside lab) Likewise, the technology offers portability, with ease of movement and setup in any location in a short time including emergency departments, ICUs and ambulances. The technology permits low power operation, and therefore battery operation is possible. The technology is not intrinsically fragile, and therefore may be made rugged for operation especially in adverse environments, with resistance to environmental factors including temperate gradients, vibrations, humidity, smoke, dust, etc. The technology is not particularly susceptible to strong external electromagnetic fields, and thus could be compatible with use in combination with MRI.

The detector comprises of a number (n≥1) of bilayers each consisting of a layer of pixelated scintillators (voxels) forming a k×l array and a thin layer of photodetectors forming a matching k×l array. There is one-to-one match between individual photodetector elements and the scintillator voxels. Individual photodetector elements could also include detection and control electronics. The bilayers are stacked to yield a multilayered detector providing depth of interaction information when applicable. The individual pixelated scintillator layers (PSLs) thicknesses and the total thickness of the stack are optimized for detection of the particular photons, or particles being detected. This configuration is especially important for positron emission tomography (PET).

According to one embodiment, the array of thin photodetectors are formed on thin film substrates or directly on the scintillator array. Arrays of all solid-state three-dimensional detector elements (dels) composed of a cylinder of scintillator material, mechanically and optically matched with a photodetector array element. The dels are optically and electrically isolated from each other. The detection and control electronics may be integrated near the photodetector and in most cases on the same substrate. The imaging or detection system may be fabricated into any geometric shape optimized for the detection or imaging task, including complex 3D geometries, including helmet for PET applications using modular detector approach.

The technology provides a miniaturized, geometrically conformable, high-resolution, large solid angle of collection, light-weight, low-voltage, low-power, inexpensive photon and particle detector with integrated scintillator and photodetectors. The photodetectors are integrated with the scintillator, forming a large array detector that can have complex shapes. The latter makes it possible to maximize the solid angle of collection and therefore the resolution, sensitivity, and imaging time of the system. The detector can be formed directly into complex geometric shapes using flexible electronics manufacturing methods, or by tiling small arrays of planar or curved detectors mounted on a frame or meshwork to form the overall shape. Tiling has distinct advantages for detector maintenance and decreased cost of fabrication. The dels can be fabricated into any desired size with subsequent improvement in the spatial resolution of detection, leading to improved image resolution. The detector can also be fabricated from any number of bilayers to provide the optimum trade-offs between depth of interaction resolution and total and individual scintillator layer thicknesses. The arrays can be composed of any number of individual dels arranged in any geometry. Further, each array can have as many stacked bilayers as desired with the thickness of each bilayer optimized for the detection or imaging task.

FIG. 6 shows an example of an imaging system comprised of three scintillator/TFPD bilayers designed for producing human brain PET (BET) images. The bilayers, in this example, are fabricated using flexible electronics methods into a helmet shaped detector that is sufficiently light that, with the aid of a supporting frame, could be worn by an adult human.

Blocks of scintillator may be cut into individual square cylinders for gamma rays detection for PET applications. The thin film photodetector (TFPD) arrays are matched to the bottom surface of the arrays of photodetectors. The scintillator thickness is optimized for each layer in the stack of bilayers to produce the most efficient detection of the incident gamma rays with the desired depth of interaction resolution. The polished square cylinders are covered on five sides with various optically transparent materials to maximize light yield through total internal reflection (e.g. index matching epoxies and thin metallic silver linings/coatings) and minimize optical crosstalk while the base facing the TFPD are optimized for optical coupling (e.g. using epoxy with optimized refractive index).

Three PSL/TFPDs arrays stacked to form a BET detector module. FIG. 3 shows an example of 12×12 photodetector array, as viewed from the top. An array of individual photodetectors, and their associated detection and control electronics is matched to the pixelated scintillator array such that one photodetector is aligned with one pixel (square cylinder) of scintillator. The photodetector occupies the bulk of the cross sectional area of each voxel to maximize detection of the scintillated light. This arrangement minimizes electrical noise and decreases the possibility of cross talk between voxels.

Each module may consist of a 12×12 array to match with the segmented scintillator crystals, with each optically isolated scintillator voxel coupled to one detector element, as represented in FIG. 2. Each module includes a high-density application-specific integrated circuit (ASIC) to provide common functionality including analog-to-digital converter (ADC) quantization of gamma events, energy discrimination, pixel identification, event timing, and distributed communication with the larger array of modules. Individual detectors in the array are preferably 1×1 mm, establishing the spatial resolution of the system. On the microelectronics level, each of the detector pixels is large and can accommodate significant additional circuitry; consequently, a small fraction of the area of each detector can be devoted to the local processing. Each pixel may include elements as shown in the exploded view. The majority of the area is devoted to the primary detector, e.g., a multi-well Geiger-mode avalanche photodiode (G-APD) detector structure matched to the spectrum of the selected scintillator [31]. By including an integrated pre-amp on each detector pixel, the gain of the G-APD can be reduced to achieve lower noise and reduced temperature sensitivity of operating parameters. To address variations in properties of the detector, a smaller area of the cell can also be devoted to a "dark leakage" diode (covered by an opaque coating) to establish the operating voltage requirements of each cell individually. Due to the low expected count rates, columns of detector elements would share a "bus" to transfer charge to a common ADC on the control and communication ASIC.

Due to the low expected count rates, columns of detector elements may advantageously share a "bus" to transfer charge to a common ADC on the control and communication ASIC. Other detector systems, including wide-bandgap amorphous oxide semiconductors (AOS) such InGaZn2O4 (IGZO), may offer advantages for integration on flexible substrates.

Each of the detector arrays may be coupled into a distributed system with 3-6 arrays stacked to provide sufficient absorption mass to capture positron annihilation events. These stacks are be tiled to provide coverage over the full BET design. Communication and coordination between the "master control" ASICs of each module may be provided.

The ASIC may be used to provide timing synchronization between detector arrays, and data storage for post processing e.g., local flash storage. To reduce the fraction of the volume devoted to the photosensor further, either direct fabrication of the G-APDs on the scintillator crystals, or on truly flexible substrates such as polyimide, may be employed.

A GATE [32] Monte Carlo models of the prototypes of the detector system and source may be used to determine the effects of the tradeoffs associated with the various detector designs [33, 34].

Figure 7:
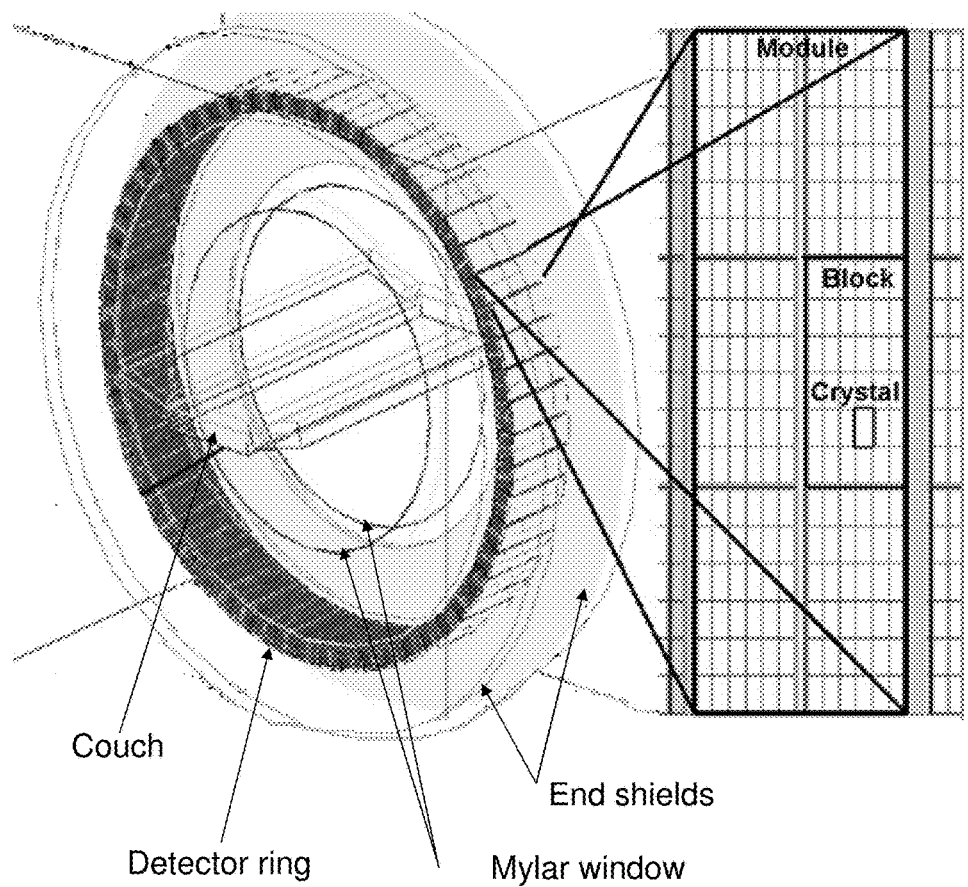
FIG. 7 shows a model of a ring detector.
Figure 8:
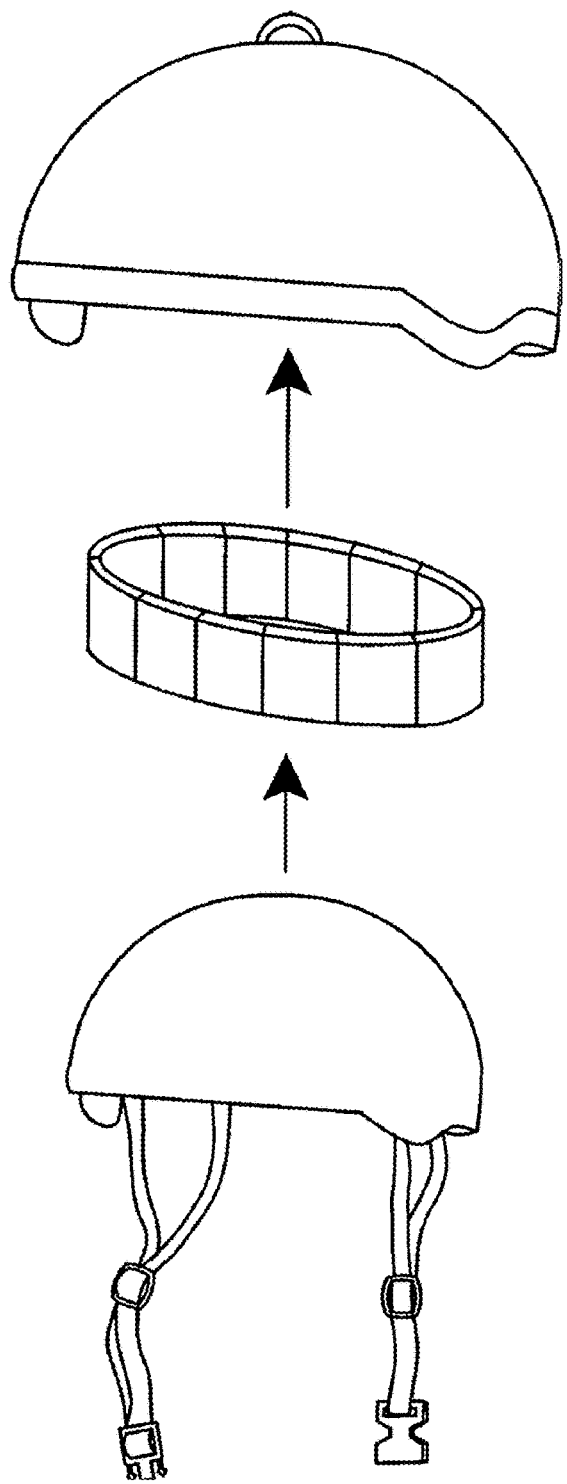
FIG. 8 (Prior Art) shows a prior art PET detector helmet design.

A model of the a detector is shown in FIG. 7, which shows a circular array of modules, each module having blocks of detectors, and each block having an array of crystals. The circular array surrounds a couch for the subject to lie on during the scanning. The ring has a Mylar window and end shields.

Figure 9:
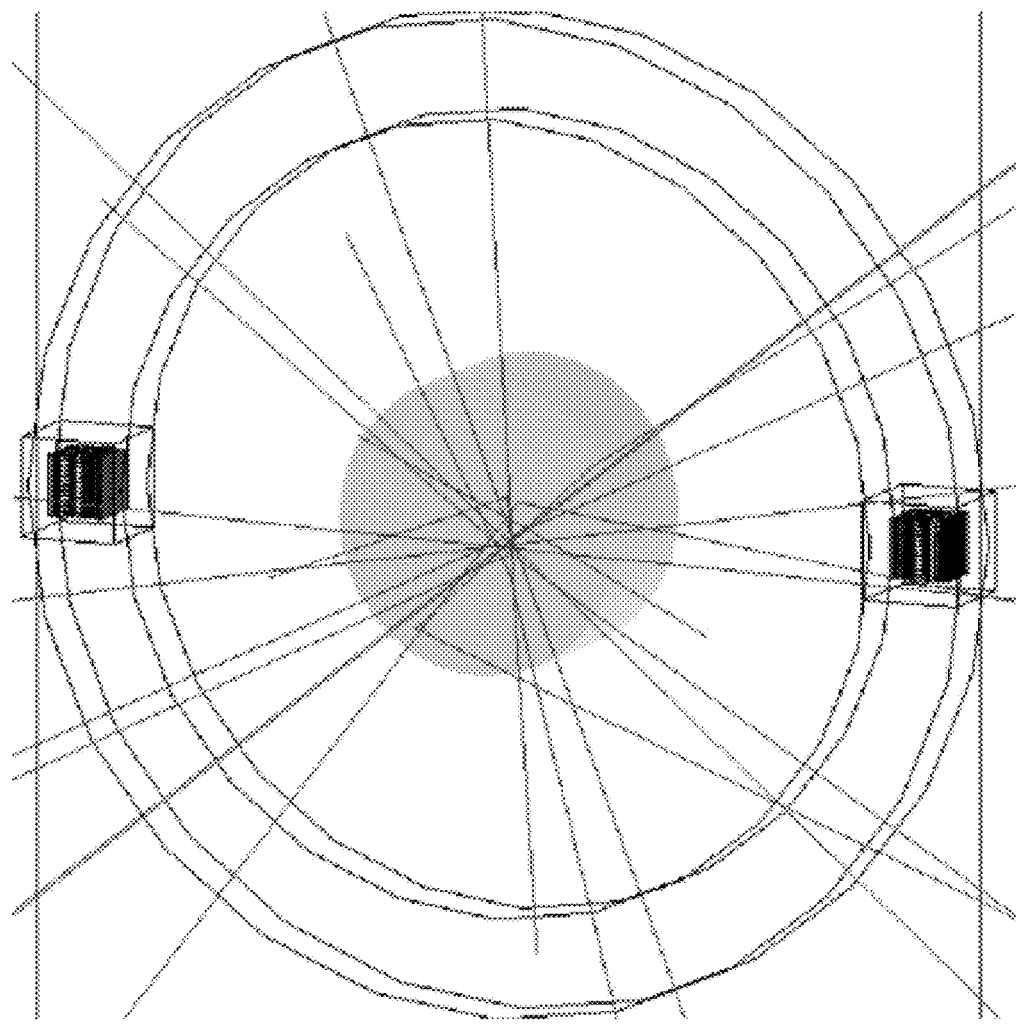
FIG. 9 shows a GATE model of two 3-layer 12×12 blocks of 1×1×10 mm LYSO scintillators with a line source embedded in a cylindrical phantom.

FIG. 9 shows a GATE model of two 3-layer 12×12 blocks of 1×1×10 mm LYSO scintillators with a line source embedded in a cylindrical phantom. When coincident scintillation within an appropriate energy range is detected by the opposed ADB sensors arrays, the source of the emission may be estimated as the line between the two detection events. As the size of the scintillation volume decreases, the spatial resolution increases, as does the overall system complexity. For coincidence detection, the minimum number of detectors is two, and an arbitrarily large number may be provided. A small number of detectors means that emitted rays are only captured over small spherical angles from the emission, and detection efficiency is reduced. However, sensitivity may be compensated by longer sampling periods.

Figure 10:
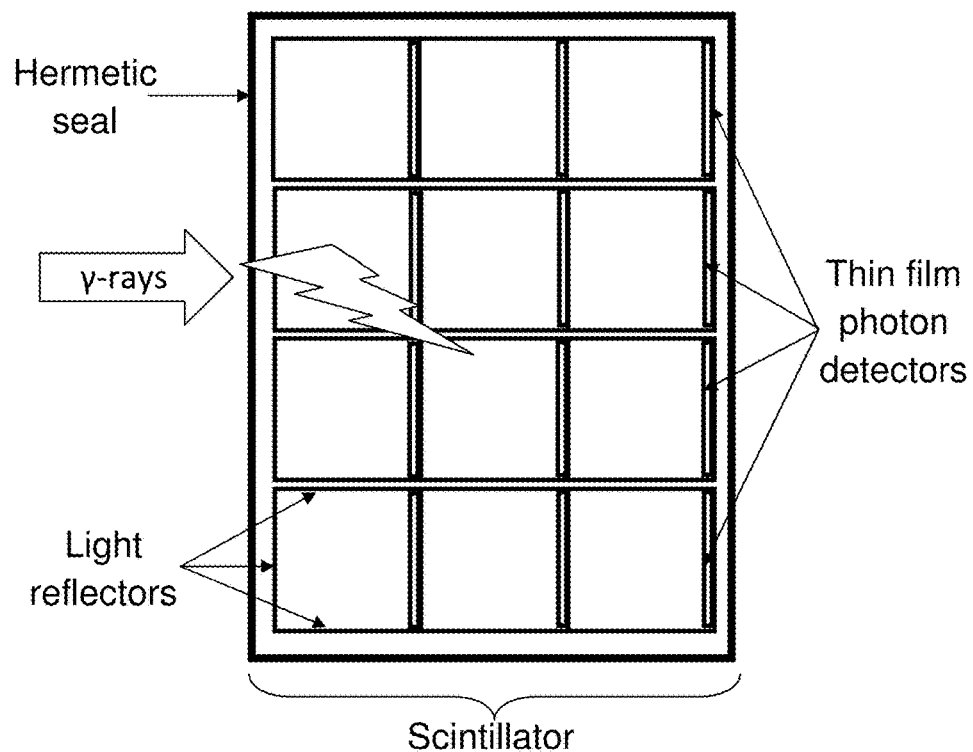
FIG. 10 shows a side view of a module of 3 stacked bilayers.

FIG. 10 shows a side view of a module of 3 stacked bilayers. γ-rays sought to be detected typically enter on one face, from the sensing space, though rays may enter from any angle. The γ-rays interact with some efficiency with the scintillation material in the scintillation crystal, and as a result of an interaction, generate photons. A quantity of photons generated from an interaction generally corresponds to the energy of the γ-ray. γ-rays may derive from a variety of sources, of which positron annihilation is only one example. The thin film photon detector (TFPD) system therefore quantitatively measures the photon emission, which may then be filtered according to particle energy. Those particles with lower or higher energy are ignored. If two γ-rays interact with the same scintillation crystal in too short a period of time, the detector may yield inaccurate results of either time, or energy, or both for the second event. Therefore, a delay to prevent detection of another event within a particular time window. The module is hermetically sealed, and each rectangular prismatic crystal is coated on 5 sides with a reflective coating, and further the various scintillation crystals are electrically isolated from each other. The thin film photon detector (TFPD) system is provided on the uncoated side of the crystal, and thus, after internal reflection, receives most of the emitted photons. The thin film photon detector (TFPD) system may be interconnected by a digital communication network, which may be, for example, a token ring or collision sense/multiple access type protocol. The ADB electronics therefore buffer one or more detection events, and transmit the detection event information records when convenient. For example, the transmission may be queued when any event is detection, when the buffer within the ADB reaches a threshold, when requested by a remote server (control system), or the like. The ADB requires a time reference (clock), which needs to be synchronized with other ADBs either at the ADB or at the remote server, in order to provide effective coincidence detection. The clock may be an arbitrary long counter, e.g., 256 bits, running off a stable oscillator, or may be synchronized with an external clock, such as a satellite atomic clock. Because of the high resolution required for quality coincidence detection, the remote server may process the transmitted records to estimate a time offset of each ADB, for example that which yields the best fit for predicted coincident detection of γ-rays with the other ADBs. The remote server, as a matter of convenience, may send a message to the ADB to calibrate or synchronize its clock.

The detector integrates sheets of arrays of TFPDs into the scintillator (LYSO or LaBr$_3$:Ce) at multiple depths. Layers of scintillator have thicknesses specified by the model for optimum γ-ray detection. This is shown for three layers in the FIG. 3. Each detector module, for example, consists of 12×12 array of scintillator/TFPD voxels in each layer. The scintillator blocks 13 mm×13 mm×(optimized length) are cut into rectangular cylinders 1 mm×1 mm×(optimized length), 95% of the length, and are thus rigidly connected. TFPDs may be aligned with the square bases of the scintillator voxels, and are coated with thin-film light reflectors on all sides except the one mated to the TFPD. Photons generated in a given scintillator voxel volume are detected only by the corresponding TFPD without significant cross-talk to other TFPDs.

Planar detector modules consisting of three layers of LYSO or LaBr$_3$:Ce scintillators (FIG. 4) can be modeled. An integrated system with the signal-processing model including the pulse pileup, dead time, and the energy and coincidence windows can be modeled allowing the determination of the depth of interaction, detector thickness (detector mass), noise equivalent counts, sensitivity, and spatial resolution properties. Two detector modules placed at 180° on the opposite side of the source forming BET can be modeled for coincidence operation and imaging. This BET can be used to compare the two scintillators, optimize the TFPDs, demonstrate the ability to estimate the depth of interaction by the detector, and to optimize the 3-D image reconstruction approach while operating in coincidence.

BET contains the planar detector modules mounted on a helmet shaped frame and working in coincidence mode to sweep out a solid angle of >2π steradians. The planar detector modules are configured like tiles and can be mounted in a variety of geometries including spheroidal sectors. In this way, more tiles can be added or easily changed to compare various detector optimizations. A point source and a brain phantom imaging may be modeled and the systems sensitivity and resolution determined. A GPAPA penalized-likelihood reconstruction image reconstruction algorithm [35] is preferably employed. Distance driven projectors [36] and spatially variant resolution recovery may be incorporated into the algorithm [37]. This is based on an interpolated shift-variant point response function (PRF) generated from point source simulations. BET thus may employ the penalized-likelihood image reconstruction algorithm with a total variation penalty of the higher order gradients coupled with an efficient sub-gradient decent optimization algorithm. Consequently, BET allows scans with lower radiation burden or better temporal resolution in dynamic studies.

To correct for motion between the subject and detector array, fiducial markers may be affixed to a cap on the patient's head or directly attached to the patient's scalp, and these detected by optical (camera), or RF means. These makers allow both the relative position of the patient's head to be tracked in time and to define the surface of the head for atlas based attenuation correction. With the patient's head location known as a function of time, the list-mode events can be subsequently rebinned into the correct lines of response, hence the resolution preserved and the Poisson nature of counting statistics within the detector bins restored.

This system may be similar in concept to the Calypso used by Varian Medical systems [38], the fiducial markers may contain magnetic transponders that can be spatially localized using an external radiofrequency system. However, rather than reporting the real-time motion of the center-of-mass, as is done in Calypso, the present technology may stream the time-tagged position data from a larger over-determined group of fiducial makers for post-processing event-by-event correction via least-squares rigid body position estimates [39]. Optical facial tracking as is described in [72] may also be implemented to track head movement.

TFPD arrays must ultimately be fabricated on thin flexible substrates that can be readily integrated within the system. Integration of electronic functionality has already been demonstrated on glass substrates in digital X-ray detectors and flat-panel displays. The TFPDs may be fabricated by similar techniques.

For BET, G-APD detectors show the greatest promise providing required energy resolution, speed, and integration [25]. Additionally, G-APDs arrays have been demonstrated over large areas (1×1 cm) in single crystal silicon [40]. And coupled with a LaBr$_3$:Ce scintillator, timing resolution down to 100 ps is feasible enabling time-of-flight enhancement to image reconstruction [41]. A wide range of substrates are possible, ranging from quartz (max 1100° C.) allowing near single crystal-like processing, to polyimides, e.g. Kapton (max 400° C.), that mimic capabilities expected in a roll-to-roll fabrication type process. a-Si is generally favored as a detector material due to its uniformity but, as G-APDs operate in the "binary" detection mode, uniformity issues that have generally challenged p-Si are less critical. The wide bandgap semiconductors such as IGZO offer significant potential gains in reverse leakage noise.

Processing techniques may be drawn primarily from flat panel technologies including both laser-recrystallized p-Si and partially crystallized IGZO referred to as CAAC.

The BET scintillator preferably exhibits high light output, fast and proportional response, high density, low absorption of visible light, high energy resolution, and high timing resolution [42-46]. Bright scintillators with fast luminescence allow accurate depth-of-interaction, encoding, and time-of-flight data collection [41]. LaBr$_3$:Ce and LYSO-based scintillator materials may be used [44-46]. The primary drawback of LaBr$_3$:Ce is its sensitivity to moisture, requiring hermetic packaging. The LaBr$_3$:Ce scintillators may be grown using a melt technique. Single crystals of Lu$_{1.8}$Y$_{0.2}$SiO$_5$:Ce (LYSO), Lu$_2$SiO$_5$:Ce (LSO) and Y$_2$SiO$_5$:Ce (YSO) may be grown using Czochralski (CZ) techniques [47, 48]. LYSO crystals may be grown from a solid solution of LSO/YSO (90/10) with approximately 0.05 Ce substituting for Lu and Y ions. The scintillators are cut out from the grown ingot into blocks which are further cut into rectangular cylinders 1 mm×1 mm×(optimized length) to 95% of the length (diamond saws or lasers), thus rigidly connected. The crystal surfaces are optically polished.

The integrated electronics may be provided using ultra-fine flip chip assembly. This technique reduces the size, weight, and power consumption of electronic devices, while providing: 1) Thin, down to 12.5 µm, cross sections with fabrication on polyimide or flexible glass films, and solder masks, as thin as 6 µm; 2) Fine line circuitization at 11 µm lines and spaces; 3) Plated laser-drilled vias as small as 25 µm diameter for double-sided fabrication; 4) Assembly of integrated circuit die and other components on flexible substrates. The individual scintillator elements, TFPD detectors, and ASIC control chips may be integrated into 1 mm thick detector "chiplets". These chiplets are then be assembled in detector module stacks of 3-6 elements to achieve the necessary gamma ray absorption. Finally, the detector modules are assembled on the substrate, and interconnected, to create the full conformal BET detector array.

Using flexible electronics methods, the multilayered detectors are arranged into a helmet-like device to increase the collection solid angle by 250% and fully recover depth-of-interaction information resulting in uniform resolution across the field-of-view.

The wearable BET system may be configured to employ a specialized "frame", such as a backpack, that supports the helmet by transferring the weight to the shoulders, back and hips. This allows BET imaging of free-moving subject performing active tasks and/or responding to various stimuli in any settings (e.g. outside lab) in a safe and practical manner. Such neurological studies and brain mapping include studies of behavior, obesity, bipolar disorder, schizophrenia, autism, and dementia. In these types of studies, brain and behavioral data should be acquired simultaneously under natural conditions. Unfortunately, this is not currently possible. However, the wearable BET scanner makes these previously impossible studies practical. In addition, this technology can be used in combination with other imaging modalities such as MRI to perform true simultaneous and high quality PET/MR brain images. These simultaneous images, acquired with BET with ultra-high resolution and sensitivity, allow neuroscientists to leverage their vast separate experiences with PET and MR into a synergistic whole that illuminates previously overlooked behaviors that were too subtle to see with either modality independently.

Monte Carlo (MC) is the standard tool for building computational models of detector blocks and in the case of PET GATE (Geant4 Application for Tomographic Emission) is the gold standard[17]. It is based off the Geant4 (Geometry and Tracking) general MC model used and developed by CERN for high-energy physics applications and has been extensively validated for PET and SPECT systems. To illustrate the level of detail and fidelity possible using this software, FIG. 1 shows a GATE model of the GE Discovery LS PET/CT [19] and an example of real and simulated pulses seen in the detectors. Voxelized phantoms and sources can also be used in GATE for modeling complex geometry and isotope distributions.

Using GATE, many details of the various detector designs can be incorporated into MC simulations. For the model's geometry and materials, the GATE software readily accepts a cylindrical of detector blocks and it allows the use of custom material compositions. In addition, more complicate custom geometries are also allowed, but require more effort. GATE also has a digitizer module for signal processing that includes pulse energy resolution, individual crystal light yield and transfer efficiency, detector crosstalk, energy thresholds and windows, timing resolution, memory and bandwidth effects, pileup timing, dead time, and coincidence sorting. Finally, after running GATE for a particular set of geometry and materials, the signal processing chain can be rerun multiple times using the digiGATE feature of the GATE code, allowing a detailed exploration of different signal processing options.

All modern PET/CT's use a statistical likelihood algorithm for image reconstruction where the maximum likelihood image is found relative to the data. While these techniques have a great deal of power, they tend to over-fit the data and produce noisy images. As a result, the images must be smoothed and that results in a loss of spatial resolution, i.e. the images look fuzzy. According to the present technology, a new algorithm, generalized preconditioned alternating projection algorithm (GPAPA), adds an image "roughness" penalty that reduces noise but preserves edges [16]. This penalty, the total variation of the norm of the images nth-order gradients, penalizes the likelihood function for noisy image estimates. This type of penalty term, well known in image processing for its power, is not differentiable and is thus both difficult to compute and slow to converge. The present algorithm is specially formulated for this type of problem and converges as quickly as the conventional image reconstruction algorithms using same number of iterations; as a result, the computational complexity is roughly doubled due to the additional expense of computing the penalty at each step.

The advantage that the present algorithm has over the existing commercial algorithms is that it handles the imaging noise/resolution tradeoff in a more natural and principled manner and still converges to a solution at a reasonable rate. The resulting images are both sharper and have less noise. This may allow physicians to see disease earlier and diagnose with more confidence than is possible currently. Furthermore, it may also allow acquisition of high quality images at a fraction of radiation dose or at a fraction of scanning time, as compared to the best standard-of-care approaches. Therefore, it would allow more frequent therapy response assessment or, in the case of faster scans, either the avoidance or limitation in duration of conscious sedation for pediatric patients.

An ordered-subset prototype of this algorithm has been tested in both simulations and on the General Electric Discovery-690 PET/CT and have reconstructed several patients' brain scans (370 MBq at 1-hour post-injection for 10 minutes) in time-of-flight mode with resolution recovery projectors. The results from the simulated data show a significant reduction in the "staircase" (piecewise constant regions) artifact for GPAPA compared to typical total variation regularization and lower RMSE (up to 35%) compared to optimally filtered OSEM. Qualitatively, the patient images appear much sharper and with less noise than standard clinical images. The convergence rate is similar to OSEM.

Functional brain imaging studies using the human wearable BET of mobile and active subject can last for hours and in any environment, compared to max 40-60 min with subject lying on a scanner bed in very restricted environments. The increased sensitivity coupled with the new image reconstruction algorithm may provide brain images of unrivaled detail and resolution.

BET's detector modules consist of many relatively thin scintillator layers each integrated with thin-film photodetectors and onboard electronics to achieve a fully solid-state low-voltage and low-power detector. Therefore, the total mass and size of BET device is predominantly defined by the mass and size of scintillator. This is in contrast to conventional brain PET scanner that requires significant additional mass and volume for PMTs and to a lesser degree (but still significant) for APDs. Low-power and low-voltage fully solid-state operation based on batteries lends itself well to wearability, portability, compatibility with strong electromagnetic fields and ruggedness of BET. It sallow high resolution/sensitivity brain PET scan of freely moving and acting subjects responding to various stimuli. It allows ultra-high resolution/sensitivity PET in brain PET/MRI scanners without the need for a very expensive dedicated scanner by simply positioning a subject with BET device inside an MRI. Such high spatial and temporal resolution of PET/MRI is not possible today. BET scanner is also compatible with other brain imaging and functional mapping modalities including EEG and MEG.

Using methods of flexible electronics, modular curved detector units may be provided. The plug-in detector elements used for fabrication of helmet-shaped BET devices with a solid angle of collection increased by ~250% or more (>2π srd) resulting in ~250% increase in sensitivity, and the optimized depth-of-interaction, resulting in uniform spatial resolution across the field of view. The number of detector modules can be adjusted to create a low mass (~20 lb) helmet-shaped high-resolution/sensitivity wearable BET or heavier (~30 lbs) helmet-shaped ultra-high resolution/sensitivity portable BET.

A good scintillator for the BET system has excellent light output, fast as well as proportional response, relatively high density (sensitivity), and absence of self-absorption in the visible portion of the electromagnetic radiation. Other useful characteristics are: high energy resolution because it allows rejection of scattered events and high timing resolution because it allows rejection of random events Furthermore, bright scintillators with fast luminescence allow new capabilities such as depth-of-interaction (DOI) encoding and time-of-flight data collection in BET. Both of these capabilities provide significant improvement in BET image quality.

To create $LaBr_3$:Ce crystals of sufficient size and quality, a melt-based process may be employed. The vertical Bridgman method may be used for growing $LaBr_3$:Ce crystals. Quartz ampoules are used as crucibles and ultra-dry $LaBr_3$ and $CeBr_3$ powders (99.99%, Alfa/Aesar) loaded in such ampoules, which are vacuum-sealed. These ampoules are then dropped through the vertical Bridgman furnace that has two temperature zones. The upper zone of the furnace is kept at temperature of 850° C., which is above the melting point of $LaBr_3$ and $CeBr_3$. This allows the constituents to mix well and react in the molten phase to form $LaBr_3$:Ce. The lower zone of the furnace is kept at 700° C. or lower (which is below the melting point of $LaBr_3$ and $CeBr_3$). As a result, $LaBr_3$:Ce crystals are formed as the ampoule enters the lower zone. $LaBr_3$:Ce crystals with volume $\geq 3$ $cm^3$ may be grown in this manner. The grown crystals are be removed from the quartz ampoule and then cut and polished using non-aqueous slurries in a glove box (due to hygroscopic nature of $LaBr_3$) prepared by mixing mineral oil with $Al_2O_3$ grit. The crystals are then packaged to prevent long exposure to moisture. This involves encapsulating the crystal in an epoxy (Epoxy STYCAST#1266 Value23LV Titanium Oxide and EPO-TEK 301 between the crystal and window) with a thin quartz window (0.5 mm) placed on the crystal face, which is coupled to an optical sensor.

Other packaging schemes may also be employed, e.g., placing a crystal in a metal can with a quartz window on one face. The crystal is attached to the quartz window using optical epoxy (EPO-TEK 301) and then $SiO_2$ powder pressed in the space between the metal can and the crystal. The metal disk is then be attached to the top surface to seal the detector.

Single crystals of $Lu_{1.8}Y_{0.2}SiO_5$:Ce (LYSO) may be grown using the CZ technique by following well documented methods available in the literature [67, 68]. $Lu_2SiO_5$:Ce (LSO) and Y2SiO5:Ce (YSO) crystals are grown first using CZ technique. Then LYSO crystals are grown from a solid solution of LSO/YSO (90/10) with approximately 1.5 at % Ce substituting for the lutetium and yttrium ions. An iridium crucible (M.P. ~2450° C.) is used for crystal growth. Samples are pulled from the crucible under a nominal $N_2$ plus a few ppm of dry $O_2$ atmosphere, with typical growth rate from 3 to 5 mm/h. Seeded growth is imposed by employing an off-axis seed of typical cross section 5-7 $mm^2$, with the simulated growth interface being convex to the melt surface.

While a minimum timing resolution of 5-6 ns is adequate, Schaart et. al [40] has demonstrated 100 ps resolution coincidence timing in $LaBr_3$:Ce using Si APDs. The performance of both external charge amplifier and integrated charge amplifiers preferably achieves resolution sufficient to enable time-of-flight enhancements to the image reconstruction.

Each of the detector arrays may be coupled into a distributed system with 3-6 arrays stacked to provide sufficient absorption mass to capture events. These stacks are tiled to provide coverage over the full BET design. For a timing resolution of 5-6 ns, the synchronization is not overly challenging (200 MHz), but to achieve resolutions of 100 ps, a self-calibration scheme is preferably employed, in which the timing of each detector element against a very stable clock is automatically determined, and as necessary, redetermined during use, to ensure high conincidence timing resolution. For example, the ASIC at each detector element can include a radio receiver to determine relative timing with respect to a master transmitter for the entire array. For example, Satellite radio transmissions, such as GPS/GNSS may include accurate clocks. Likewise, a wired/transmission line distribution of a clock may be employed.

Determination of coincidence events may be handled during acquisition or during post-acquisition processing. Storing all events requires much higher bandwidth to handle the high rate of single events. One potential solution is segmentation of the entire array into functional blocks with local flash storage for each sub-array.

The processing may be based on standard Si technology, though the arrays of the detector modules may also be fabricated using thin-film transistors similar to those employed in active matrix displays. Using conventional CMOS processing to develop the G-APDs, wafer-thinning techniques can reduce the "footprint" of the detector to 50-100 μm. To reduce the fraction of the volume devoted to the photosensor further, either direct fabrication of the G-APDs on the scintillator crystals, or on truly flexible substrates such as polyimide, may be employed.

The detector may be fabricated by integrating sheets of arrays of TFPDs into the scintillator at multiple depths. Layers of scintillator may be fabricated with thicknesses specified by the model for optimum γ-ray detection. The concept is shown for three layers in the FIG. 5. The scintillator blocks 13 mm×13 mm×(optimized length) are cut into rectangular cylinders 1 mm×1 mm×(optimized length), 95% of the length (diamond saws or lasers). So, they are rigidly connected. TFPDs are aligned with a rectangular volume of scintillator coated with thin-film light reflectors on all sides except the one mated to the TFPD. Photons generated in a given scintillator volume are detected only by the corresponding TFPD without significant cross-talk to other TFPDs.

The detectors may be provided in a 12×12 array of scintillator/TFPD voxels in each of the three layers, which are, e.g., be ~1.3×1.3 cm. Each TFPD includes a small area for the TFPD's detection circuitry, which includes photon burst detection corresponding to a gamma ray scintillation, a measure of the energy of the burst, and its detection relative to a master clock. The complete detector unit is, e.g., ~1.3×2 cm, to allow space for electrical traces to bring the signals to a connector for communication to the analysis electronics. Detectors are used to record events from calibrated point and extended sources of single gamma rays to demonstrate the operation of the detector, ability to distinguish depth interaction events, and compare the two scintillators under the same conditions observing the same sources. The detectors may be configured like tiles or modules that can be mounted in a variety of geometries including spherical sectors, e.g., in various layers within a helmet configuration. In this way, more tiles can be added or easily changed to compare various detector optimizations.

The GPAPA penalized-likelihood reconstruction is preferably used for the BET. Distance driven projectors may be preferred, because they have been shown to be fast and accurate [69]. As part of the projector design, spatially variant resolution recovery may be implemented in the algorithm. This is based on an interpolated shift-variant point response function (PRF) generated from point source measurements. The projectors and PRF may be tested using the Monte Carlo simulations of the various components and full scanner models.

The GPAPA algorithm may be implemented on parallel architecture computational system, using GPU's and/or massively parallel CPU systems Wide band-gap ultra-low leakage G-APD detectors based on amorphous oxide materials [112] may be fabricated directly on the scintillator crystals using low-temperature fabrication techniques developed for high performance TFT displays [113]. This leverages thin-film technologies developed for the active matrix display community [114] Fundamentally, G-APD operates as a collective of 5,000-10,000 individual APD cells, each operating in single-photon avalanche mode. Electron-hole pair(s) generated within each APD results in a "binary" discharge, with the collective current of multiple providing a near "linear" response. While G-APDs are normally designed to operate over a wide range of wavelengths with single-photon capability, detection of 511 keV gamma events allows tradeoffs between cost and complexity with the requisite performance level. In particular, the binary nature of avalanche cascades and isolation of APD cells is critical for use in a thin-film BET detector array. First, as cells are either fully discharged or not, the detector is tolerant of variations in the thin-film semiconductor. In addition, while each APD operates in singe-photon mode, a gamma event is a "large" signal simultaneous firing ~1000 cells. Consequently, high (uncorrelated) dark current rates for individual cells may be managed by an appropriate low-energy threshold. Limitations identified for the TFPDs may be mitigated also by replacing passive resistor quenching in cells with limited active quenching circuits [116].

Individual and coincident prototype detectors, individually and in layers, may be used to record flood histograms and build flood maps using calibrated point sources[128]. The uniformity of counts, and energy/timing resolution are optimized for the crystals in each detector, and extended to layers for DOI readout[129]. Each layer's crystal map is linearized by assigning physical positions to each point in the map and the energy and timing centroids are normalized. Next, the energy resolution is measured and an optimized energy window determined.

Figure 11:
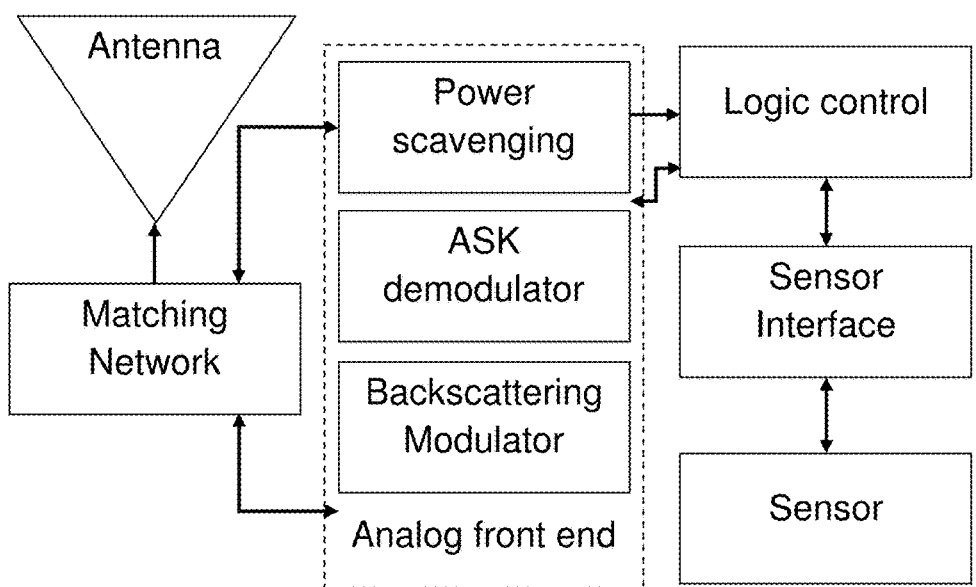
FIG. 11 shows a block diagram of an RFID backscatter communication implementation of the ADB system.

Recent developments in RFID technology have opened up the possibility of employing a wireless communication system according to an RFID communication protocol for transferring data to an auxiliary processor for event storage and analysis. See, FIG. 11. One advantage of the RFID communication systems is that, by use of a standard protocol, is possible to use the same reader with different sensor tags, thus reducing the cost of the system and improving the integration of the PET imaging systems. Accordingly, system is integrated with a RF energy harvester, a full passive UHF RFID tag and the sensor package, a compact implanted antenna and a low power sensor interface with digital outputs. It has four man blocks: (1) the analog front-end (FE), the digital module which includes the EEPROM, sensor interface and sensors. The analog FE is to supply power and clock signal to tag and to demodulate and modulate the input/output signals during the communications with the reader. (2) Power management unit, an amplitude shift keying (ASK) demodulator and backscattering modulator, a clock generator unit, sensor interface, and an antenna for both short range wireless powering as well as data and clock. (3) A high performance antenna in terms of efficiency, radiation pattern and input impedance matching for implantable passive RFID tags is provided; and a power scavenging techniques employed based on electromagnetic coupling for powering passive RFID implanted devices. A low power sensor interface with digital outputs are preferably employed. (4) The sensor interface converts the sensor data from Analog to Digital, its architecture reduces area and power requirement, it is also less sensitive to supply, temperature and process variations.

Various components of the PET system described above, including the autonomous modules, can interface with various types of special purpose or general purpose computer systems or programmable logic. One such computer system may be implemented having an internal bus or other communication mechanism for communicating information, as well as external interfaces, including for example an addressable shared packet switched digital communication network, such as defined in IEEE 802.X, e.g., 802.3 (Ethernet), 802.11 (wireless LAN, WiFi), 802.15 (wireless PAN, e.g., Bluetooth), etc., each of which standards and revisions/versions thereof is expressly incorporated herein by reference in its entirety. Such shared networks may provide a time division multiplexing scheme, such as token ring, and/or a collision sensing protocol. The packets may be TCP/IP packets, though in advanced embodiments, more efficient protocols may be employed. See, e.g., U.S. Pat. Nos. 7,305,486; 8,745,263; 8,713,189; 8,650,313; 8,577, 994; 8,542,582; 8,443,057; 8,341,401; 8,312,147; 8,239, 548; 8,223,628; 8,194,690; 8,171,147; 8,145,698; 8,086, 692; 8,069,251; 8,068,457; 7,974,247; 7,961,613; 7,911, 994; 7,899,925; 7,844,681; 7,724,775; 7,720,973; 7,693, 998; 7,680,993; 7,680,151; 7,649,909; 7,593,323; 7,526, 565; 4,475,192; 4,841,526; 5,245,616; 5,432,824; 5,442, 637; 5,528,591; 5,633,867; 5,825,748; 5,852,602; 6,038, 606; 6,205,120; 6,219,713; 6,243,358; 6,337,865; 6,347, 337; 6,594,701; 6,654,787; 6,683,850; 6,724,721, each of which is expressly incorporated herein by reference in its entirety.

The computing system employs a processor, i.e., an automated microprocessor or processor core(s) having one or more arithmetic logic units, instruction decoders, program counters, registers, etc., to implement functions define by software represented by instruction codes.

The computer system also includes a main memory which is a dynamic storage medium, such as a random access memory (RAM) or other dynamic storage device (e.g., dynamic RAM (DRAM), static RAM (SRAM), and synchronous DRAM (SDRAM)), as well as persistent storage, such as flash memory, MRAM, FRAM, or the like, coupled to the bus for storing information and instructions to be executed by processor. The main memory is typically used for storing temporary variables, tables, arrays, records, and other data structures, or other intermediate information during the execution of instructions by the automated processor. In some cases, the module stores a bootloader in persistent memory, and downloads executable code for normal operation through a digital communication network interface. The program code (and perhaps operating system) in this case executes from volatile memory.

An autonomous detector will typically not include a mass storage device distinct from a flash memory holding, e.g., 1-128 GB of memory. However, in some cases, the autonomous detector may have a general purpose or special purpose interface through which mass storage devices may be controlled and communicated with, and the automated processor and operating sytem may certainly support such devices and interfaces. On the other hand, the flash storage device may interface to the module through a USB port, SDHC, or other consumer electronics interface. For example, the autonomous detector may include USB 2.0, USB 3.0, USB 3.1, Thunderbolt, SATA, HDMI 1.4 or higher, or another interface. Typically, the shared digital communications network interface will employ distinct hardware from the general purpose or storage device interface.

The computer system may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

Stored on any one or on a combination of computer readable media, the present invention includes software for controlling the computer system, for driving a device or devices for implementing the invention, and for enabling the computer system to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

Thus, one aspect of the technology provides a discrete computer readable medium, typically with a wired electrical interface, to store executable instructions for controlling the autonomous detector module.

The autonomous detector module may cooperate with other modules, especially in coordinating communications through the shared digital communication medium, but also to provide for distributed processing. The autonomous detector modules may be fully symmetric, or be provided with differing capabilities.

In some cases, a module may be provided which does not have or does not use detectors, and is provided to support other modules. In some cases, the communication from each autonomous detector module through the network is to a server or imaging/synchronization processor, while in other cases, the communications will be hierarchical, such that packets pass from one module through a gateway module before being pass for external processing. Indeed, the system itself may be configurable and reconfigurable, and assuming different modes of operation depending on load, processing and communication headroom, and other factors.

The term "computer readable medium" as used herein refers to any tangible medium that participates in providing instructions to the automated processor for execution, but will exclude electromagnetic waves in transit. A computer readable medium may take many forms, including but not limited to, non-volatile media, and volatile media. Non-volatile media includes, for example, optical, magnetic disks, and magneto-optical disks, such as the hard disk or the removable media drive. Volatile media includes dynamic memory, such as the main memory.

The autonomous detector module includes a shared addressable digital communication network interface port, under control of the automated processor, which typically operates by communicating packets of information, e.g., IP packets, under a TCP or UDP protocol or modifications thereof. The architecture typically adopts schemes from the "Internet of Things", rather than the World Wide Web, and in particular, the autonomous detector modules typically have no readily accessible human user interface, i.e., lack a web server or HTML browser capability. This is, of course, not a technological limitation, but rather is for efficiency and security.

The autonomous detector modules typically support cryptographically secured downloads of program instructions, and thus would typically support a public key infrastructure certificate infrastructure or multi-step authentication protocol, before accepting new or modified instructions from an external source. Packets transmitted by a autonomous detector module may be signed with a cryptographic hash, but in most cases do not need to be encrypted. If encrypted, an AES symmetric key encryption algorithm, for example, may be employed.

The communication interface provides a two-way data communication coupling to a network link that is connected to, for example, a local area network (LAN) to an image processing rack or workstation. While Internet protocols, e.g., IPv4 or IPv6 may be employed, access to the Internet is not a requirement, and may expose the system to security risks. For example, the communication interface may be a network interface card to attach to any packet switched LAN. The network link typically provides data communication through one or more networks to other data devices. For example, the network link may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 6A, CAT 7, CAT 8 cable, coaxial cable, optical fiber, etc.). The signals through the various networks and the signals on the network link and through the communication interface, which carry the digital data to and from the computer system, may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system can transmit and receive data, including program code, through the networks, the network link and the communication interface.

The language used in this application is intended to be interpreted in its context, and according to its technical meaning as would be understood by a person of ordinary skill in the art. Therefore, word and phrases assume their meaning as used in the scholarly technical literature, and lay dictionaries shall not be presumed to be reliable indicators of their meaning.

Numerous modifications and variations of the present invention are possible in light of the above teachings. It is therefore to be understood that within the scope of the appended claims, the invention may be practiced otherwise than as specifically described herein.

REFERENCES

The references cited herein are each expressly incorporated herein by reference in their entirety.

1. Sobesky, J., Refining the mismatch concept in acute stroke: lessons learned from PET and MRI. Journal of Cerebral Blood Flow & Metabolism, 2012. 32(7): p. 1416-1425.
2. Giacino, J. T., et al., Disorders of consciousness after acquired brain injury: the state of the science. Nature Reviews Neurology, 2014.
3. Laureys, S., A. M. Owen, and N. D. Schiff, Brain function in coma, vegetative state, and related disorders. The Lancet Neurology, 2004. 3(9): p. 537-546.
4. Laureys, S. and N. D. Schiff, Coma and consciousness: paradigms (re) framed by neuroimaging. Neuroimage, 2012. 61(2): p. 478-491.
5. Heiss, W. D., PET in coma and in vegetative state. European Journal of Neurology, 2012. 19(2): p. 207-211.
6. Hattori, N., et al., Acute changes in regional cerebral 18F-FDG kinetics in patients with traumatic brain injury. Journal of Nuclear Medicine, 2004. 45(5): p. 775-783.

7. Schmidtlein, C., et al., Using an external gating signal to estimate noise in PET with an emphasis on tracer avid tumors. Physics in medicine and biology, 2010. 55(20): p. 6299.
8. Kirov, A., J. Piao, and C. Schmidtlein, Partial volume effect correction in PET using regularized iterative deconvolution with variance control based on local topology. Physics in medicine and biology, 2008. 53(10): p. 2577.
9. Stenger, F. and R. Schmidtlein, Conformal maps via sinc methods. SERIES IN APPROXIMATIONS AND DECOMPOSITIONS, 1999. 11: p. 505-550.
10. Chaudhuri, S. K., et al., Large Area $Cd_{0.9}Zn_{0.1}Te$ Pixelated Detector: Fabrication and Characterization. Nuclear Science, IEEE Transactions on, 2014. 61(2): p. 793-798.
11. Chaudhuri, S. K., K. J. Zavalla, and K. C. Mandal, Experimental determination of electron—hole pair creation energy in 4H—SiC epitaxial layer: An absolute calibration approach. Applied Physics Letters, 2013. 102(3): p. 031109.
12. Chaudhuri, S. K., et al., Biparametric analyses of charge trapping in $Cd_{0.9}Zn_{0.1}Te$ based virtual Frisch grid detectors. Journal of Applied Physics, 2013. 113(7): p. 074504.
13. Chaudhuri, S. K., et al., Schottky barrier detectors on 4H—SiC n-type epitaxial layer for alpha particles. Nuclear Instruments and Methods in Physics Research Section A: Accelerators, Spectrometers, Detectors and Associated Equipment, 2013. 701: p. 214-220.
14. Krishna, R., et al., Characterization of $Cd_{0.9}Zn_{0.1}Te$ based virtual Frisch grid detectors for high energy gamma ray detection. Nuclear Instruments and Methods in Physics Research Section A: Accelerators, Spectrometers, Detectors and Associated Equipment, 2013. 701: p. 208-213.
15. Mandal, K. C., et al., Fabrication and Characterization of Schottky Diodes for High Resolution Nuclear Radiation Detectors. Nuclear Science, IEEE Transactions on, 2012. 59(4): p. 1504-1509.
16. Mandal, K. C., et al., Characterization of semi-insulating 4H silicon carbide for radiation detectors. Nuclear Science, IEEE Transactions on, 2011. 58(4): p. 1992-1999.
17. Das, S., et al., Defect levels in Cu2ZnSn (SxSe1-x) 4 solar cells probed by current-mode deep level transient spectroscopy. Applied Physics Letters, 2014. 104(19): p. 192106.
18. Mandal, K. C., et al. Characterization of amorphous selenium alloy detectors for x-rays and high energy nuclear radiation detection. in SPIE Optical Engineering+ Applications. 2013. International Society for Optics and Photonics.
19. Krishna, R. M., P. G. Muzykov, and K. C. Mandal, Electron beam induced current imaging of dislocations in $Cd_{0.9}Zn_{0.1}Te$ crystal. Journal of Physics and Chemistry of Solids, 2013. 74(1): p. 170-173.
20. Mandal, K. C., et al., Characterization of Low-Defect $Cd_{0.9}Zn_{0.1}Te$ and CdTe Crystals for High-Performance Frisch Collar Detectors. Nuclear Science, IEEE Transactions on, 2007. 54(4): p. 802-806.
21. Mandal, K. C., et al. Amorphous selenium based detectors for medical imaging applications. in SPIE Optics+ Photonics. 2006. International Society for Optics and Photonics.
22. Kincaid, R., et al. Development of ultrafast laser-based x-ray in-vivo phase-contrast micro-CT beamline for biomedical applications at Advanced Laser Light Source (ALLS). in Optical Engineering+ Applications. 2008. International Society for Optics and Photonics.
23. Krol, A., et al., Laser-based microfocused x-ray source for mammography: Feasibility study. Medical physics, 1997. 24(5): p. 725-732.
24. Schnopper, H. W., S. E. Romaine, and A. Krol. X-ray monochromator for divergent beam radiography using conventional and laser-produced x-ray sources. in International Symposium on Optical Science and Technology. 2001. International Society for Optics and Photonics.
25. Serbanescu, C., et al. K-alpha x-ray source using high energy and high repetition rate laser system for phase contrast imaging. in SPIE Optical Engineering+ Applications. 2009. International Society for Optics and Photonics.
26. Smith, G., A. Krol, and Y. Kao, A low pressure, parallel plate avalanche chamber for detection of soft X-ray fluorescence. Nuclear Instruments and Methods in Physics Research Section A: Accelerators, Spectrometers, Detectors and Associated Equipment, 1990. 291(1): p. 135-139.
27. Krol, A., et al., Preconditioned alternating projection algorithms for maximum a posteriori ECT reconstruction. Inverse problems, 2012. 28(11): p. 115005.
28. Jan, S., et al., GATE: a simulation toolkit for PET and SPECT. Physics in medicine and biology, 2004. 49(19): p. 4543.
29. Mitev, K., et al., Influence of photon energy cuts on PET Monte Carlo simulation results. Medical Physics, 2012. 39(7): p. 4175-4186.
30. Schmidtlein, C. R., et al., Validation of GATE Monte Carlo simulations of the GE Advance/Discovery LS PET scanners. Medical Physics, 2006. 33(1): p. 198-208.
31. Krol, A., et al. Motion correction via nonrigid coregistration of dynamic MR mammography series. In Medical Imaging. 2006. International Society for Optics and Photonics.
32. Chaudhuri, S. K., et al., $Cd_{0.9}Zn_{0.1}Te$ Crystal Growth and Fabrication of Large Volume Single-Polarity Charge Sensing Gamma Detectors. 2013.
33. Das, S. and K. C. Mandal, Growth and characterization of kesterite Cu 2 ZnSn (SxSe 1-x) 4 crystals for photovoltaic applications. Materials Research Bulletin, 2014.
34. Zheng, L. Y., et al., Electrochemical measurements of biofilm development using polypyrrole enhanced flexible sensors. Sensors and Actuators B: Chemical, 2013. 182: p. 725-732.
35. Mandal, K. C., et al., Low Energy X-Ray and γ-Ray Detectors Fabricated on n-Type 4H—SiC Epitaxial Layer. 2013.
36. Chaudhuri, S. K., K. J. Zavalla, and K. C. Mandal, High resolution alpha particle detection using 4H—SiC epitaxial layers: Fabrication, characterization, and noise analysis. Nuclear Instruments and Methods in Physics Research Section A: Accelerators, Spectrometers, Detectors and Associated Equipment, 2013. 728: p. 97-101.
37. Mandal, K. C., P. G. Muzykov, and J. R. Terry, Highly sensitive x-ray detectors in the low-energy range on n-type 4H—SiC epitaxial layers. Applied Physics Letters, 2012. 101(5): p. 051111.
38. Muzykov, P. G., R. M. Krishna, and K. C. Mandal, Temperature dependence of current conduction in semi-insulating 4H—SiC epitaxial layer. Applied Physics Letters, 2012. 100(3): p. 032101.
39. Alzoubi, K., et al., Factor effect study for the high cyclic bending fatigue of thin films on PET substrate for flexible displays applications. Display Technology, Journal of, 2011. 7(6): p. 348-355.

40. Shan, S., et al., Flexibility characteristics of a polyethylene terephthalate chemiresistor coated with a nanoparticle thin film assembly. Journal of Materials Chemistry C, 2014.

41. Gao, Y., et al., Effects of the catalyst and substrate thickness on the carbon nanotubes/nanofibers as supercapacitor electrodes. Physica Scripta, 2012. 86(6): p. 065603.

42. Gao, Y., et al., Chemical vapor-deposited carbon nanofibers on carbon fabric for supercapacitor electrode applications. Nanoscale research letters, 2012. 7(1): p. 1-8.

43. Maramraju, S. H., et al., Small animal simultaneous PET/MRI: initial experiences in a 9.4 T microMRI. Physics in medicine and biology, 2011. 56(8): p. 2459.

44. Schulz, D., et al., Simultaneous assessment of rodent behavior and neurochemistry using a miniature positron emission tomograph. nAture methods, 2011. 8(4): p. 347-352.

45. Krol, A., et al. Comparative studies of collimator performance in DaTscan (Ioflupane I-123) striatal SPECT. in SPIE Medical Imaging. 2013. International Society for Optics and Photonics.

46. Biegon, A., et al., Regional Distribution of Aromatase in the Human Brain. Brain Aromatase, Estrogens, and Behavior, Oxford University Press, New York, 2012: p. 89-96.

47. Gray, N. A., et al., Antidepressant treatment reduces serotonin-1A autoreceptor binding in major depressive disorder. Biological psychiatry, 2013. 74(1): p. 26-31.

48. Milak, M. S., et al., In vivo serotonin-sensitive binding of [$^{11}$C] CUMI-101: a serotonin 1A receptor agonist positron emission tomography radiotracer. Journal of Cerebral Blood Flow & Metabolism, 2011. 31(1): p. 243-249.

49. Miller, J. M., et al., Positron emission tomography quantification of serotonin transporter in suicide attempters with major depressive disorder. Biological psychiatry, 2013. 74(4): p. 287-295.

50. Lan, M. J., et al., Higher pretreatment 5-HT1A receptor binding potential in bipolar disorder depression is associated with treatment remission: A naturalistic treatment pilot PET study. Synapse, 2013. 67(11): p. 773-778.

51. Yuan, H.-C., et al., Flexible photodetectors on plastic substrates by use of printing transferred single-crystal germanium membranes. Applied Physics Letters, 2009. 94(1): p. 013102.

52. Dhar, S., D. M. Miller, and N. M. Jokerst, High responsivity, low dark current, heterogeneously integrated thin film Si photodetectors on rigid and flexible substrates. Optics express, 2014. 22(5): p. 5052-5059.

53. Horwitz, B. and D. Poeppel, How can EEG/MEG and fMRI/PET data be combined? Human brain mapping, 2002. 17(1): p. 1-3.

54. Knowlton, R. C., The role of FDG-PET, ictal SPECT, and MEG in the epilepsy surgery evaluation. Epilepsy & Behavior, 2006. 8(1): p. 91-101.

55. Mulert, C., et al., Integration of fMRI and simultaneous EEG: towards a comprehensive understanding of localization and time-course of brain activity in target detection. Neuroimage, 2004. 22(1): p. 83-94.

56. Debener, S., et al., Single-trial EEG-fMRI reveals the dynamics of cognitive function. Trends in cognitive sciences, 2006. 10(12): p. 558-563.

57. Ritter, P. and A. Villringer, Simultaneous EEG-fMRI. Neuroscience & Biobehavioral Reviews, 2006. 30(6): p. 823-838.

58. Moosmann, M., et al., Joint independent component analysis for simultaneous EEG-fMRI: principle and simulation. International Journal of Psychophysiology, 2008. 67(3): p. 212-221.

59. Moses, W. W., Fundamental limits of spatial resolution in PET. Nuclear Instruments and Methods in Physics Research Section A: Accelerators, Spectrometers, Detectors and Associated Equipment, 2011. 648: p. S236-S240.

60. Rahmim, A., J. Qi, and V. Sossi, Resolution modeling in PET imaging: Theory, practice, benefits, and pitfalls. Medical physics, 2013. 40(6): p. 064301.

61. Fu, L. and J. Qi, A residual correction method for high-resolution PET reconstruction with application to on-the-fly Monte Carlo based model of positron range. Medical physics, 2010. 37(2): p. 704-713.

62. McDermott, G. M., F. U. Chowdhury, and A. F. Scarsbrook, Evaluation of noise equivalent count parameters as indicators of adult whole-body FDG-PET image quality. Annals of nuclear medicine, 2013. 27(9): p. 855-861.

63. Wu, J., et al., An economical fluorescence detector for lab-on-a-chip devices with a light emitting photodiode and a low-cost avalanche photodiode. Analyst, 2012. 137(2): p. 519-525.

64. Vaska, P., et al., RatCAP: miniaturized head-mounted PET for conscious rodent brain imaging. Nuclear Science, IEEE Transactions on, 2004. 51(5): p. 2718-2722.

65. Woody, C., et al., RatCAP: a small, head-mounted PET tomograph for imaging the brain of an awake RAT. Nuclear Instruments and Methods in Physics Research Section A: Accelerators, Spectrometers, Detectors and Associated Equipment, 2004. 527(1): p. 166-170.

66. Rubinsztein, J. S., et al., Decision-making in mania: a PET study. Brain, 2001. 124(12): p. 2550-2563.

67. Blumberg, H. P., et al., Increased anterior cingulate and caudate activity in bipolar mania. Biological psychiatry, 2000. 48(11): p. 1045-1052.

68. Nugent, A. C., et al., Reduced post-synaptic serotonin type 1A receptor binding in bipolar depression. European Neuropsychopharmacology, 2013. 23(8): p. 822-829.

69. Sullivan, G. M., et al., Positron emission tomography quantification of serotonin-1A receptor binding in medication-free bipolar depression. Biological psychiatry, 2009. 66(3): p. 223-230.

70. DeLorenzo, C., et al., In vivo variation in metabotropic glutamate receptor subtype 5 binding using positron emission tomography and [$^{11}$C] ABP688. Journal of Cerebral Blood Flow & Metabolism, 2011. 31(11): p. 2169-2180.

71. DeLorenzo, C., et al., In vivo positron emission tomography imaging with [$^{11}$C] ABP688: binding variability and specificity for the metabotropic glutamate receptor subtype 5 in baboons. European journal of nuclear medicine and molecular imaging, 2011. 38(6): p. 1083-1094.

72. Cozzoli, D. K., et al., Nucleus Accumbens mGluR5-Associated Signaling Regulates Binge Alcohol Drinking Under Drinking-in-the-Dark Procedures. Alcoholism: Clinical and Experimental Research, 2012. 36(9): p. 1623-1633.

73. Spooren, W., et al., Insight into the function of Group I and Group II metabotropic glutamate (mGlu) receptors: behavioural characterization and implications for the treatment of CNS disorders. Behavioural pharmacology, 2003. 14(4): p. 257-277.

74. Deschwanden, A., et al., Reduced metabotropic glutamate receptor 5 density in major depression determined by [11C] ABP688 PET and postmortem study. American Journal of Psychiatry, 2011. 168(7): p. 727-734.

75. Price, R. B., et al., Amino acid neurotransmitters assessed by proton magnetic resonance spectroscopy: relationship to treatment resistance in major depressive disorder. Biological psychiatry, 2009. 65(9): p. 792-800.

76. Yüksel, C. and D. Öngür, Magnetic resonance spectroscopy studies of glutamate-related abnormalities in mood disorders. Biological psychiatry, 2010. 68(9): p. 785-794.

77. Gigante, A. D., et al., Brain glutamate levels measured by magnetic resonance spectroscopy in patients with bipolar disorder: a meta-analysis. Bipolar disorders, 2012. 14(5): p. 478-487.

78. Mintun, M., et al., Brain oxygen utilization measured with O-15 radiotracers and positron emission tomography. Journal of nuclear medicine: official publication, Society of Nuclear Medicine, 1984. 25(2): p. 177-187.

79. Milak, M. S., et al., Pretreatment regional brain glucose uptake in the midbrain on PET may predict remission from a major depressive episode after three months of treatment. Psychiatry Research: Neuroimaging, 2009. 173(1): p. 63-70.

80. Farde, L., et al., Quantitative analysis of D2 dopamine receptor binding in the living human brain by PET. Science, 1986. 231(4735): p. 258-261.

81. DelParigi, A., et al., Sensory experience of food and obesity: a positron emission tomography study of the brain regions affected by tasting a liquid meal after a prolonged fast. Neuroimage, 2005. 24(2): p. 436-443.

82. Koepp, M. J., et al., Evidence for striatal dopamine release during a video game. Nature, 1998. 393(6682): p. 266-268.

83. Cleare, A. J., et al., Brain 5-HT$_{1A}$ receptor binding in chronic fatigue syndrome measured using positron emission tomography and [$^{11}$C] WAY-100635. Biological psychiatry, 2005. 57(3): p. 239-246.

84. Tirelli, U., et al., Brain positron emission tomography (PET) in chronic fatigue syndrome: preliminary data. The American journal of medicine, 1998. 105(3): p. 54S-58S.

85. Yamamoto, S., et al., Reduction of serotonin transporters of patients with chronic fatigue syndrome. Neuroreport, 2004. 15(17): p. 2571-2574.

86. Valk, P. E., Positron emission tomography: basic science and clinical practice. 2003, London; New York: Springer. xix, 884 p.

87. Alekhin, M. S., et al. Scintillation properties and self absorption in $SrI_2$:$Eu^{2+}$; in Nuclear Science Symposium Conference Record (NSS/MIC), 2010 IEEE. 2010.

88. Conti, M., State of the art and challenges of time-of-flight PET. Phys Med, 2009. 25(1): p. 1-11.

89. Pepin, C. M., et al., Properties of LYSO and recent LSO scintillators for phoswich PET detectors. Nuclear Science, IEEE Transactions on, 2004. 51(3): p. 789-795.

90. van Loef, E. V. D., et al., Scintillation properties of LaBr3:Ce3+ crystals: fast, efficient and high-energy-resolution scintillators. Nuclear Instruments and Methods in Physics Research Section A: Accelerators, Spectrometers, Detectors and Associated Equipment, 2002. 486(1-2): p. 254-258.

91. Lewellen, T. K., The challenge of detector designs for PET. American journal of roentgenology, 2010. 195(2): p. 301-309.

92. Ariño, G., et al., Energy and coincidence time resolution measurements of CdTe detectors for PET. Journal of Instrumentation, 2013. 8(02): p. C02015.

93. Renker, D. and E. Lorenz, Advances in solid state photon detectors. Journal of Instrumentation, 2009. 4(04): p. P04004.

94. Long, Y., J. A. Fessler, and J. M. Balter, 3D forward and back-projection for X-ray CT using separable footprints. Medical Imaging, IEEE Transactions on, 2010. 29(11): p. 1839-1850.

95. Schaart, D. R., et al., LaBr3: Ce and SiPMs for time-of-flight PET: achieving 100 ps coincidence resolving time. Physics in medicine and biology, 2010. 55(7): p. N179.

96. Madl, C. M., et al., Vapor phase polymerization of poly (3, 4-ethylenedioxythiophene) on flexible substrates for enhanced transparent electrodes. Synthetic Metals, 2011. 161(13): p. 1159-1165.

97. Hamasha, M. M., K. Alzoubi, and S. Lu, Behavior of sputtered indium-tin-oxide thin film on poly-ethylene terephthalate substrate under stretching. Display Technology, Journal of, 2011. 7(8): p. 426-433.

98. Bae, I.-T., et al., Intermetallic compound formation at Cu—Al wire bond interface. Journal of Applied Physics, 2012. 112(12): p. 123501.

99. Alazzam, A., et al. Design and Process Development Concerns for the Assembly of Very Small Solder Joints. in ASME 2012 International Mechanical Engineering Congress and Exposition. 2012. American Society of Mechanical Engineers.

100. Beutel, H., T. Stieglitz, and J. U. Meyer. Microflex: a new technique for hybrid integration for microsystems. in Micro Electro Mechanical Systems, 1998. MEMS 98. Proceedings, The Eleventh Annual International Workshop on. 1998. IEEE.

101. Dekker, R., et al. Living Chips and Chips for the living. in Bipolar/BiCMOS Circuits and Technology Meeting (BCTM), 2012 IEEE. 2012. IEEE.

102. Macias-Montero, J.-G., et al. VIP-PIX: A low noise readout ASIC for pixelated CdTe gamma-ray detectors for use in the next generation of PET scanners. in Nuclear Science Symposium and Medical Imaging Conference (NSS/MIC), 2012 IEEE. 2012. IEEE.

103. Gao, W., et al. A novel data acquisition scheme based on a low-noise front-end ASIC and a high-speed ADC for CZT-based PET imaging. in Real Time Conference (RT), 2012 18th IEEE-NPSS. 2012. IEEE.

104. Matsuda, H., et al., Development of ultra-fast ASIC for future PET scanners using TOF-capable MPPC detectors. Nuclear Instruments and Methods in Physics Research Section A: Accelerators, Spectrometers, Detectors and Associated Equipment, 2013. 699: p. 211-215.

105. Itzler, M. A., M. Entwistle, and X. Jiang. High-rate photon counting with Geiger-mode APDs. in IEEE Photonics Annual Meeting S. 2011.

106. Kolb, A., et al., Evaluation of Geiger-mode APDs for PET block detector designs. Phys Med Biol, 2010. 55(7): p. 1815-32.

107. Nomura, K., et al., Room-temperature fabrication of transparent flexible thin-film transistors using amorphous oxide semiconductors. Nature, 2004. 432(7016): p. 488-492.

108. Park, J. S., et al., Review of recent developments in amorphous oxide semiconductor thin-film transistor devices. Thin Solid Films, 2012. 520(6): p. 1679-1693.

109. Lerche, C., et al. Maximum likelihood based positioning and energy correction for pixelated solid state PET detectors. in Nuclear Science Symposium and Medical Imaging Conference (NSS/MIC), 2011 IEEE. 2011. IEEE.

110. Aliaga, R. J., et al., PET system synchronization and timing resolution using high-speed data links. Nuclear Science, IEEE Transactions on, 2011. 58(4): p. 1596-1605.
111. Aliaga, R. J., et al. Evaluation of a modular PET system architecture with synchronization over data links. in Nuclear Science Symposium and Medical Imaging Conference (NSS/MIC), 2012 IEEE. 2012. IEEE.
112. Kato, K., et al., Evaluation of Off-State Current Characteristics of Transistor Using Oxide Semiconductor Material, Indium-Gallium-Zinc Oxide. Japanese Journal of Applied Physics, 2012. 51(2R): p. 021201.
113. Kim, C. W., et al. 59.1: Invited Paper: LTPS Backplane Technologies for AMLCDs and AMOLEDs. in SID Symposium Digest of Technical Papers. 2011. Wiley Online Library.
114. Klauk, H. Organic thin-film transistors for flexible displays and circuits. in Device Research Conference (DRC), 2012 70th Annual. 2012. IEEE.
115. Renker, D., Geiger-mode avalanche photodiodes, history, properties and problems. Nuclear Instruments and Methods in Physics Research Section A: Accelerators, Spectrometers, Detectors and Associated Equipment, 2006. 567(1): p. 48-56.
116. Cova, S., et al., Avalanche photodiodes and quenching circuits for single-photon detection. Applied optics, 1996. 35(12): p. 1956-1976.
117. Rance, W., et al., 14%-efficient flexible CdTe solar cells on ultra-thin glass substrates. Applied Physics Letters, 2014. 104(14): p. 143903.
118. Brotherton, S. D., Introduction to Thin Film Transistors: Physics and Technology of TFTs. 2013: Springer.
119. Lee, Y. H. D., M. O. Thompson, and M. Lipson, Deposited low temperature silicon GHz modulator. Optics express, 2013. 21(22): p. 26688-26692.
120. Bubon, O., et al., Electroded avalanche amorphous selenium (a-Se) photosensor. Current Applied Physics, 2012. 12(3): p. 983-988.
121. Boileau, I., et al., In vivo evidence for greater amphetamine-induced dopamine release in pathological gambling: a positron emission tomography study with [$^{11}$C]-(+)-PHNO. Molecular psychiatry, 2013.
122. Price, J. C., Molecular brain imaging in the multimodality era. Journal of Cerebral Blood Flow & Metabolism, 2012. 32(7): p. 1377-1392.
123. Yamamoto, S., et al., Development of a brain PET system, PET-Hat: A wearable PET system for brain research. Nuclear Science, IEEE Transactions on, 2011. 58(3): p. 668-673.
124. de Jong, H. W., et al., Performance evaluation of the ECAT HRRT: an LSO-LYSO double layer high resolution, high sensitivity scanner. Physics in medicine and biology, 2007. 52(5): p. 1505.
125. van Velden, F. H., et al., HRRT versus HR+ human brain PET studies: an interscanner test-retest study. Journal of Nuclear Medicine, 2009. 50(5): p. 693-702.
126. Zimmer, L. and A. Luxen, PET radiotracers for molecular imaging in the brain: Past, present and future. NeuroImage, 2012. 61(2): p. 363-370.
127. Manjeshwar, R. M., et al. Fully 3D PET iterative reconstruction using distance-driven projectors and native scanner geometry. in Nuclear Science Symposium Conference Record, 2006. IEEE. 2006. IEEE.
128. Rapisarda, E., et al., Image-based point spread function implementation in a fully 3D OSEM reconstruction algorithm for PET. Physics in medicine and biology, 2010. 55(14): p. 4131.
129. Sandler, H. M., et al., Reduction in patient-reported acute morbidity in prostate cancer patients treated with 81-Gy Intensity-modulated radiotherapy using reduced planning target volume margins and electromagnetic tracking: assessing the impact of margin reduction study. Urology, 2010. 75(5): p. 1004-1008.
130. Jin, X., et al., Evaluation of motion correction methods in human brain PET imaging—A simulation study based on human motion data. Medical physics, 2013. 40(10): p. 102503.
131. RMD: A Dynasil Company. Solid State Photo Multipliers for PET. 2014 Apr. 29, 2014]; Available from: rmdinc.com/solid-state-photo-multipliers-for-pet/.
132. Qin, L., et al., Growth and characteristics of LYSO (Lu2(1-x-y)Y2xSiO5:Cey) scintillation crystals. Journal of Crystal Growth, 2005. 281(2-4): p. 518-524.
133. Rihua, M., Z. Liyuan, and Z. Ren-Yuan. Quality of a 28 cm long LYSO crystal and progress on optical and scintillation properties. in Nuclear Science Symposium Conference Record (NSS/MIC), 2010 IEEE. 2010.
134. Bloomfield, P. M., et al., The design and implementation of a motion correction scheme for neurological PET. Physics in medicine and biology, 2003. 48(8): p. 959.
135. Strother, S., M. Casey, and E. Hoffman, Measuring PET scanner sensitivity: relating countrates to image signal-to-noise ratios using noise equivalents counts. Nuclear Science, IEEE Transactions on, 1990. 37(2): p. 783-788.
136. Surti, S., Update on time-of-flight PET imaging. Journal of Nuclear Medicine, 2015. 56(1): p. 98-105.
137. Howell, J. R., M.P. Menguc, and R. Siegel, Thermal radiation heat transfer. 2010: CRC press.
138. Schmidtlein, C. R., Turner, J. N., Thompson, M. O., Mandal, K. C. Haggstrom, I, Zhang, J, Humm, J. L., Feiglin, D. H., Krol, A, "Performance modeling of a wearable brain PET (BET) camera," Medical Imaging conference (San Diego, 2016) appear in Proc SPIE v. 9788 (2016).
139. www.usa.philips.com/healthcare/product/HC882446/vereos-digital-pet-ct
140. D. N ter Weele, D. R. Schaart, and P. Dorenbos, "Scintillator Detector Timing Resolution; A study by Ray Tracing Software," IEEE Trans. Nuclear Science v. 62(5) Pp 1972-1980 (2015)
141. F. Acerbi, A. Ferri, A. Gola, M. Cazzanelli, L. Pavesi, N. Zorzi, and C. Piemonte, "Characterization of Single-Photon Time Resolution: From Single SPAD to Silicon Photomultiplier," IEEE Trans. Nuclear Science, v. 61(5) Pp. 2678-2686 (2014).
142. www.pethelmet.org/143. Conzalez, A. J., Stan Majewski, et al., "The MINDView brain PET detector, feasibility study based on SiPM arrays," Nuclear Instruments and Methods Physics Research A, v. 818 (2016) Pp 82-90.
144. Omura, T, T. Moriya, R. Yamada, H. Yamauchi, A. Saito, T. Sakai, T. Miwa, and M. Watanabe, "Development of a High-Resolution Four-Layer DOI Detector Using MPPCs for Brain PET," IEEE Nuclear Science Symposium and Medical Imaging Conference Record (NSS/MIC 2012), paper M18-41.
145. Inadama, N, T. Moriya, Y. Hirano, F. Nishikido, H. Murayama, E. Yoshida, H. Tashima, M. Nitta, H. Ito, and T. Yamaya, "X'tl Cube PET Detector Composed of a Stack of Scintillator Plates Segmented by Laser Processing," IEEE Trans. Nuclear Science v. 61(1), Pp. 53-59 (2014).
146. Vignetti, M. M., F. Calmon, R. Cellier, P. Pittet, L. Quizquerez, A. Savoy-Navarra, "Design guidelines for the integration of Geiger-mode avalanche diodes in standard CMOS technologies," Microelectronics Journal v. 46 Pp. 900-910 (2015)
147. Carbon, E, "Single-photon imaging in complementary metal oxide semiconductor processes," Phil. Trans. R. Soc. A 372: 20130100, dx.doi.org/10.1098/rsta.2013.0100
148. Harmon, E. S., M. Naydenkov, J. T. Hyland, "Compound semiconductor SPAD arrays," Proc. SPIE v. 8727, paper 87270N (2013)
149. Harmon, E. S., J. T. Hyland, M. Naydenkov, "Compound Semiconductor SPAD Arrays," New Developments in Photodetection, Tours, France, Jul. 4, 2014.
150. Harmon, E. S. "Integrated avalanche photodiode arrays," U.S. Pat. No. 9,076,707 (Jul. 7, 2015).
151. www.sensl.com
152. www.hamamatsu.com/eu/en/4004.html
153. www.ketek.net/products/sipm/154.
154. www.digitalphotoncounting.com/

What is claimed is:

1. A photon detector comprising:
a semiconductor configured to respond to receipt of at least one photon emission by producing an electrical signal having a timing resolution of smaller than 300 ps;
a clock, configured to generate a clock signal;
a logic circuit configured to digitize the electrical signal and associate the digitized electrical signal with a time of occurrence based on the clock to produce an event record having the timing resolution of smaller than 300 ps;
a memory, configured to store a plurality of the event records;
an automated communication interface; and
an automated processor configured to:
process the stored plurality of event records according to at least one criterion;
synchronize the clock with an external reference, by at least one communication through the automated communication interface; and
selectively transmit at least a subset of the processed plurality of event records through the automated communication interface.

2. The photon detector according to claim 1, further comprising a scintillator element configured to scintillate in response to energetic particles, wherein the semiconductor is operable coupled to the scintillator element to receive the at least one photon emission therefrom.

3. The photon detector according to claim 1, wherein the automated communication interface comprises a digital packet switched communication network.

4. The photon detector according to claim 1, further comprising a common housing, wherein at least the semiconductor, logic circuit, memory, the automated communication interface, and the automated processor are each provided within the common housing.

5. The photon detector according to claim 4, further comprising a plurality of the semiconductors, each respective semiconductor being optically coupled to a separate respective scintillation element within the common housing.

6. The photon detector according to claim 5, wherein each respective scintillator is optically and electrically isolated from each other scintillator element.

7. The photon detector according to claim 1, further comprising a scintillation crystal, wherein the semiconductor comprises a thin film photonic detector directly patterned on a surface of the scintillation crystal.

8. The photon detector according to claim 1, wherein the clock signal has a resolution of less than or equal to 100 nS.

9. The photon detector according to claim 1, wherein the clock signal has a resolution of less than or equal to 10 nS.

10. The photon detector according to claim 1, wherein the automated processor is further configured to receive control information through the automated communication interface.

11. The photon detector according to claim 1, wherein the automated processor is further configured to compensate for perturbations caused by at least one of temperature and dark current of the semiconductor.

12. The photon detector according to claim 1, wherein the semiconductor is configured to quantitatively response to an energy of the at least one photon emission, and the event record further comprises the energy of the at least one photon emission.

13. The photon detector according to claim 1, wherein the automated processor is further configured to process the stored plurality of event records according to at least one criterion comprising a detected scintillation energy range, the automated processor being further configured to selectively communicate event records dependent on the detected scintillation energy.

14. The photon detector according to claim 1, wherein the automated processor is further configured to process the stored plurality of event records according to at least one criterion comprising a time between successive event records.

15. The photon detector according to claim 1, wherein the logic circuit comprises an analog-to-digital converter, a buffer, and clock synchronization and time skew management logic integrated together with the semiconductor.

16. The photon detector according to claim 1, wherein the semiconductor is contained within a housing, and the automated processor is further configured to determine a spatial position of the housing.

17. The photon detector according to claim 1, further comprising a housing configured to house at least the semiconductor and the automated processor, further comprising a computer readable software storage medium containing software for controlling the automated processor.

18. A photon detection method, comprising:
providing a photon detector comprising:
a semiconductor configured to respond to receipt of at least one photon emission by producing an electrical signal having a timing resolution of smaller than 300 ps;
a clock, configured to generate a clock signal;
a logic circuit configured to digitize the electrical signal and associate the digitized electrical signal with a time of occurrence based on the clock to produce an event record having the timing resolution of smaller than 300 ps;
a memory, configured to store a plurality of the event records;
an automated communication interface; and
an automated processor;
synchronizing the clock with an external reference, by at least one communication through the automated communication interface;
storing a plurality of event records in the memory, each event record comprising at least a time of photon emission;
selectively processing the stored plurality of event records with the automated processor according to at least one event record dependent processing criterion; and transmitting at least a subset of the processed plurality of event records through the automated communication interface.

19. The photon detection method according to claim 18, further comprising receiving control information through the automated communication interface.

20. A photon detector, comprising:

a scintillation element;

a detector configured to respond to scintillation by the scintillation element by producing an signal corresponding to at least one photon emitted by the scintillation element, having a timing resolution of a time of emission of the at least one photon of less than 300 ps;

a memory;

a logic circuit configured to digitize the signal and associate the digitized signal with a time of occurrence of the at least one photon emission to produce an event record having the timing resolution of smaller than 300 ps;

a digital packet network communication interface; and an automated processor, configured to:

receive control information through the digital packet network communication interface;

synchronize a determination of the time of occurrence by communication through the digital packet network communication interface;

store a plurality of event records in the memory, each event record comprising at least a time of photon emission having the timing resolution of a time of emission of the at least one photon of less than 300 ps;

selectively process the plurality of event records according to at least one event record dependent processing criterion.

* * * * *